US006344466B2

(12) United States Patent
Soll et al.

(10) Patent No.: US 6,344,466 B2
(45) Date of Patent: Feb. 5, 2002

(54) BENZAMIDE AND SULFONAMIDE SUBSTITUED AMINOGUANIDINES AND ALKOXYGUANIDINES AS PROTEASE INHIBITORS

(75) Inventors: Richard M. Soll, Lawrenceville, NJ (US); Tianbao Lu; Bruce E. Tomczuk, both of Collegevile, PA (US); Thomas P. Markotan, Morgantown, PA (US); Colleen Siedem, Kennett Square, PA (US)

(73) Assignee: 3-Dimensional Pharmaceuticals Inc., Exton, PA (US)

( * ) Notice: Subject to any disclaimer, the term of this patent is extended or adjusted under 35 U.S.C. 154(b) by 0 days.

(21) Appl. No.: 09/796,319

(22) Filed: Feb. 28, 2001

Related U.S. Application Data

(62) Division of application No. 09/283,241, filed on Apr. 1, 1999
(60) Provisional application No. 60/080,568, filed on Apr. 3, 1998.

(51) Int. Cl.[7] .................. A61K 31/445; A61K 31/55; A61K 31/535; A61K 31/495
(52) U.S. Cl. .............. 514/331; 514/237.8; 514/217.11; 514/252.12; 514/253.01; 514/255.03; 514/307; 540/607; 544/162; 544/360; 544/386; 544/387; 546/145; 546/226
(58) Field of Search .................. 540/607; 544/162, 544/360, 386, 387; 546/145, 226; 514/237.8, 217.11, 252.12, 253.01, 255.03, 307, 331

(56) References Cited

U.S. PATENT DOCUMENTS

| | | | |
|---|---|---|---|
| 4,499,082 A | 2/1985 | Shenvi et al. | 514/2 |
| 4,652,440 A | 3/1987 | Paik et al. | 424/1.1 |
| 4,727,064 A | 2/1988 | Pitha | 514/58 |
| 4,764,604 A | 8/1988 | Müller | 536/103 |
| 4,957,939 A | 9/1990 | Gries et al. | 514/492 |
| 5,024,998 A | 6/1991 | Bodor | 514/58 |
| 5,322,926 A * | 6/1994 | Tripier et al. | 514/822 |
| 5,466,811 A | 11/1995 | Alexander | 546/283 |
| 5,792,769 A | 8/1998 | Lu et al. | 514/255 |
| 5,891,909 A | 4/1999 | Soll et al. | 514/517 |

FOREIGN PATENT DOCUMENTS

| | | |
|---|---|---|
| CA | 2164684 A1 | 6/1996 |
| EP | 0 604 022 A1 | 6/1994 |
| EP | 0 761 251 A1 | 3/1997 |
| WO | WO 95/07291 A1 | 3/1995 |
| WO | WO 96/11668 A1 | 4/1996 |
| WO | WO 96/32143 A1 | 10/1996 |
| WO | WO 96/38136 A1 | 12/1996 |
| WO | WO 97/11693 A1 | 4/1997 |
| WO | WO 97/22589 A1 | 6/1997 |
| WO | WO 97/36580 A1 | 10/1997 |
| WO | WO 98/23565 A2 | 6/1998 |
| WO | WO 99/51571 A1 | 10/1999 |

OTHER PUBLICATIONS

Barrett, A.J., "Proteinase inhibitors: potential drugs?" in *Enzyme Inhibitors as Drugs*, Sandler, M., ed., University Park Press, Baltimore, pp. 219–229 (1980).

Baugh, R.J. and J. Travis, "Human Leukocyte Granule Elastase: Rapid Isolation and Characterization," *Biochemistry* 15 :836–814, American Chemical Society (1976).

Bergeron, R.J. and J.S. McManis, "Total Synthesis of (±)–15–Deoxyspergualin," *J. Org. Chem* 52 .:1700–1703, American Chemical Society (1987).

Bernatowicz, M.S. et al., "1H–Pyrazole–1–carboxamidine Hydrochloride: An Attractive Reagent for Guanylation of Amines and Its Application to Peptide Synthesis," *J. Org. Chem.* 57:2497–2502, American Chemical Society (1992).

Bernatowicz, M.S. et al., "Urethane Protected Derivatives of 1–Guanylpyrazole for the Mild and Efficient Preparation of Guanidines," *Tetrahedron Lett.* 34:3389–3392, Pergamon Press Ltd (1993).

(List continued on next page.)

*Primary Examiner*—Amelia Owens
(74) *Attorney, Agent, or Firm*—Sterne, Kessler Goldstein & Fox PLLC

(57) ABSTRACT

The present invention is directed to aminoguanidine and alkoxyguanidine compounds, including compounds of Formula I:

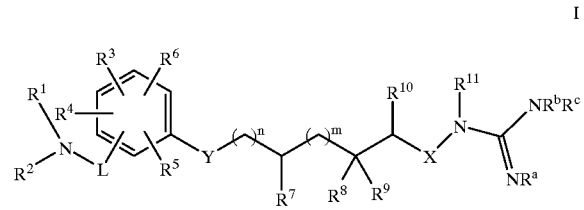

I wherein X is O or NH, L is —O— or —SO$_2$—, and R$^1$–R$^4$, R$^9$–R$^{19}$, R$^a$, R$^b$, R$^c$, Y, Z, n and m are set forth in the specification, as well as hydrates, solvates or pharmaceutically acceptable salts thereof, that inhibit proteolytic enzymes such as thrombin. Also described are methods for preparing the compounds of Formula I. Certain of the compounds exhibit antithrombotic activity via direct, selective inhibition of thrombin, or are intermediates useful for forming compounds having antithrombotic activity. The invention includes a composition for inhibiting loss of blood platelets, inhibiting formation of blood platelet aggregates, inhibiting formation of fibrin, inhibiting thrombus formation, and inhibiting embolus formation in a mammal. Other uses of compounds of the invention are as anticoagulants either embedded in or physically linked to materials used in the manufacture of devices used in blood collection, blood circulation, and blood storage.

42 Claims, No Drawings

OTHER PUBLICATIONS

Bodor, N. and J.H. Miller, "Novel Approaches in Prodrug Design," *Drugs of the Future VI*:165–182, Prous Science (1981).

Bundgaard, H., "Design of prodrugs: Bioreversible derivatives for various functional groups and chemical entities," in *Design of Prodrugs*, Bundgaard, H., ed., Elsevier Science Publishers B. V., Amsterdam, The Netherlands, pp. 1–92 (1985).

Claeson, G., "Synthetic peptides and peptidomimetics as substrates and inhibitors of thrombin and other proteases in the blood coagulation system, " *Blood Coag. & Fibrin.* 5:411–436, Rapid Communications of Oxford Ltd (1994).

Coughlin, S.R., "Molecular Mechanisms of Thrombin Signaling," *Semin. Hematol. 31*:270–277, W.B. Saunders Company (1994).

Cuypers, H.T. et al., "Sulfhydryl Content of Bovine Eye Lens Leucine Aminopeptidase," *J. Biol. Chem. 257*:7086–7091, The American Society of Biological Chemists, Inc. (1982).

Harker, L.A., "Strategies for inhibiting the effects of thrombin," *Blood Coag. & Fibrin.* 5:S47–S58, Rapid Communications of Oxford Ltd (1994).

Jeong, J.–H. et al., "Cyclic Guanidino–Sugars with Low $pK_a$ as Transition–State Analog Inhibitors of Glycosidases: Neutral Instead of Charged Species Are the Active Forms," *J. Am. Chem. Soc. 118*:4227–4234, American Chemical Society (1996).

Khadilkar, B.M. and Samant, S.D., "Synthesis and pharmacology of 2–[3–(4–aryl–1–piperazinyl)–2–hydroxupropll/3–oxopropyl/propxy]–1H–isoindole–1,3(2H)–diones," *Ind. J. Chem. 32B*:1137–1142, The Indian National Science Academy (1993).

Khaw, B.A. et al., "Myocardial Infarct Imaging of Antibodies to Canine Cardiac Myosin with Indium–111–Diethylenetriamine Pentaacetic Acid," *Science 209*:295–297, American Association for the Advancement of Science (1980).

Kim, K.S. et al., "Preparation of Argatroban Analog Thrombin Inhibitors with Reduced Basic Guanidine Moiety, And Studies of Their Cell Permeability and Antithrombotic Activities, " *Med. Chem. Res. 6*:377–383, Birkhauser Boston (1996).

Lefkovits, J. and Topol, E.J., "Direct Thrombin Inhibitors in Cardiovascular Medicine," *Circulation 90*:1522–1536, american Heart Association, Inc. (1994).

Miller, A.E. and J.J. Bischoff, "A Facile Conversion of Amino Acids to Guanidino Acids," *Synthesis 9*:777–779, Thieme Inc. (1986).

Notari, R.E., "Theory and Practice of Prodrug Kinetics," *Meth. Enzym. 112*:309–323, Academic Press, Inc. (1985).

Rieke, R.D. et al., "Highly Reactive Magnesium for the Preparation of Grignard Reagents: 1–Norbornanecarboxylic Acid," in *Organic Syntheeis. Collective vol. 6*, Noland, W.E., ed., John Wiley & Sons, New York, NY, pp. 845–852 (1988).

Saulnier, M.G. et al., "An Efficient Method for the Synthesis of Guanidino Prodrugs," *Bioorg. & Med. Chem. Lett. 4*:1985–1990, Elsevier Science Ltd (1994).

Tapparelli, C. et al., "Synthetic low–molecular weight thrombin inhibitors: molecular design and pharmacological profile," *Trends Pharmacol. Sci. 14*:366–376, Elsevier Science Publishers Ltd (1993).

English language abstract of WO 96/32143 (Document AP1), Derwent World Patents Index, WPI Accession No. 96–476853/199647.

\* cited by examiner

BENZAMIDE AND SULFONAMIDE SUBSTITUED AMINOGUANIDINES AND ALKOXYGUANIDINES AS PROTEASE INHIBITORS

This application is a division of U.S. applica on Ser. No. 09/283,241, filed on Apr. 1, 1999, which claims the benefit, under 35 U.S.C. §119(e), of U.S. Provisional Application No. 60/080,568, filed on Apr. 3, 1998. The entirety of each of these applications is incorporated by reference herein.

BACKGROUND OF THE INVENTION

1. Field of the Invention

The present invention relates to novel compounds that function as enzyme inhibitors, and particularly to a new class of non-peptidic inhibitors ofproteolytic enzymes.

2. Related Art

Proteases are enzymes that cleave proteins at single, specific peptide bonds. Proteases can be classified into four generic classes: serine, thiol or cysteinyl, acid or aspartyl, and metalloproteases (Cuypers et al., *J. Biol. Chem.* 257:7086 (1982)). Proteases are essential to a variety of biological activities. such as digestion, formation and dissolution of blood clots, reproduction and the immune reaction to foreign cells and organisms. Aberrant proteolysis is associated with a number of disease states in man and other mammals. The human neutrophil proteases, elastase and cathepsin G, have been implicated as contributing to disease states marked by tissue destruction. These disease states include emphysema, rheumatoid arthritis, corneal ulcers and glomerular nephritis. (Barret, in *Enzyme Inhibitors as Drugs*, Sandler, ed., University Park Press, Baltimore, (1980)). Additional proteases such as plasmin, C-1 esterase, C-3 convertase, urokinase, plasminogen activator, acrosin, and kallikreins play key roles in normal biological functions of mammals. In many instances, it is beneficial to disrupt the function ofone or more proteolytic enzymes in the course of therapeutically treating a mammal.

Serine proteases include such enzymes as elastase (human leukocyte), cathepsin G, plasmin, C-1 esterase, C-3 convertase, urokinase, plasminogen activator, acrosin, chymotrypsin, trypsin; thrombin, factor Xa and kallikreins.

Human leukocyte elastase is released by polymorphonuclear leukocytes at sites of inflammation and thus is a contributing cause for a number of disease states. Cathepsin G is another human neutrophil serine protease. Compounds with the ability to inhibit the activity of these enzymes are expected to have an anti-inflammatory effect useful in the treatment of gout, rheumatoid arthritis and other inflammatory diseases, and in the treatment of emphysema. Chymotrypsin and trypsin are digestive enzymes. Inhibitors of these enzymes are useful in treating pancreatitis. Inhibitors ofurokinase and plasminogen activator are usefiul in treating excessive cell growth disease states, such as benign prostatic hypertrophy, prostatic carcinoma and psoriasis.

The serine protease thrombin occupies a central role in hemostasis and thrombosis, and as a multifactorial protein, induces a number of effects on platelets, endothelial cells, smooth muscle cells, leukocytes, the heart. and neurons (Tapparelli et al., *Trends in Phaymacological Sciences* 14:366–376 (1993); Lefkovits and Topol, *Circulation* 90(3):1522–1536(1994); Harker, *Blood Coagulation and Fibrinolysis* 5 (Suppl 1):S47–S58 (1994)). Activation of the coagulation cascade through either the intrinsic pathway (contact activation) or the extrinsic pathway (activation by exposure of plasma to a non-endothelial surface, damage to vessel walls or tissue factor release) leads to a series of biochemical events that converge on thrombin. Thrombin cleaves fibrinogen ultimately leading to a hemostatic plug (clot formation), potently activates platelets through a uniqueofproteolytic cleavage of the cell surface thrombin receptor (Coughlin, *Seminars in Hematology* 31(4):270–277 (1994)), and autoamplifies its own production through a feedback mechanism. Thus, inhibitors of thrombin function have therapeutic potential in a host of cardiovascular and non-cardiovascular diseases, including: myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoagulability during chemotherapy; Alzheimer's disease; Down's syndrome; fibrin formation in the eye; and wound healing. Other uses include the use of said thrombin inhibitors as anticoagulants either embedded in or physically linked to materials used in the manufacture of devices used in blood collection, blood circulation, and blood storage, such as catheters, blood dialysis machines, blood collection syringes and tubes, blood lines and stents.

Factor Xa is another serine protease in the coagulation pathway. Factor Xa associates with factor Va and calcium on a phospholipid membrane thereby forming aprothrombinase complex. This prothrombinase complex then converts prothrombin to thrombin (Claeson, *Blood Coagulation and Fibrinolysis* 5:411–436 (1994); Harker, *Blood Coagulation and Fibrinolysis* 5 (Suppl 1):S47–S58 (1994)). Inhibitors of factor Xa are thought to offer an advantage over agents that directly inhibit thrombin since direct thrombin inhibitors still permit significant new thrombin generation (Lefkovits and Topol, *Circulation* 90(3):1522–1536 (1994); Harker, *Blood Coagulation and Fibrinolysis* 5 (Suppl 1):S47–S58 (1994)).

A need continues to exist for non-peptidic compounds that are potent and selective protease inhibitors, and which possess greater bioavailability and fewer side-effects than currently available protease inhibitors. Accordingly, new classes of potent protease inhibitors, characterized by potent inhibitory capacity and low mammalian toxicity, are potentially valuable therapeutic agents for a variety of conditions, including treatment of a number of mammalian proteolytic disease states.

SUMMARY OF THE INVENTION

The present invention is directed to novel compounds having Formula I (below). Also provided are processes for preparing compounds of Formula I. The novel compounds of the present invention are potent inhibitors of proteases, especially trypsin-like serine proteases, such as chymotrypsin, trypsin, thrombin, plasmin and factor Xa. Certain of the compounds exhibit antithrombotic activity via direct, selective inhibition ofthrombin, or are intermediates useful for forming compounds having antithrombotic activity.

The invention includes a composition for inhibiting loss ofblood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood. blood products, or mammalian organs in order to effect the desired inhibitions.

Also provided are methods of inhibiting or treating aberrant proteolysis in a mammal, and methods for treating myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoagulability during chemotherapy; Alzheimer's disease; Down's syndrome; fibrin formation in the eye; and wound healing. Other uses of compounds of the invention are as anticoagulants either embedded in or physically linked to materials used in the manufacture of devices used in blood collection, blood circulation. and blood storage, such as catheters, blood dialysis machines, blood collection syringes and tubes, blood lines and stents.

The invention also includes a method for reducing the thrombogenicity of a surface in a mammal by attaching to the surface, either covalently or noncovalently, a compound of the invention.

DETAILED DESCRIPTION OF THE PREFERRED EMBODIMENTS

The present invention is directed to a novel class of benzamide and sulfonamide derivatives having Formula I:

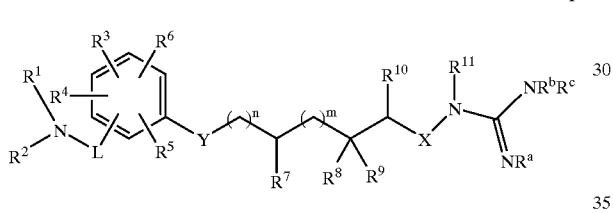

I or a solvate, hydrate or pharmaceutically acceptable salt thereof; wherein:

L represents —C(O)— or —SO$_2$—;

R$^1$ represents a group:

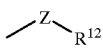

R$^2$ represents a group:

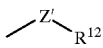

or R$^1$ and R$^2$ can be taken together with the nitrogen atom to which they are attached to form a three to seven membered ring, which optionally contains an additional nitrogen or oxygen atom, and which is optionally benzo- or pyrido-fused, said ring being preferably saturated, and said ring having one or two optional substituents on either a ring carbon or nitrogen selected from the group consisting of halogen, hydroxy, acyloxy, alkoxy, aryloxy, alkyl, cycloalkyl, alkenyl, alkynyl, aryl, aralkyl, heteroaryl, heteroar(C$_{1-4}$)alkyl, carboxyalkyl, alkoxycarbonylalkyl, hydroxyalkoxyalkyl, cyano(C$_{2-10}$)alkyl, hydroxy(C$_{2-10}$)alkyl, alkoxy(C$_{2-10}$)alkyl, alkoxyalkyl, mono- and di-alkylamino(C$_{2-10}$)alkyl, carboxy, alkoxycarbonyl, carboxamido, formyl, alkanoyl, aroyl, aralkanoyl, sulfonyl, alkylsulfonyl, alkoxysulfonyl, and NR$^{13}$R$^{14}$ (when C-substituted);

R$^{12}$ represents hydrogen, C$_{3-7}$ cycloalkyl, C$_{3-7}$ cycloalkenyl, C$_{3-7}$ heterocycloalkyl, C$_{3-7}$ heterocycloalkenyl, aryl, or heteroaryl, which groups are optionally substituted with C$_{16}$ alkyl or hydroxy, or R$^{12}$ represents diarylmethyl, diheteroarylmethyl, dicycloalkylmethyl or (aryl)(heteroaryl)CH—;

Z and Z' independently represent a bond, a C$_{1-6}$alkyl chain, a C$_{3-6}$ alkenyl chain, or a C$_{3-6}$alkynyl chain, where one or two nitrogen, oxygen, or sulfur atoms may be optionally contained within each chain, and the chains are optionally substituted by one or more groups selected from halogen, hydroxy, CN, C$_{1-6}$ alkyl, C$_{1-6}$ alkoxy, C$_{1-6}$ alkoxy(C$_{1-6}$)alkyl, C$_{1-6}$ acyloxy, NR$^{13}$R$^{14}$, NHCOR$^{15}$, NHSO$_2$R$^{16}$, COR$^{15}$, CO$_2$R$^{15}$, CONR$^{13}$R$^{14}$, and SO$_2$NR$^{17}$R$^{18}$;

provided that when one of R$^1$ or R$^2$ is C$_{3-8}$ alkyl, cycloalkyl, C$_{3-8}$ alkenyl, C$_{3-8}$ alkynyl, aryl, aralkyl, or heteroaryl, any of which is optionally substituted, then the other of R$^1$ or R$^2$ is other than hydrogen, alkyl, aralkyl, aryl, hydroxy(C$_{2-10}$)alkyl, amino(C$_{2-10}$)alkyl, monoalkylamino(C$_{2-10}$)alkyl, dialkylamino(C$_{2-10}$) alkyl or carboxyalkyl;

R$^{13}$–R$^{16}$ represent hydrogen, C$_{1-6}$alkyl, C$_{3-7}$ cycloalkyl, C$_{2-6}$ alkenyl, C$_{2-6}$ alkynyl, C$_{6-10}$ aryl, mono- or di-hydroxy(C$_{6-10}$)aryl, C$_{6-10}$ ar(C$_{1-4}$)alkyl, pyridyl, pyridyl(C$_{1-4}$)alkyl, carboxy(C$_{1-6}$)-alkyl, C$_{1-4}$ alkoxycarbonyl(C$_{1-4}$)alkyl, cyano(C$_{2-6}$)alkyl, hydroxy (C$_{2-6}$)alkyl, C$_{1-4}$ alkoxy(C$_{2-6}$)alkyl, mono- and di-(C$_{1-4}$)alkylamino(C$_{2-6}$)alkyl;

or R$^{13}$ and R$^{14}$ form a C$_{3-7}$ heterocycloalkyl ring, or R$^{16}$ additionally may represent trifluoromethyl;

R$^{17}$ and R$^{18}$ are independently selected from the group consisting of hydrogen, C$_{1-6}$ alkyl, C$_{3-7}$ cycloalkyl, C$_{2-6}$ alkenyl, C$_{2-6}$ alkynyl, C$_{6-10}$ aryl, C$_{6-10}$ ar(C$_{1-4}$) alkyl, pyridyl, pyridyl(C$_{1-4}$)alkyl, carbbxy(C$_{1-6}$)alkyl, C$_{1-4}$alkoxycarbonyl-(C$_{1-4}$)alkyl, cyano(C$_{2-6}$)alkyl, hydroxy(C$_{2-6}$)alkyl, C$_{1-4}$ alkoxy(C$_{2-6}$)alkyl, and mono- and di-(C$_{1-4}$)alkylamino(C$_{2-6}$)alkyl, or R$^{17}$ and R$^{18}$ can be taken together with the nitrogen atom to which they are attached to form a heterocyclic ring selected from the group consisting of N-morpholino, N-piperazinyl (optionally N' substituted with C$_{1-6}$ alkyl, C$_{1-6}$hydroxyalkyl, C$_{6-10}$ aryl, C$_{6-10}$ aryl(C$_{1-6}$)alkyl, C$_{1-6}$ alkylsulfonyl, C$_{6-10}$ arylsulfonyl, C$_{1-6}$ alkylcarbonyl, morpholino or C$_{6-10}$ arylcarbonyl), N-pyrrolyl, N-piperidinyl, N-pyrrolidinyl, N-dihydropyridyl, N-indolyl, wherein said heterocyclic ring can be optionally C-substituted;

R$^3$, R$^4$, R$^5$ and R$^6$ are each independently one of hydrogen, alkyl, cycloalkyl, alkenyl, alkynyl, optionally substituted aryl, optionally substituted aralkyl, optionally substituted heteroaryl, trifluoromethyl, halogen, hydroxyalkyl, cyano, nitro, carboxamido, —CO$_2$R$^x$, —CH$_2$OR$^x$ or —OR$^x$, or when present on adjacent carbon atoms, R$^3$ and R$^4$ may also be taken together to form one of —CH=CH—CH=CH— or —(CH$_2$)$_q$—, where q is from 2 to 6, and R$^5$ and R$^6$ are defined as above;

R$^x$, in each instance, is independently one of hydrogen, alkyl or cycloalkyl wherein said alkyl or cycloalkyl groups may optionally have one or more unsaturations;

Y is one of —O—, —NR$^{19}$—, —S—, —CHR$^{19}$— or a covalent bond;

R$^{19}$, in each instance, is independently hydrogen, C$_{1-6}$ alkyl, benzyl, phenyl, C$_{2-10}$ hydroxyalkyl, C$_{2-10}$ aminoalkyl, C$_{1-4}$ monoalkylamino(C$_{2-8}$)alkyl, C$_{1-4}$ dialkylamino(C$_{2-8}$)alkyl or C$_{2-10}$ carboxyalkyl;

$R^7$ is one of hydrogen, alkyl, aralkyl, aryl, hydroxyalkyl, aminoalkyl, monoalkylaminoalkyl, dialkylaminoalkyl, carboxyalkyl, hydroxy, alkoxy, aralkoxy, aryloxy, heteroaryloxy, or mono- or di- alkylamino, provided that n is other than zero when $R^7$ is hydroxy, alkoxy, aralkoxy, aryloxy, heteroaryloxy, or mono- or di- alkylamino;

$R^8$, $R^9$ and $R^{10}$ are each independently one of hydrogen, alkyl, aralkyl, aryl, hydroxyalkyl, aminoalkyl, monoalkylaminoalkyl, dialkylaminoalkyl or carboxyalkyl;

or $R^7$ and $R^8$ are taken together to form $-(CH_2)_y-$, where y is zero (a bond), 1 or 2, while $R^9$ and $R^{10}$ are defined as above; or $R^7$ and $R^{10}$ are taken together to form $-(CH_2)_t-$, where t is zero (a bond), or 1 to 8, while $R^8$ and $R^9$ are defined as above; or $R^8$ and $R^9$ are taken together to form $-(CH_2)_r-$, where r is 2–8, while $R^7$ and $R^{10}$ are defined as above;

X is oxygen or NH;

$R^{11}$ is one of hydrogen, alkyl, aralkyl, aryl, hydroxyalkyl, aminoalkyl, monoalkylamino$(C_{2-10})$alkyl, dialkylamino$(C_{2-10})$alkyl or carboxyalkyl;

$R^a$, $R^b$ and $R^c$ are independently hydrogen, alkyl, hydroxy, alkoxy, aryloxy, aralkoxy, alkoxycarbonyloxy, cyano or $-CO_2R^w$;

$R^w$ is alkyl, trichloroethyl, cycloalkyl, phenyl, benzyl,

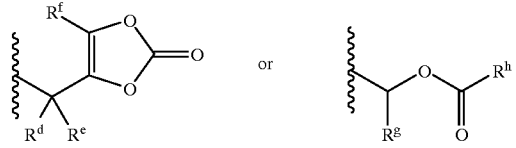

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-4\ 6}$ alkyl;

n is from zero to 8; and m is from zero to 4.

The moiety $-L-NR^1R^2$ is attached to the benzene ring in a position ortho-, meta-, or para- to Y, with the meta-position being preferred.

Preferably, the compounds have the structure of Formula Ia:

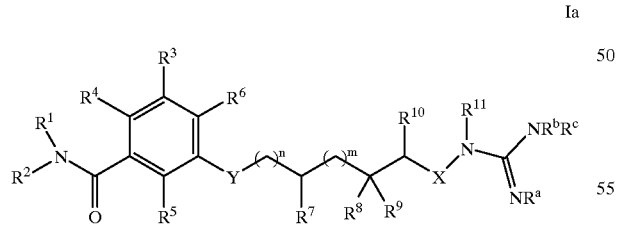

wherein each of the groups is as defined for Formula I above.

Referring to the general Formula I and Formula Ia, where $R^2$ represents a group

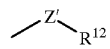

Z' is suitably $C_{3-6}$ alkenyl, e.g., allyl, or $C_{1-6}$ alkyl, e.g., methyl, ethyl, propyl or pentyl, which optionally contains an oxygen group within the chain and is optionally substituted by a group selected from hydroxy, $C_{1-6}$ alkoxy, $NHSO_2R^{16}$, $CO_2R^{15}$, $CONR^{13}R^{14}$, or $SO_2NR^{17}R^{18}$, and $R^{12}$ is suitably hydroge $C_{3-7}$ heterocycloalkyl, e.g., pyrrolidine or morpholine, aryl, e.g., phenyl which is optionally substituted by $CO_2R^{15}$, or heteroaryl, e.g., oxadiazole optionally substituted by hydroxy, triazole, or tetrazole optionally substituted by $C_{1-6}$ alkyl Referring to the general Formula I and Formula Ia where $R^1$ represents a group

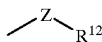

Z is suitably a bond or $C_{1-6}$ alkyl group, e.g., methyl, isopropyl or isobutyl, and $R^{12}$ suitably represents hydrogen, $C_{3-7}$ cycloalkyl, aryl, or heteroaryl. When Z represents a bond, $R^{12}$ is preferably optionally substituted phenyl, $C_{3-7}$ cycloalkyl, e.g., cyclobutyl, cyclopentyl or cyclohexyl, diphenylmethyl or dicyclohexylmethyl. When Z represents a $C_{1-4}$ alkyl group, $R^{12}$ is preferably hydrogen, cycloalkyl, e.g., cyclohexyl, or heteroaryl, e.g., thienyl or furyl.

Useful values of $R^{12}$ include $C_{6-10}$ aryl, pyridinyl, thiophenyl (i.e., thiophene), quinazolinyl, quinolinyl, isoquinolinyl, or tetrahydroquinolinyl, any of which is optionally substituted by one or two of hydroxy, nitro, trifluoromethyl, halogen, $C_{1-6}$ alkyl, $C_{1-6}$ alkoxy, $C_{1-6}$ aminoalkyl, $C_{1-4}$ aminoalkoxy, amnuo,mono$(C_{1-4})$ alkylamino, di$(C_{1-4})$alkylamino, $C_{2-6}$ alkoxycarbonylamino, $C_{2-6}$ alkoxycarbonyl, carboxy, $C_{1-4\ 6}$ hydroxyalkyl, $C_{2-6}$ hydroxyalkoxy, $C_{2-10}$ mono(carboxyalkyl)amino, bis$(C_{2-10}$ carboxyalkyl)amino, $C_{1-4}$ ar$(C_{1-6})$ alkoxycarbonyl, $C_{2-4}$ alkynylcarbonyl, $C_{1-4\ 6}$ alkylsulfonyl, $C_{2-6}$ alkenylsulfonyl, $C_{2-6}$ alkynylsulfonyl, $C_{1-6}$ alkylsulfinyl, $C_{1-6}$ alkylsulfonamido, amidino, guanidino, $C_{1-6}$ alkyliminoamino, formyliminoamino, $C_{2-6}$ carboxyalkoxy, $C_{2-6}$ carboxyalkyl, carboxyalkylamino, cyano, trifluoromethoxy, perfluoroethoxy, $C_{1-6}$ acyloxy, and $R^{17}R^{18}NSO_2-$, where $R^{17}$ and $R^{18}$ are independently selected from the group consisting of hydrogen, $C_{1-6}$ alkyl, $C_{3-7}$ cycloalkyl, $C_{2-6}$ alkenyl, $C_{1-2}$ alkynyl, $C_{6-10}$ aryl, $C_{6-1}$ar$(C_{1-4})$alkyl, pyridyl, pyridyl$(C_{1-4})$alkyl, carboxy $(C_{1-6})$alkyl, $C_{1-4}$ alkoxycarbonyl$(C_{1-4})$alkyl cyano$(C_{2-6})$alkyl, hydroxy$(C_{2-6})$alkyl, $C_{1-4}$ alkoxy$(C_{2-6})$alkyl, mono- and di-$(C_{1-4})$alkylamino$(C_{2-6})$alkyl, or $R^{17}$ and $R^{18}$ can be taken together with the nitrogen atom to which they are attached to form a heterocyclic ring selected from the group consisting of N-morpholino, N-piperazinyl (optionally N' substituted with $C_{1-6}$ alkyl, $C_{1-6}$ hydroxyalkyl, $C_{6-10}$ aryl, $C_{6-10}$ aryl$(C_{1-6})$alkyl, $C_{1-6}$ alkylsulfonyl, $C_{6-10}$ arylsulfonyl, $C_{1-6}$ alkylcarbonyl, morpholino or $C_{6-10}$ arylcarbonyl), N-pyrrolyl, N-piperidinyl, N-pyrrolidinyl, N-dihydropyridyl, N-indolyl, wherein said heterocyclic ring can be optionally substituted with one or two of hydroxy, $C_{1-8}$ alkanoyloxy, $C_{1-6}$ alkoxy, $C_{6-10}$ aryloxy, amino, mono- and di-$C_{1-6}$ alkylamino, $C_{1-8}$ alkanoylamino, $C_{1-4}$ alkyl, $C_{3-7}$ cycloalkyl, $C_{6-10}$ aryl, $C_{6-10}$ ar$(C_{1-4})$alkyl, heterocycle, heterocycloalkyl, carboxy$(C_{1-6})$alkyl, $C_{1-4}$ alkoxycarbonyl$(C_{1-4})$alkyl, cyano$(C_{2-6})$alkyl, hydroxy$(C_{2-6})$alkyl, $C_{1-4}$ alkoxy$(C_{2-6})$alkyl, mono- and di-$(C_{1-4})$alkylamino$(C_{2-6})$alkyl, carboxy, $C_{1-6}$ alkoxycarbonyl, carboxamido, formyl, $C_{1-6}$ alkanoyl, $C_{6-10}$ aroyl, $C_{6-10}$ ar$(C_{1-4})$alkanoyl, sulfonyl, $C_{1-6}$ alkylsulfonyl, $C_{1-6}$ alkoxysulfonyl, sulfonamido, phosphonyl, phosphoramido, or phosphinyl.

$R^{12}$ is more preferably one of phenyl, naphthyl, pyridyl, thiophenyl, quinolinyl or isoquinolinyl, optionally substituted by one or two of chloro, methoxy, methyl, trifluoromethyl, phenyl, cyano, nitro, amino, dimethylamino, alkylsulfonyl, arylsulfonyl, or $R^{17}R^{18}NSO_2$—, where $R^{17}$ and $R^{18}$ are defined as above.

Particularly preferred combinations of $R^1$ and $R^2$ include:

(A) $R^1$ and $R^2$ are taken together with the nitrogen to which they are attached to form a $C_{3-7}$ heterocycloalkyl or $C_{3-7}$ heterocycloalkenyl group, optionally benzo fused and optionally including an oxygen atom or an additional nitrogen atom, and which may be optionally substituted by $C_{1-6}$ alkyl, hydroxy, $C_{1-4}$ alkoxy, $C_{2-6}$ alkoxycarbonyl, formyl, $(C_{6-10})ar(C_{1-4})alkyl$, $C_{6-10}$ aryl, pyrid hydroxyalkoxyalkyl, halogen, or $NR^{13}R^{14}$; or (B) $R^1$ is $C_{3-7}$ cycloalkyl or $C_{3-7}$ cycloalkenyl, either ofwhich is optionally substituted by $C_{1-6}$ alkyl, hydroxy, $C_{1-4}$ alkoxy, halogen, carboxylic acid, a $C_{1-4}$ carboxylic acid ester group, or $NR^{13}R^{14}$, and $R^2$ is $C_{3-6}$ alkenyl, or $C_{3-6}$ alkynyl, either of which is optionally substituted by $C_{1-6}$ alkyl, hydroxy, $C_{1-4}$ alkoxy, halogen, carboxylic acid, a $C_{1-4}$carboxylic acid ester group, or $NR^{13}R^{14}$; or (C) $R^1$ is $C_{3-7}$ heterocycloalkyl($C_{1-6}$)alkyl, $C_{3-7}$ heterocvcloalkenyl($C_{1-6}$)alkyl, heteroaryl($C_{1-6}$)alkyl, $C_{3-7}$ heterocycloalkyl($C_{3-6}$)alkenyl, $C_{3-7}$ heterocycloalkenyl($C_{3-6}$)alkenyl, heteroaryl($C_{3-6}$) alkenyl, $C_{3-7}$ heterocycloalkyl($C_{3-6}$)alkynyl, $C_{3-7}$ heterocycloalkenyl($C_{3-6}$)alkynyl, heteroaryl($C_{3-6}$) alkynyl, di($C_{5-10}$ aryl)($C_{1-3}$)alkyl, di($C_{3-8}$ cycloalkyl)($C_{1-3}$)alkyl or di($C_{3-6}$ cycloalkenyl)($C_{1-3}$)alkyl, any of which is optionally substituted by $C_{1-6}$ alkyl, hydroxy, $C_{1-4}$ alkoxy, halogen, carboxylic acid, a $C_{1-4}$ carboxylic acid ester group, or $NR^{13}R^{14}$; and $R^2$ is a group

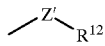

where $R^{12}$ and $Z'$ have the values and preferred values defined above.

$R^3$ can represent hydrogen, $C_{1-3}$ alkyl, halogen, or $C_{1-2}$ alkoxy. $R^3$ is preferably $C_{1-3}$ alkyl, e.g., methyl, or halogen, e.g., chlorine or bromine.

$R^4$, $R^5$ and $R^6$ can independently represent hydrogen, or halogen. $R^4$, $R^5$ and $R^6$ are preferably hydrogen, or halogen, e.g., fluorine.

Preferred values of Y are divalent oxygen (—O—), —$NR^{19}$— or a covalent bond, most preferably —O—.

Preferred values of $R^{19}$ are hydrogen, $C_{1-6}$ alkyl and $C_{3-6}$ cycloalkyl.

Preferred values of $R^{11}$ are hydrogen, $C_{1-6}$ alkyl, or $C_{6-10}$ ar($C_{1-6}$)alkyl.

Preferred values of $R^7$, $R^8$, $R^9$ and $R^{10}$ are independently one of hydrogen, $C_{1-6}$ alkyl, $C_{6-10}$ ar($C_{1-6}$)alkyl, $C_{6-10}$ aryl, $C_{2-10}$ hydroxyalkyl or $C_{2-7}$ carboxyalkyl. Useful values of $R^7$, $R^8$, $R^9$ and $R^{10}$ include hydrogen, methyl, ethyl, propyl, n-butyl, benzyl, phenylethyl, 2-hydroxyethyl, 3-hydroxypropyl, 4-hydroxybutyl, 2-carboxymethyl, 3-carboxyethyl and 4-carboxypropyl. Additional preferred compounds are those wherein $R^7$ and $R^8$ are taken together to form —$(CH_2)_y$— where y is most preferably 2. Another group of preferred compounds are those where $R^8$ and $R^9$ are taken together to form —$(CH_2)_r$— where r is most preferably 2.

A preferred value of X is O.

Preferred values of $R^a$, $R^b$ and $R^c$ in Formula I are hydrogen, hydroxy, $C_{1-6}$ alkyl, $C_{1-6}$ alkoxy, cyano or —$CO_2R^w$, where $R^w$, in each instance, is preferably one of $C_{1-4}$alkyl, $C_{4-7}$cycloalkyl or benzyloxycarbonyl. Suitable values of $R^a$, $R^b$ and $R^c$ include hydrogen, methyl, ethyl, propyl, n-butyl, hydroxy, methoxy, ethoxy, cyano, —$CO_2CH_3$, —$CO_2CH_2CH_3$ and —$CO_2CH_2CH_2CH_3$. In the most preferred embodiments, $R^a$, $R^b$ and $R^c$ are each hydrogen.

Also preferred at $R^a$, $R^b$ and $R^c$ is the group —$CO_2R^w$, where $R^w$ is one of

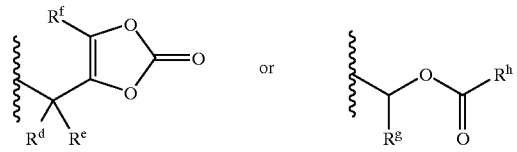

where $R^d$–$R^h$ are defined as above. When $R^a$, $R^b$ and $R^c$ are —$CO_2R^w$, where $R^w$ is one of one of these moieties, the resulting compounds are prodrugs that possess desirable formulation and bioavailability characteristics. A preferred value for each of $R^d$, $R^e$ and $R^g$ is hydrogen, $R^f$ is methyl, and preferred values for $R^h$ include benzyl and tert-butyl.

Preferred values of n in Formula I include from zero to 6, more preferably from zero to 4, and most preferably zero, 1 or 2. Preferred values of m include from zero to 4, more preferably zero, 1, 2 or 3.

A preferred group of compounds falling within the scope of the present invention include compounds of Formula Ia wherein:

(A) $R^1$ and $R^2$ are taken together with the nitrogen to which they are attached to form a $C_{3-7}$ heterocycloalkyl or $C_{3-7}$ heterocycloalkenyl group, optionally benzo fused and optionally including an oxygen atom or an additional nitrogen atom, and which may be optionally substituted by $C_{1-6}$ alkyl, hydroxy, $C_{1-4}$ alkoxy, $C_{2-6}$ alkoxycarbonyl, formyl, $(C_{6-10})ar(C_{1-4})alkyl$, $C_{6-10}$ aryl, pyridyl, hydroxyalkoxyalkyl, halogen, or $NR^{13}R^{14}$; or (B) $R^1$ is $C_{3-7}$ cycloalkyl or $C_{3-7}$ cycloalkenyl, either of which is optionally substituted by $C_{1-6}$ alkyl, hydroxy, $C_{1-4}$ alkoxy, halogen, carboxylic acid, a $C_{1-4}$ carboxylic acid ester group, or $NR^{13}R^{14}$, and $R^2$ is $C_{3-6}$ alkenyl, or $C_{3-6}$ alkynyl, either of which is optionally substituted by $C_{1-6}$ alkyl, hydroxy, $C_{1-4}$ alkoxy, halogen, carboxylic acid, a $C_{1-4}$ carboxylic acid ester group, or $NR^{13}R^{14}$; or (C) $R^1$ is $C_{3-7}$ heterocycloalkyl($C_{1-6}$)alkyl, $C_{3-7}$ heterocycloalkenyl($C_{1-6}$)alkyl, heteroaryl($C_{1-6}$)alkyl, $C_{3-7}$ heterocycloalkyl($C_{3-6}$)alkenyl, $C_{3-7}$ heterocycloalkenyl($C_{3-6}$)alkenyl, heteroaryl($C_{3-6}$) alkenyl, $C_{3-7}$ heterocycloalkyl($C_{3-6}$)alkynyl, $C_{3-7}$ heterocycloalkenyl($C_{1-6}$)alkynyl, heteroaryl($C_{3-4}$) alkynyl, di($C_{5-10}$ aryl)($C_{1-3}$)alkyl, di($C_{3-8}$ cycloalkyl)($C_{1-3}$)alkyl or di($C_{3-8}$ cycloalkenyl)($C_{1-3}$)alkyl, any of which is optionally substituted by $C_{1-6}$ alkyl, hydroxy, $C_{1-4}$ alkoxy, halogen, carboxylic acid, a $C_{1-4}$ carboxylic acid ester group, or $NR^{13}R^{14}$; and $R^2$ is a group

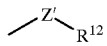

where $R^{12}$ and $Z'$ have the values and preferred values defined above;

$R^{13}$ and $R^{14}$ independently represent hydrogen, $C_{1-6}$alkyl, $C_{3-7}$cycloalkyl, $C_{2-6}$ alkenyl, $C_{2-6}$ alkynyl, $C_{6-10}$ aryl, $C_{6-10}$ ar($C_{1-4}$)alkyl, pyridyl, pyridyl($C_{1-4}$)alk carboxy($C_{1-6}$)-alkyl, $C_{1-4}$ alkoxycarbonyl($C_{1-4}$)alkyl, cyano($C_{2-6}$)alkyl. hydroxy($C_{2-6}$)alkyl, $C_{1-4}$ alkoxy($C_{2-6}$)alkyl, mono- and di-($C_{1-4}$)alkylamino($C_{2-6}$)alkyl;

or $R^{13}$ and $R^{14}$ form a $C_{3-7}$ heterocycloalkyl ring;

$R^3$ is hydrogen, $C_{1-3}$ alkyl, halogen or $C_{1-2}$ alkoxy;

$R^4$, $R^5$ and $R^6$ are hydrogen or halogen;

Y is —O—;

$R^a$, $R^b$ and $R^c$ are each one of hydrogen, $C_{1-4}$ alkyl, hydroxy, $C_{1-4}$ alkoxy. phenoxy, $C_{1-4}$ alkyloxycarbonyl, benzyloxycarbonyl, cyano,

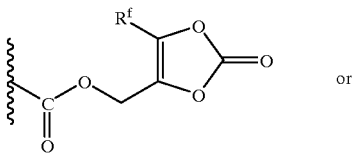

or

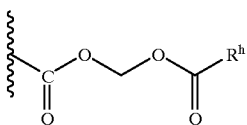

where $R^h$ is benzyl, methyl, ethyl, isopropyl, sec-butyl or t-butyl, and where $R^f$ is hydrogen or $C_{1-6}$ alkyl;

$R^{11}$ is one of hydrogen, $C_{1-6}$ alkyl, $C_{6-10}$ ar($C_{1-6}$)alkyl, $C_{6-10}$ aryl, $C_{2-10}$ hydroxyalkyl, $C_{2-10}$ aminoalkyl, mono($C_{1-4}$)alkylamino($C_{2-8}$)alkyl, di($C_{1-4}$)alkylamino($C_{2-8}$)alkyl or $C_{2-10}$ carboxyalkyl;

$R^7$, $R^8$, $R^9$ and $R^{10}$ are independently one of hydrogen, $C_{1-6}$ alkyl, $C_{2-10}$ carboxyalkyl or $C_{2-10}$ hydroxyalkyl, or $R^7$ and $R^8$ are taken together to form —(CH$_2$)$_y$— where y is zero, 1 or 2, while $R^9$ and $R^{10}$ are defined as above; or $R^7$ and $R^{10}$ are taken together to form —(CH$_2$)$_t$—, where t is zero (a bond), or 1, 2 or 3, while $R^8$ and $R^9$ are defined as above; or $R^8$ and $R^9$ are taken together to form —(CH$_2$)$_r$—, where r is 2, 3, or 4, while $R^7$ and $R^{10}$ are defined as above;

$R^{20}$ is hydrogen, or $C_{1-10}$ alkyl, optionally substituted with amino, mono($C_{1-4}$)alkylamino, $C_{1-6}$ aroxy, hydroxy, carboxy, phenyl, $C_{1-4}$ alkyloxycarbonyl, $C_{6-1}$ ar($C_{1-4}$)alkoxycarbonyl, $C_{1-6}$ acylamino, cyano or trifluoromethyl;

n is from zero to 4; and m is from zero to 4.

An especially preferred group of compounds include compounds of Formula Ia wherein:

$R^1$ is cyclopentyl cyclohexyl or cycloheptyl;

$R^2$ is allyl, diphenylmethyl or dicyclohexylmethyl;

$R^3$ is hydrogen, methyl, chloro or $C_1$–$C_2$ alkoxy;

$R^4$, $R^5$ and $R^6$ are hydrogen or halogen;

Y is —O—;

$R^a$, $R^b$ and $R^c$ are hydrogen, hydroxy,

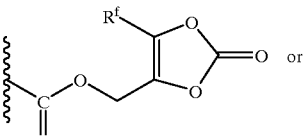

or

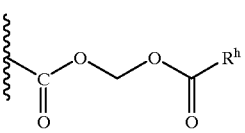

where $R^h$ is benzyl or t-butyl, and where $R^f$ is hydrogen or methyl;

$R^{11}$ is hydrogen, $C_{1-4}$ alkyl, $C_{2-4}$ hydroxyalkyl, $C_{2-4}$ carboxyalkyl, $C_{2-4}$ aminoalkyl, dimethylamino($C_{2-8}$)alkyl, or methylamino($C_{2-8}$)alkyl;

$R^7$, $R^8$, $R^9$ and $R^{10}$ are independently one of hydrogen, $C_{1-6}$ alkyl, $C_{2-10}$ hydroxyalkyl or $C_{2-10}$ carboxyalkyl, or $R^7$ and $R^8$ are taken together to form —(CH$_2$)$_y$— where y is zero, 1 or 2, while $R^9$ and $R^{10}$ are defined as above; or $R^7$ and $R^{10}$ are taken together to form —(CH$_2$)$_q$—, where q is zero (a bond), or 1, 2 or 3, while $R^8$ and $R^9$ are defined as above; or $R^8$ and $R^9$ are taken together to form —(CH$_2$)$_r$—, where r is 2, 3 or 4, while $R^7$ and $R^{10}$ are defined as above;

X is —O—;

n is from zero to 4; and m is zero, 1, 2 or 3.

An especially preferred subclass of the compounds of Formula I is defined by compounds of Formula IIa and IIb:

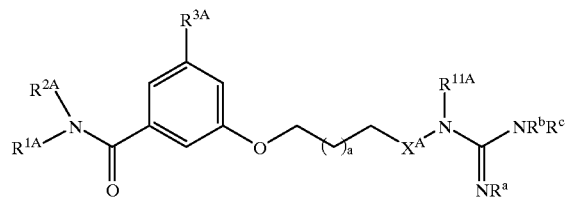

IIa

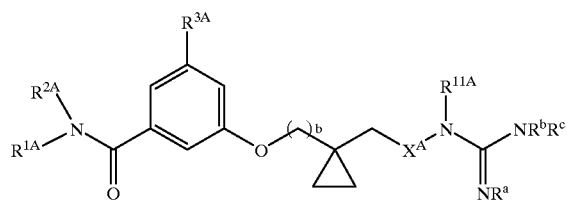

IIb or a solvate, hydrate, pharmaceutically acceptable salt or prodrug thereof, wherein:

$R^{1A}$ represents a group:

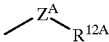

wherein $Z^A$ represents a bond or $C_{1-6}$ alkyl; and $R^{12A}$ represents hydrogen, $C_{3-7}$ cycloalkyl, $C_{1-6}$ alkoxy, aryl optionally substituted by halogen, hydroxy, heteroaryl, diphenylmethyl or dicyclohexylmethyl;

R$^{2A}$ represents a group:

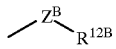

wherein Z$^B$ represents C$_{3-6}$ alkenyl or C$_{1-6}$ alkyl optionally substituted by CO$_2$R$^{15}$ or COR$^{15}$; R$^{12B}$ represents hydrogen, C$_{1-6}$, alkoxy, mono- or di- C$_{1-3}$ alkylamino, phenyl substituted by C$_2$R$^{15}$, oxadiazole substituted by a hydroxy group, or an unsubstituted C-linked tetrazole group; and R$^{15}$ is C$_{1-3}$ alkyl or mono- or di-hydroxyphenyl;

or R$^{1A}$ and R$^{2A}$ can be taken together with the nitrogen atom to which they are attached to form athree to seven membered ring, which optionally contains an additional nitrogen or oxygen atom, and which is optionally benzo or pyrido fused, said ring being preferably saturated, and said ring having one or two optional substituents on either a ring carbon or nitrogen selected from the group consisting of halogen, hydroxy, acyloxy, alkoxy, aryloxy, alkyl, cycloalkyl, alkenyl, alkynyl, aryl, aralkyl, heteroaryl, heteroar(C$_{1-4}$)alkyl, carboxyalkyl, alkoxycarbonylalkyl, hydroxyalkoxyalkyl, cyano(C$_{2-10}$)alkyl, hydroxy(C$_{2-10}$)alkyl, alkoxy(C$_{2-10}$)alkyl, alkoxyalkyl, mono- and di-alkylamino(C$_{2-10}$)alkyl, carboxy, alkoxycarbonyl, carboxamido, formyl, alkanoyl, aroyl, aralkanoyl, sulfonyl, alkylsulfonyl, alkoxysulfonyl, and NR$^{13}$R$^{14}$ (when C-substituted);

R$^{3A}$ represents C$_{1-3}$ alkyl or halogen, preferably chloro, bromo or methyl;

R$^{11A}$ represents hydrogen, C$_{6-10}$ ar(C$_{1-4}$)alkyl or C$_{1-4}$ alkyl;

R$^a$, R$^b$ and R$^c$ are hydrogen;

a is from zero to 8, preferably zero, 1, 2 or 3; and b is from zero to 8, preferably 1, 2 or 3.

An even more especially preferred group of compounds include compounds of Formula IIa wherein:

R$^{1A}$ represents a group:

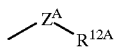

Z$^A$ represents a bond or C$_{1-6}$ alkyl; and R$^{12A}$ represents hydrogen, C$_{3-7}$ cycloalkyl, C$_{1-6}$ alkoxy, aryl optionally substituted by halogen or hydroxy, or heteroaryl;

R$^{2A}$ represents a group:

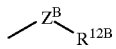

wherein Z$^B$ represents C$_{3-4}$ alkenyl or C$_{1-6}$ alkyl optionally substituted by CO$_2$R$^{15}$ or COR$^{15}$; R$^{12B}$ represents hydrogen, C$_{1-6}$ alkoxy, or mono- or di-C$_{1-3}$ alkylamino; and R$^{15}$ is C$_{1-3}$ alkyl or mono- or di-hydroxyphenyl;

or R$^{1A}$ and R$^{2A}$ are taken together with the nitrogen to which they are attached to form a C$_{3-7}$ heterocycloalkyl or C$_{3-7}$ heterocycloalkenyl group, optionally benzo fused and optionally including an oxygen atom or an additional nitrogen atom, and which may be optionally substituted by C$_{1-6}$ alkyl, hydroxy, C$_{1-4}$ alkoxy, C$_{2-6}$ alkoxycarbonyl, formyl, (C$_{6-10}$)ar(C$_{1-4}$)alkyl, C$_{6-10}$ aryl, pyridyl, hydroxy(C$_{1-4}$)alkoxy(C$_{1-4}$)alkyl, halogen, or NR$^{13}$R$^4$, where R$^{13}$ and R$^{14}$ are as defined above;

R$^{3A}$ represents halogen, preferably chloro;

X$^A$ is —O—;

R$^{11A}$ is hydrogen, C$_{6-10}$ ar(C$_{1-4}$)alkyl or C$_{1-4}$ alkyl;

R$^a$, R$^b$ and R$^c$ are hydrogen; and a is 1.

Non-limiting examples of compounds of the present invention include [3-{5-chloro-3-(N-cyclopentyl-N-[prop-2-enyl]aminocarbonyl)phenoxy}propoxyamino]carboxamidine hydrochloride, [3-{5-chloro-3-(4-benzylpiperidinylcarbonyl)phenoxy}propoxyamino]carboxamidine trifluoroacetate, [3-{5-chloro-3-(N,N-bis[2-methoxyethyl]aminocarbonyl)phenoxy}propoxyamino]carboxamidine trifluoroacetate, [3-{5-chloro-3-(N-methyl-N-[2-{2-pyridyl}ethyl]aminocarbonyl)phenoxy}propoxyamino]carboxamidine trifluoroacetate, [3-{5-chloro-3-(N-methyl-N-[3-pyridylmethyl]aminocarbonyl)phenoxy}propoxyamino]carboxamidine trifluoroacetate, [3-{5-chloro-3-(N-ethyl-N-[4-pyridylmethyl]aminocarbonyl)phenoxy}propoxyamino]carboxamidine trifluoroacetate, ethyl 2-[5-{3-(amidinoaminooxy)propoxy}-3-chlorophenyl]-N-{2-pyridylmethyl}aminocarbonyl]acetate trifluoroacetate, methyl 2-[5-{3-(amidinoaminooxy)propoxy}-3-chlorophenyl]-N-{2-pyridylmethyl}aminocarbonyl]acetate trifluoroacetate, [3-{5-chloro-3-([2-{3,4-dihydroxyphenyl}-2-oxoethyl]-N-methylaminocarbonyl)phenoxy}propoxyamino]carboxamidine trifluoroacetate, [3-{5-chloro-3-(N-[2-{dimethylamino}ethyl]-N-ethylaminocarbonyl)phenoxy}propoxyamino]carboxamidine trifluoroacetate, [3-{5-chlor-3-(4-formylpiperazinylcarbonyl)phenoxy}propoxyamino]carboxamidine trifluoroacetate, [3-{5-chloro-3-(4-phenylpiperazinylcarbonyl)phenoxy}propoxyamino]carboxamidine trifluoroacetate, [3-{5-chloro-3-(4-benzylpiperazinylcarbonyl)phenoxy}propoxyamino]carboxamidine trifluoroacetate, [3-{5-chloro-3-(N,N-dimethylaminocarbonyl)phenoxy}propoxyamino]carboxamidine trifluoroacetate, [3-{5-chloro-3-(piperidinylcarbonyl)phenoxy}propoxyamino]carboxamidine trifluoroacetate, [3-{5-chloro-3-(4-[2-pyridyl]piperazinylcarbonyl)phenoxy}propoxyamino]carboxamidine trifluoroacetate, [3-{5-chloro-3-(4-[4-pyridyl]piperazinylcarbonyl)phenoxy}propoxyamino]carboxamidine trifluoroacetate, [3-{5-chloro-3-(2-[1,2,3,4-tetrahydro]isoquinolinylcarbonyl)phenoxy}propoxyamino]carboxamidine trifluoroacetate, [3-{5-chloro-3-(azaperhydroepinylcarbonyl)phenoxy}propoxyamino]carboxamidine trifluoroacetate, ethyl 3-({5-[3-(amidinoaminooxy)propoxy]-3-chlorophenyl}-N-benzylcarbonylamino)propanoate trifluoroacetate, ethyl 1-({5-[3-(amidinoaminooxy)propoxy]-3-chlorophenyl}carbonyl)piperidine-4-carboxylate trifluoroacetate, [3-{5-chloro-3-(morpholin-4-ylcarbonyl)phenoxy}propoxyamino]carboxamidine trifluoroacetate, and methyl 2-({5-[3-(amidinoaminooxy)propoxy]-3-chlorophenyl}-N-methylcarbonylamino)acetate trifluoroacetate.

Alternative embodiments of the present invention include compounds of Formula I in which two "R" groups together form a saturated or unsaturated hydrocarbon bridge, thus forming an additional cyclic moiety in the resulting compounds. Alternative embodiments include compounds of Formula I wherein Z, R$^1$–R$^4$, Y, m and n are as defined above; and:

A. R$^7$ and R$^{10}$ are taken together to form —(CH$_2$)$_o$—, where o is 1, 2 or 3;

R⁹ is hydrogen, alkyl, aralkyl, aryl, hydroxyalkyl or carboxyalkyl;

R⁸ is hydrogen and R¹¹, Rᵃ, Rᵇ and Rᶜ are defined as above; or

B. R⁹ is hydrogen, alkyl, aralkyl, aryl, hydroxyalkyl or carboxyalkyl;

R⁷ is hydrogen;

R⁸ and R¹⁰ are taken together to form —(CH₂)—(CH₂)—(CH₂)ₚ—, where p is 1, 2 or 3; and R¹¹, Rᵃ, Rᵇ and Rᶜ are defined as above; or C. R¹¹ and Rᵇ are taken together to form —(CH₂)—(CH₂)ᵣ— or =CH—N=CH—NH—, where r is 1, 2 or 3;

Rᵃ is hydrogen or hydroxy;

Rᶜ is hydrogen, alkyl, hydroxy, alkoxy, aryloxy, aralkoxy, alkoxycarbamoyloxy, cyano or —CO₂Rʷ—, where Rʷ is as defined above;

R⁷, R⁸, R⁹ and R¹⁰ are each independently one of hydrogen, alky, aralkyl, aryl, hydroxyalkyl or carboxyalkyl, or R⁷ and R⁸ are taken together to form —(CH₂)ᵧ—, where y is zero, 1 or 2; or Dᵃ and Rᶜ are taken together to form —CH₂—(CH₂)ₛ—, where s is 1 or 2;

R¹¹ is hydrogen, alkyl, alkoxy, aryloxy, aralkoxy, alkoxycarbonyloxy, cyano or —CO₂Rʷ—, where Rʷ is as defined above; and R⁷, R⁸, R⁹ and R¹⁰ are each independently one of hydrogen, alkyl, aralkyl, aryl, hyhrocyalkyl or carboxyalkyl, or R⁷ and R⁸ are taken together to form —(CH₂)ᵧ—, where y is zero, 1 or 2.

Thus, compounds having Formulae III, IV, V and VI (representing embodiments A, B, C and D, respectively) are contemplated:

III

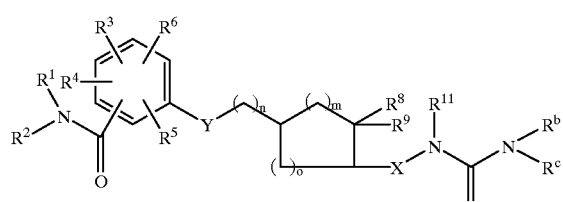

IV

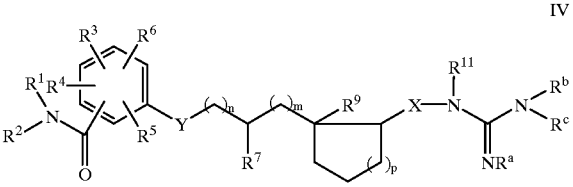

IV

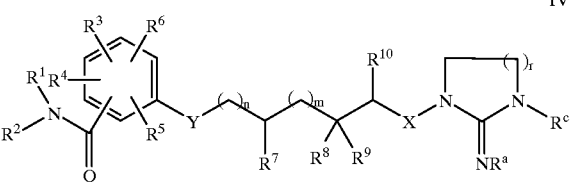

-continued

VI

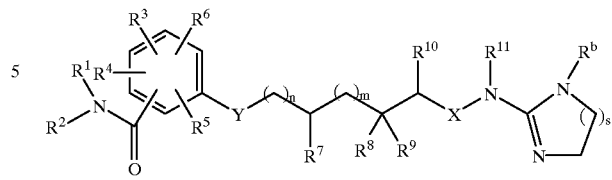

wherein R¹–R¹¹, Z, Y, Rᵃ–Rᶜ, n, m, o, p, r and s are defined as above. Preferred values for each of these variables are the same as described for Formula I It is also to be understood that the present invention is considered to include stereoisomers as well as optical isomers, e.g. mixtures of enantiomers as well as individual enantiomers and diastereomers, which arise as a consequence of structural asymmetry in selected compounds of the present series.

The compounds of Formula I may also be solvated, especially hydrated. Hydration may occur during manufacturing of the compounds or compositions comprising the compounds, or the hydration may occur over time due to the hygroscopic nature of the compounds.

Certain compounds within the scope of Formula I are derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process; see Notari, R. E., "Theory and Practice of Prodrug Kinetics," *Methods in Enzymology*, 112:309–323 (1985); Bodor, N., "Novel Approaches in Prodrug Design," *Drugs of the Future*, 6(3):165–182 (1981); and Bundgaard, H., "Design of Prodrugs: Bioreversible-Derivatives for Various Functional Groups and Chemical Entities," in *Design of Prodrugs* (H. Bundgaard, ed.), Elsevier, New York (1985). Useful prodrugs are those where Rᵃ, Rᵇ and/or Rᶜ are —CO₂Rʷ, where Rʷ is defined above. See, U.S. Pat. No. 5,466,811 and Saulnier et al., *Bioorg. Med. Chem. Lett.* 4:1985–1990 (1994).

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl.

The term "alkenyl" is used herein to mean a straight or branched chain radical of 2–20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkynyl" is used herein to mean a straight or branched chain radical of 2–20 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 10 carbon atoms in length, more preferably, 2 to 8 carbon atoms in length, most preferably from 2 to 4 carbon atoms in length.

In all instances herein where there is an alkenyl or alkynyl moiety as a substituent group, the unsaturated linkage, i.e., the vinylene or acetylene linkage is preferably not directly attached to a nitrogen, oxygen or sulfur moiety.

The term "alkoxy" is used herein to mean a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to $C_{1-6}$alkyl groups as discussed above having an aryl substituent, such as benzyl, phenylethyl or 2-naphthylmethyl.

The term "cycloalkyl" as employed herein by itself or as part of another group refers to cycloalkyl groups containing 3 to 9 carbon atoms. Typical examples are cyclopropyl, cyclobutyl, cyclopentyl, cyclohexyl, cycloheptyl, cyclooctyl and cyclononyl.

The terms "alkoxy" refers to any of the above alkyl groups linked to an oxygen atom.

The term "halogen" or "halo" as employed herein by itself or as part of another group refers to chlorine, bromine, fluorine or iodine with chlorine being preferred.

The term "monoalkylamine" as employed herein by itself or as part of another group refers to an amino group which is substituted with one alkyl group having from 1 to 6 carbon atoms.

The term "dialkylamine" as employed herein by itself or as part of another group refers to an amino group which is substituted with two alkyl groups, each having from 1 to 6 carbon atoms The term "hydroxyalkyl" as employed herein refers to any of the above alkyl groups substituted by one or more hydroxyl moieties.

The term "carboxyalkyl" as employed herein refers to any of the above alkyl groups substituted by one or more carboxylic acid moieties.

The term "heterocyclic" is used herein to mean a saturated or wholly or partially unsaturated 3–7 membered monocyclic, or 7–10 membered bicyclic ring system, which consists of carbon atoms and from one to four heteroatoms independently selected from the group consisting of O, N, and S, wherein the nitrogen and sulfur heteroatonis can be optionally oxidized, the nitrogen can be optionally quaternized, and including any bicyclic group in which any of the above-defmed heterocyclic rings is fused to a benzene ring, and wherein the heterocyclic ring can be substituted on carbon or on a nitrogen atom if the resulting compound is stable. Especially useful are rings containing one oxygen or sulfur, one to three nitrogen atoms, or one oxygen or sulfur combined with one or two nitrogen atoms. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, tetrahydroisoquinolinyl, benzimidazolyl, thiadiazoyl, benzopyranyl, benzothiazolyl, benzoxazolyl, furyl, tetrahydrofiuryl, tetrahydropyranyl. thienyl, benzothienyl, thiamorpholinyl, thiamorpholinyl sulfoxide, thiamorpholinyl sulfone, and oxadiazolyl. Morpholino is the same as morpholinyl.

The term "heteroatom" is used herein to mean an oxygen atom ("O"), a sulfur atom ("S") or a nitrogen atom ("N"). It will be recognized that when the heteroatom is nitrogen, it may form an $NR^yR^z$ moiety, wherein $R^y$ and $R^z$ are, independently from one another, hydrogen or $C_1$ to $C_8$ alkyl, or together with the nitrogen to which they are bound, form a saturated or unsaturated 5-, 6-, or 7-membered ring.

The term "heteroaryl" includes 5 or 6 membered aromatic heterocyclic rings containing one or more heteroatoms selected from nitrogen, sulphur and oxygen atoms, and fused bicyclic ring systems containing one or more nitrogen, sulfur, and oxygen atoms. Examples of such groups include oxadiazole, thiazole thiadiazole, triazole, tetrazole, benzimidazole, pyridine, fliran and thiophene.

A $C_{3-7}$ cycloalkenyl group includes rings containing at least one double bond incorporated in the ring.

A $C_{3-7}$ heterocycloalkyi group includes rings containing one or more heteroatoms selected from nitrogen, sulphur and oxygen atoms, for example, a tetrahydropyran-4-yl group.

A $C_{3-7}$ heterocycloalkenyl group includes rings containing one or more heteroatoms selected from nitrogen, sulphur and oxygen atoms, together with at least on double bond incorporated in the ring.

Another aspect of the present invention is a process for preparing an aminoguanidine compound of Formula I, comprising reacting an aminoguanidine of the formula:

VII

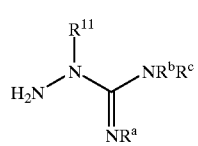

wherein $R^{11}$, $R^a$, $R^b$ and $R^c$ are defined as above, with a carbonyl-containing compound of the formula:

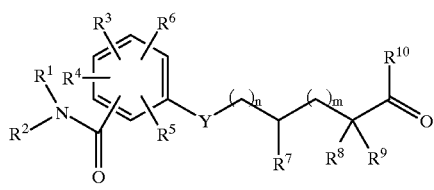

VIII

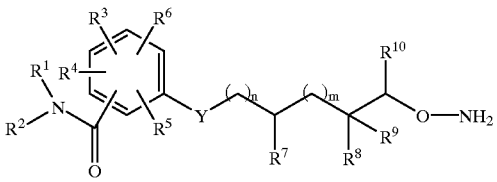

IX wherein $R^1$–$R^6$, Y, n, m, $R^7$, $R^8$, $R^9$ and $R^{10}$ are defined as above to form an amidinohydrazone, and thereafter selectively reducing the hydrazone carbon to nitrogen double bond of the amidinohydrazone.

The aminoguanidine is typically provided as a salt, preferably the nitrate salt. The first step proceeds at ambient temperature using alcohol as a solvent. An acid, such as 4N HCl in dioxane is added to the reaction mixture.

Another aspect of the present invention is a process for preparing a hydroxyguanidine compound of Formula I, comprising reacting an alkoxyamine compound of the formula:

wherein $R^1$–$R^6$, Y, n, m, $R^7$, $R^8$, $R^9$ and $R^{10}$ are defined as above with a guanidinylating reagent. Preferred guanidinylating reagents include: aminoiminosulfonic acid, optionally substituted 1H-pyrazole-1-carboxamidines, or N,N'-bis(tert-butoxycarbonyl) S-methyl isothiourea.

Schemes 1a, 1b and 1c exemplify the synthetic steps to produce compounds of the present invention.

Scheme 1a

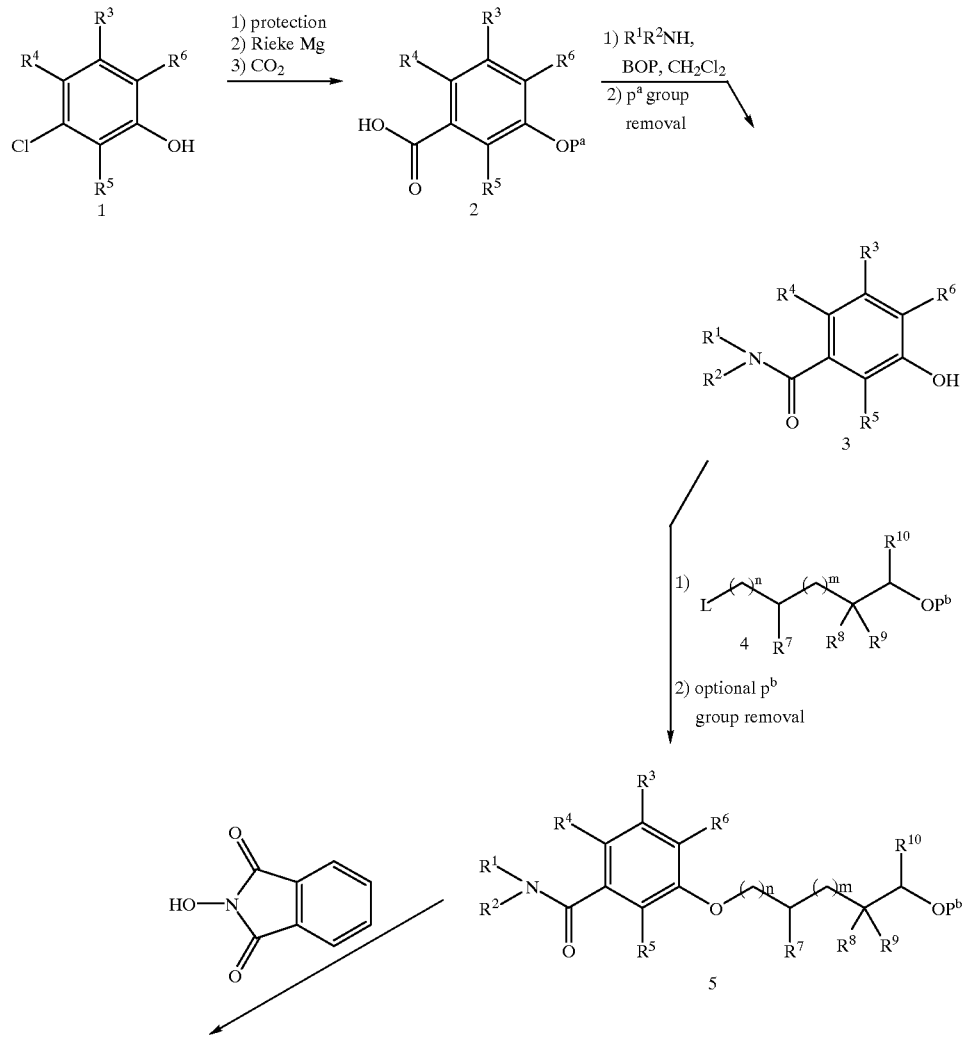

-continued
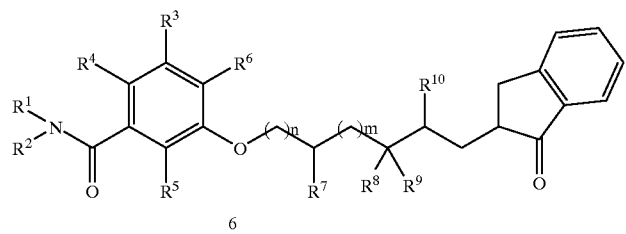
6
1) deprotection
2) guanidinylation
3) optional $R^a, R^b$ and $R^c$ removal
4) optional alkylation
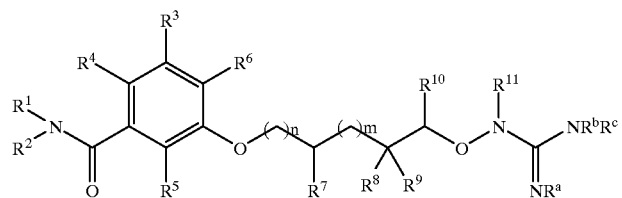
7
Scheme 1b
1)
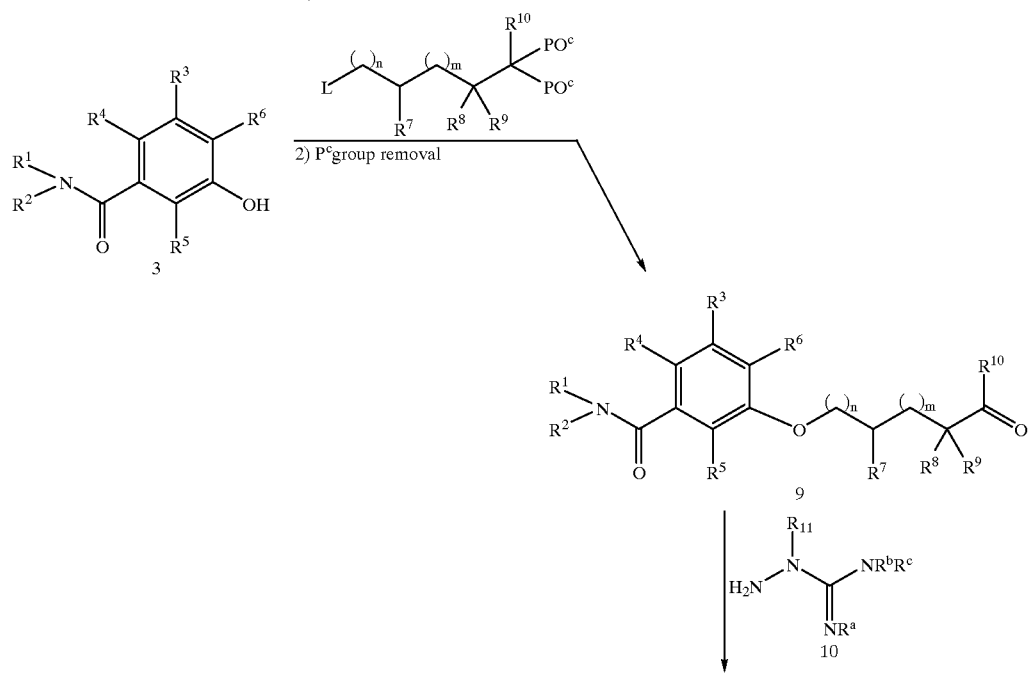
2) $P^c$ group removal -continued

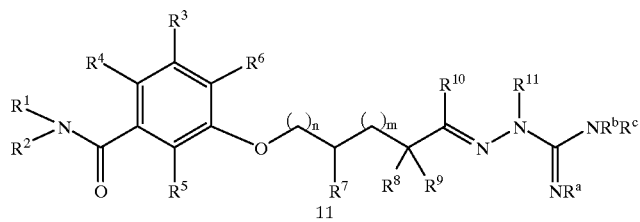

1) reduction
2) optional $R^a, R^b, R^c$ removal

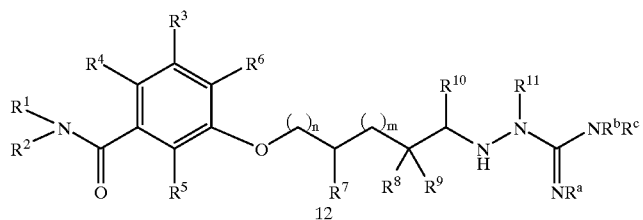

12

Halogenated phenols 1 may be monoprotected ($P^a$ is a protecting group) with a variety of protecting groups known in the art, such as esters and benzyl ethers (Greene, T. W. and Wuts, P. G. M., *Protective Groups in Organic Synthesis*, 2nd edition, John Wiley and Sons, Inc. New York (1991)). Deprotection of the hydroxy groups is routinely accomplished using the reaction conditions well known in the art. For example, deprotection of benzyl ethers may be effected through catalytic hydrogenation using palladium on carbon as a catalyst in solvents such as ethanol or tetrahydrofuran. Deprotection of an acetate is accomplished by basic hydrolysis, most preferably with sodium hydroxide in aqueous tetrahydrofuran.

Additional compounds of the invention are formed by employing phenols that are halogenated ortho- orpara- to the hydroxy groups in place of the meta-halogenated phenols 1.

Halogenated phenols 1 are carboxylated to form phenolic carboxylic acids 2, which are then reacted with suitable amines to form phenolic amides 3. Phenolic amides 3 are coupled to 4 (for L=OH) using a Mitsunobu coupling procedure (Mitsunobu, O., *Synthesis* 1 (1981)), where $P^b$ of 4 may be a suitable alcohol protecting group. Alternatively, suitable diols ($P^b$=H) may be used in the Mitsunobu reaction. Preferred coupling conditions include using a trialkylphosphine or triarylphosphine, such as triphenylphosphine or tri-n-butylphosphine, in a suitable solvent, such as tetrahydrofuran or dichloromethane, and an azodicarbonyl reagent, such as diethyl azodicarboxylate or 1,1'-(azodicarbonyl)dipiperidine. Typical $P^b$ (where $P^b$ is an alcohol protecting group) is well known in the art, such as esters and benzyl ethers (Greene, T. W. and Wuts, P. G. M., supra). Alternatively, where L is a reactive leaving group such as halide or sulfonate, phenol 3 may be treated with a base, such as sodium hydride, in a solvent, such as N,N-dimethylformarnide, and then treated with 4. Removal of $P^b$ is routinely accomplished using the reaction conditions well known in the art. For example, deprotection of benzyl ethers may be effected through catalytic hydrogenation using palladium on carbon as a catalyst in solvents such as ethanol or tetrahydrofuran. Deprotection of an acetate is accomplished by basic hydrolysis, most preferably with sodium hydroxide in aqueous tetrahydrofuiran.

Alcohol 5 is converted to 6 employing a Mitsunobu reaction with an N-hydroxycyclic imide derivative such as N-hydroxyphthalimide. Unveiling of the phthalimide protecting group is accomplished using standard conditions well known in the art (Greene, T. W. and Wuts, P. G. M., supra), for example, sodium borohydride in a mixture of an appropriate alcohol (e.g. ethanol or 2-propanol)/water followed by acidification. Alternatively, removal of the protecting group may be accomplished using hydrazine or methylamine.

Guanidinylation of the resulting alkoxyamine to 7 is achieved using standard reagents such as aminoiminosulfonic acid (Miller, A. E. and Bischoff, J. J. *Synthesis* 777 (1986)), or 1H-pyrazole-1-carboxamidine hydrochloride (Bernatowicz, M. S. et. al. *J. Org. Chem* 57(8):2497 (1992)), or with substituted guanidinylating reagents such as N,N'-bis(tert-butoxycarbonyl)-S-methylisothiourea (Bergeron, R. J. and McManis, J. S. *J. Org. Chem.* 52:1700 (1987)) or N—$R^a$, N—$R^b$, N'-$R^c$-1H-pyrazole-1-carboxamidine, where $R^a$, $R^b$ and $R^c$ are defined as above for Formula I. Useful 1H-pyrazole-1-carboxamidines include N,N'-bis(tert-butoxycarbonyl)-1H-pyrazole-1-carboxamidine and N,N'-bis(benzyloxycarbonyl)-1H-pyrazole-1-carboxamidine (all ofwhich can be pepared according to Bernatowicz, M. S. et. al., *Tetrahedron Letters* 34:3389 (1993)).

Alkoxyguanidines (where $R^{11}$ is H) may be optionally alkylated using such reagents as alkyl bromides, and bases such as sodium bicarbonate, in a solvent such as N,N-dimethylformamide to form compounds where $R^{11}$ is alkyl.

Scheme 1b describes an alternative synthesis for forming compounds where X is NH. Phenolic amide 3 may be converted to 9 by the Mitsunobu reaction using 8 wherein L=OH and the $P^c$'s are alkyl groups or are combined to form a cycloalkyl or cycloalkenyl group. Alternatively, where L of 8 is a reactive leaving group such as halide or sulfonate, phenol 3 may be treated with a base, such as sodium hydride in a solvent such as N,N-dimethylformamide, and then treated with 8. Protecting groups, $P^c$, may then be removed to afford 9 using standard conditions well known in the art, for example, p-toluenesulfonic acid in acetone (Greene, T. W. and Wuts, P. G. M., supra).

Compound 9 is then converted to amidinohydrazone 11 using standard conditions, for example, treatment with an aminoguanidine, such as aminoguanidine or 2-hydrazinoimidazoline, optionally in the presence of an acid such as nitric acid, hydrogen chloride, or hydrogen bromide, in an appropriate solvent, for example, ethanol or methanol, which, in addition, may contain other solvents such as dichloromethane or tetrahydrofuran. Conversion of 11 to 12 is accomplished under reducing conditions well known in the art, for example, lithium borohydride in an appropriate solvent such as tetrahydrofuran or methanol at various temperatures up to reflux. As an alternative method, catalytic hydrogenation with palladium on carbon catalyst can be employed.

When $R^a$, $R^b$ and/or $R^c$ are a protecting group, for example tert-butyloxycarbonyl (Boc), these protecting groups can be optionally removed by treatment with acid, usually trifluoroacetic acid in a suitable solvent such as dichloromethane or water, or by HCl gas dissolved in a suitable solvent. such as 1,4-dioxane.

Scheme 1c describes an alternative synthesis that can be used to generate libraries of compounds 7 in parallel. Carboxylic acid 2 may be protected with a protecting group ($P^c$), such as a benzyl ester, and the $P^a$ group (described above) removed with a reagent, such as tetrabutylammonium fluoride, both well known in the art (Green, T. W., and Wuts, P. G. M., supra) giving phenol 33. Phenol 33, where L is a reactive leaving group such as halide or sulfonate, can then be treated with a base, such as cesium carbonate, in a solvent, such as acetonitrile, and reacted with 4. The $P^b$ group may then be removed as above to form alcohol 34, which can be converted to 35 employing a Mitsunobu reaction with an N-hydroxycyclic imide derivative such as N-hydroxyphthalimide. The phthalimide protecting group can be removed and the resulting alkoxyamine can be guanidinylated as above, and the $P^c$ group (e.g., benzyl ester) may then be removed to afford 36 using standard conditions well known in the art, for example, aqueous sodium hydroxide in ethanol (Greene, T. W., and Wuts, P. G. M., supra). Carboxylic acid 36 can then be coupled to a variety of different amines and purified in a parallel format giving a library of compounds 7.

As an alternative scheme to produce the O-phthalamide-containing intermediates 6, the respective phenolic amides 3 may be reacted under basic conditions with reagent 23 which contains a leaving group L' (Scheme 2). This scheme is limited to producing compounds where $R^{10}$ is hydrogen. Reagent 23 is produced by reacting a compound (22) having two leaving groups, L and L', under basic conditions with N-hydroxyphthalimide (Khadilkar and Samant, *Indian J. Chem. Sec.* B 1137 (1993)).

Compounds wherein $R^7$ and $R^{10}$ (III) or $R^8$ and $R^{10}$ (IV) together form a methylene linkage can be synthesized by substituting a cyclic ketone hasting a reactive group L that is attached directly or indirectly to the carbocyclic ring. Examples of suitable reagents include 2-hydroxycyclopentanone, 3-hydroxycyclopentanone, 2-hydroxycyclohexanone and 3-hydroxycyclohexanone.

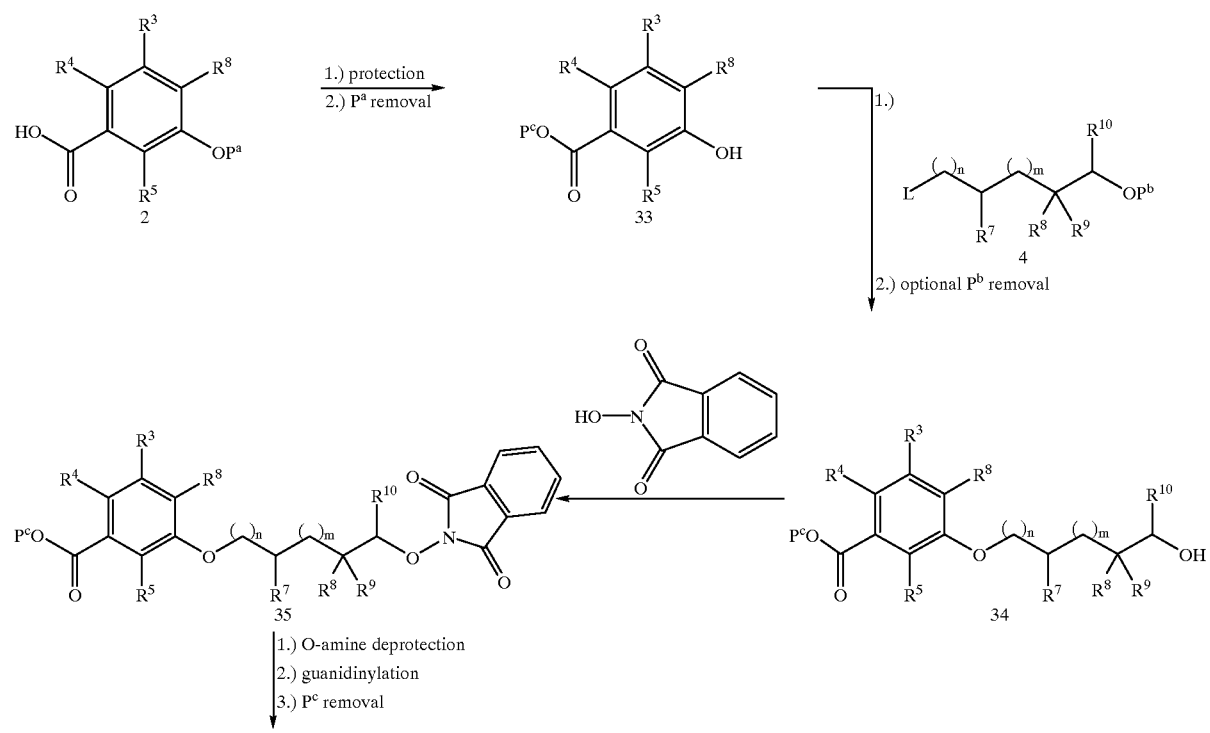

Scheme 1c

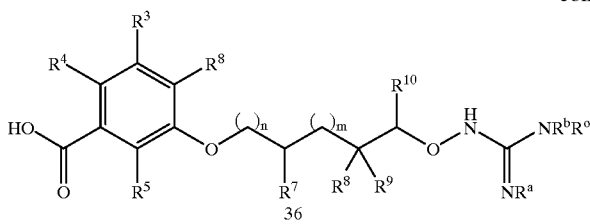

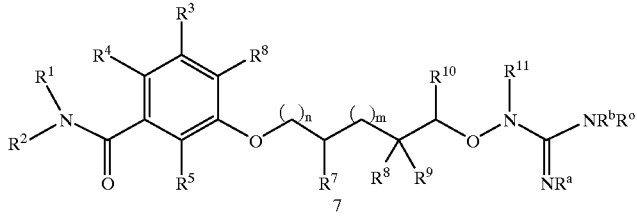

1.) $R^1R^2NH$, base
2.) optional $R^a$, $R^b$, $R^o$ Removal
3.) optional alkylation

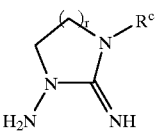

X

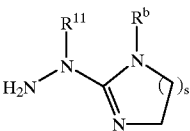

XI

Scheme 2

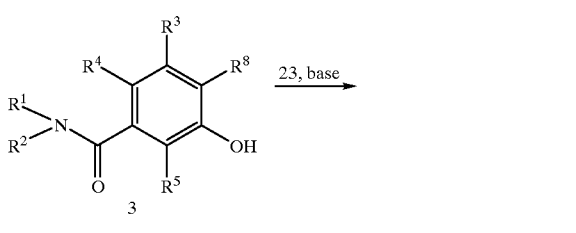

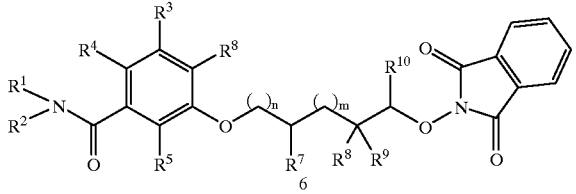

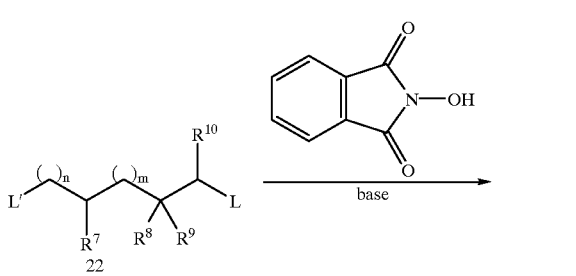

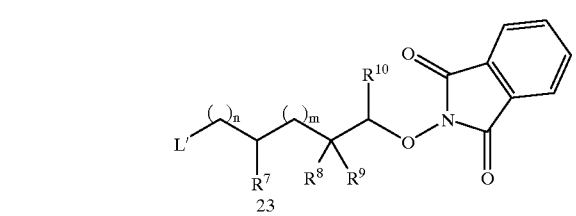

Compounds VI wherein $R^{11}$ and $R^b$ are taken together with the nitrogens to which they are attached to form a ring structure are prepared by substituting a heterocyclic amine X (below) for the aminoguanidine in the above Schemes.

Compounds V wherein $R^a$ and $R^c$ are taken together with the nitrogen atoms to which they are attached to form an imidazoline moiety are prepared by substituting a 2-hydrazinoimidazoline XI (above) for the aminoguanidines in the above Schemes.

For medicinal use, the pharmaceutically acceptable acid addition salts, those salts in which the anion does not contribute significantly to toxicity or pharmacological activity of the organic cation, are preferred. The acid addition salts are obtained either by reaction of an organic base of Formula I with an organic or inorganic acid, preferably by contact in solution, or by any of the standard methods detailed in the literature available to any practitioner skilled in the art. Examples of useful organic acids are carboxylic acids such as maleic acid, acetic acid, tartaric acid, propionic acid, fumaric acid, isethionic acid, succinic acid, cyclamic acid, pivalic acid and the like; useful inorganic acids are hydrohalide acids such as HCl, HBr, HI; sulfuric acid; phosphoric acid and the like. Preferred acids for forming acid addition salts include HCl and acetic acid.

The compounds of the present invention represent a novel class of potent inhibitors of metallo, acid, thiol and serine proteases. Examples of the serine proteases inhibited by compounds within the scope of the invention include leukocyte neutrophil elastase, aproteolytic enzyme implicated in the pathogenesis of emphysema; chymotrypsin and trypsin, digestive enzymes; pancreatic elastase, and cathepsin G, a chymotrypsin-like protease also associated with leukocytes; thrombin and factor Xa, proteolytic enzymes in the blood coagulation pathway. Inhibition of thermolysin, a metalloprotease, and pepsin, an acid protease, are also contemplated uses of compounds of the present invention. The compounds of the present invention are preferably employed to inhibit trypsin-like proteases.

An end use application of the compounds that inhibit chymotrypsin and trypsin is in the treatment of pancreatitis. For their end-use application, the potency and other biochemical parameters of the enzyme-inhibiting characteristics of the compounds of the present invention is readily ascertained by standard biochemical techniques well known in the art. Actual dose ranges for their specific end-use application will, of course, depend upon the nature and severity of the disease state of the patient or animal to be treated, as determined by the attending diagnostician. It is expected that a useful dose range will be about 0.01 to 10 mg per kg per day for an effective therapeutic effect.

Compounds of the present invention that are distinguished by their ability to inhibit either factor Xa or thrombin may be employed for a number of therapeutic purposes. As factor Xa or thrombin inhibitors, compounds of the present invention inhibit thrombin production. Therefore, these compounds are useful for the treatment or prophylaxis of states characterized by abnormal venous or arterial thrombosis involving either thrombin production or action. These states include, but are not limited to, deep vein thrombosis; disseminated intravascular coagulopathy which occurs during septic shock, viral infections and cancer; myocardial infarction; stroke; coronary artery bypass; fibrin formation in the eye; hip replacement; and thrombus formation resulting from either thrombolytic therapy or percutaneous transluminal coronary angioplasty (PCTA).

Other uses include the use of said thrombin inhibitors as anticoagulants either embedded in or physically linked to materials used in the manufacture of devices used in blood collection, blood circulation, and blood storage, such as catheters, blood dialysis machines, blood collection syringes and tubes, blood lines and stents. The compounds of the present invention may also be used as an anticoagulant in extracorporeal blood circuits.

Metal stents have been shown to reduce restenosis, but are thrombogenic. A strategy for reducing the thrombogenicity of stents is to coat, embed, adsord or covalently attach a thrombin-inhibiting agent to the stent surface. The compounds of the present invention can be employed for this purpose. Compounds of the invention can be attached to, or embedded within soluble and/or biodegradeable polymers as and thereafter coated onto stent materials. Such polymers can include polyvinylpyrrolidone, polyhydroxy-propyl-methacrylamide-phenol, polyhydroxyethyl-aspartamide-phenol, or polyethyleneoxide-polylysine substituted with palmitoyl residues, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. See European Application 761 251, European Application 604,022, Canadian Patent 2,164,684 and PCT Published Applications WO 96/11668, WO 96/32143 and WO 96/38136.

By virtue of the effects of both factor Xa and thrombin on a host of cell types, such as smooth muscle cells, endothelial cells and neutrophils, the compounds of the present invention find additional use in the treatment or prophylaxis of adult respiratory distress syndrome; inflammatory responses; wound healing; reperfusion damage; atherosclerosis; and restenosis following an injury such as balloon angioplasty, atherectomy, and arterial stentplacement. The compounds of the present invention may be useful in treating neoplasia and metastasis as well as neurodegenerative diseases, such as Alzheimer's disease and Parkinson's disease.

When employed as thrombin or factor Xa inhibitors, the compounds of the present invention may be administered in an effective amount within the dosage range of about 0.1 to about 500 mg/kg, preferably between 0.1 to 10 mg/kg body weight, on a regimen in single or 2–4 divided daily doses.

When employed as inhibitors of thrombin, the compounds of the present invention may be used in combination with thrombolytic agents such as tissue plasminogen activator, streptokinase, and urokinase. Additionally, the compounds of the present invention may be used in combination with other antithrombotic or anticoagulant drugs such as, but not limited to, fibrinogen antagonists and thromboxane receptor antagonists.

Human leucocyte elastase is released by polymorphonuclear leukocytes at sites of inflammation and thus is a contributing cause for a number of disease states. Compounds of the present invention are expected to have an anti-inflammatory effect usefuil in the treatment ofgout, rheumatoid arthritis and other inflammatory diseases, and in the treatment of emphysema. The leucocyte elastase inhibitory properties of compounds of the present invention are determined by the method described below. Cathepsin G has also been implicated in the disease states of arthritis, gout and emphysema, and in addition, glomerulonephritis and lung infestations caused by infections in the lung. In their end-use application the enzyme inhibitory properties of the compounds of Formula I is readily ascertained by standard biochemical techniques that are well-known in the art.

The Cathepsin G inhibitory properties of compounds within the scope of the present invention are determined by the following method. A preparation of partially purified human Cathepsin G is obtained by the procedure of Baugh et al., *Biochemistry* 15: 836 (1979). Leukocyte granules are a major source for the preparation of leukocyte elastase and cathepsin G (chymotrypsin-like activity). Leukocytes are lysed and granules are isolated. The leukocyte granules are extracted with 0.20 M sodium acetate, pH 4.0, and extracts are dialyzed against 0.05 M Tris buffer, pH 8.0 containing 0.05 M NaCl overnight at 4° C. A protein fraction precipitates during dialysis and is isolated by centrifugation. This fraction contains most of the chymotrypsin-like activity of leukocyte granules. Specific substrates are prepared for each ernzme, namely N-Suc-Ala-Ala-Pro-Val-p-nitroanilide and Suc-Ala-Ala-Pro-Phe-p-nitroanilide. The latter is not hydrolyzed by leukocyte elastase. Enzyme preparations are assayed in 2.00 mL of 0.10 M Hepes buffer, pH 7.5, containing 0.50 MNaCl, 10% dimethylsulfoxide and 0.0020 M Suc-Ala-Ala-Pro-Phe-p-nitroanilide as a substrate. Hydrolysis of the p-nitroanilide substrate is monitored at 405 nm and at 25° C.

Useful dose range for the application of compounds of the present invention as neutrophil elastase inhibitors and as Cathepsin G inhibitors depend upon the nature and severity of the disease state, as determined by the attending diagnostician, with a range of 0.01 to 10 mg/kg body weight, per day, being useful for the aforementioned disease states.

Compounds of the present invention that inhibit urokinase or plasminogen activator are potentially useful in treating excessive cell growth disease state. As such compounds of the present invention may also be useful in the treatment of benign prostatic hypertrophy and prostatic carcinoma, the treatment of psoriasis, and as abortifacients. For their end-use application, the potency and other biochemical parameters of the enzyme inhibiting characteristics of compounds of the present invention are readily ascertained by standard biochemical techniques well known in the art. Actual dose ranges for this application will depend upon the nature and severity of the disease state of the patient or animal to be treated as determined by the attending diagnostician. It is to be expected that a general dose range will be about 0.01 to 10 mg per kg per day for an effective therapeutic effect.

Additional uses for compounds of the present invention include analysis of commercial reagent enzymes for active site concentration. For example, chymotrypsin is supplied as a standard reagent for use in clinical quantitation of chymotrypsin activity in pancreatic juices and feces. Such assays are diagnostic for gastrointestinal and pancreatic disorders. Pancreatic elastase is also supplied commercially as a reagent for quantitation of al-antitrypsin in plasma. Plasma $\alpha_1$-antitrypsin increases in concentration during the course of several inflammatory diseases, and $\alpha_1$-antitrypsin deficiencies are associated with increased incidence of lung disease. Compounds of the present invention can be used to enhance the accuracy and reproducibility of these assays by titrametric standardization of the commercial elastase supplied as a reagent. See, U.S. Pat. No. 4,499,082.

Protease activity in certain protein extracts during purification of particular proteins is a recurring problem which can complicate and compromise the results of protein isolation procedures. Certain proteases present in such extracts can be inhibited during purification steps by compounds of the present invention, which bind tightly to various proteolytic enzymes.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents canbe added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred salts are hydrochloride and acetate salts. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

In another aspect, the present invention includes compositions which are useful for in vivo imaging of thrombi in a mammal, comprising a compound of the present invention which is capable of being detected outside the body. Preferred are compositions comprising a compound of the present invention and a detectable label, such as a radioactive or paramagnetic atom.

In another aspect, the present invention provides diagnostic compositions which are use for in vivo imaging of thrombi in a mammal, comprising a pharmaceutically acceptable carrier and a diagnostically effective amount of a compound or composition of the present invention.

In another aspect, the present invention includes methods which are useful for in vivo imaging or thrombi in a mammal.

According to a preferred aspect, useful compounds are those wherein the $R^1$ substituent is substituted with a detectable label, such as a radioactive iodine atom, such as I-125, I-131 or I-123. In this aspect, $R^1$ is preferably phenyl, having a para I-123, para I-125 or para I-131 substitution.

The detectable label can also be a radioactive or paramagnetic chelate in which a suitable ligand (L) is attached to an $R^1$ substituent, either directly or via a divalent linking group A". Alternatively, the. group —A"—L substitutes for the groups —Z—$R^1$ in Formula I. By suitable ligand is meant an organic moiety that is capable of chelating a radioactive or paramagnetic metal ion.

In these compounds, the divalent linking group A" includes groups that are capable of covalently bonding with a free amino group and the chelating means. For example, A" may be —C(=S)—, —C(=O)—, —C(=NH)—(CH$_2$)$_6$—C(=NH)—, —C(=O)—(CH$_2$)$_6$—C(=O)—,

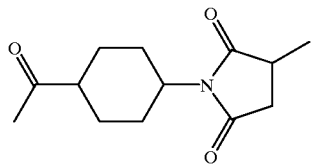

and the like.

Also, in the compounds represented by Formula I, the chelating ligand, L, includes groups capable of covalently bonding to or noncovalently binding to either a radioactive or paramagnetic atom. The chelating means including those which are customarily used for complexing radioactive or paramagnetic atoms. These include chelating means containing 3 to 12, preferably 3 to 8, methylene phosphonic acid groups, methylene carbohydroxamic acid groups, carboxyethylidene groups, or especially carboxymethylene groups which are bonded to a nitrogen atom. If only one or two of the acid groups are bonded to a nitrogen atom, then that nitrogen is bonded to another nitrogen atom having such groups by an optionally substituted ethylene groups or by up to four separated ethylene units separated by a nitrogen or oxygen or sulfur atom. Preferred as a completing means is diethylenetrimine-N,N,N',N",N"-pentaacetic acid (DTPA). DTPA is well known in the art as a chelating means for the radioactive atom indium-111 (In-111), technetium-99m (Tc-99m), and the paramagnetic atom gadoliriuni (Gd). Khaw, et al., *Science* 209:295 (1980); Paik C. H. et al., U.S. Pat. No. 4,652,440 (1987); Gries, H. et al., U.S. Pat. No. 4,957,939 (1990). An preferred chelating ligand, L, is 1-(p-aminobenzyl)-diethylenetriaminepentaacetic acid. Also included as chelating means are compounds which contain sulfhdryl or amine moieties, the total of which in any combination is at least four. These sulfhydryl or amine moieties are separated from each other by at least two atoms which can be either carbon, nitrogen, oxygen, or sulfur. Especially preferred for chelating means, L, is metallothionein which is well known in the art as a chelating means for Tc-99m.

Compounds of Formula I can be labeled with radioactive halogen atom by using an appropriate exchange reaction. Exchange of hot iodine for cold iodine is well known in the art. Alternatively, a radio iodine labeled compound can be prepared from the corresponding bromo compound via a tributylstannyl intermediate. See, U.S. Pat. No. 5,122,361, herein incorporated by reference.

The present invention also includes compositions which are useful for in vivo imaging of thrombi in a mammal, wherein the compositions are comprised of a compound of Formula I complexed with a radioactive atom.

For the compounds of Formula I, suitable radioactive atoms include Co-57, Cu-67, Ga-67, Ga-68, Ru-97, Tc-99m, In-111, In-113m, Hg-197, Au-198, and Pb-203. Some radioactive atoms have superior properties for use in radiochemical imaging techniques. In particular, technetium-99m (Tc-99m) is an ideal radioactive atom for imaging because of its nuclear properties. It is a gamma emitter and has a single photon energy of 140 ke V, a half-life of about 6 hours, and it is readily available from a Mo-99/Tc-99 generator. Rhenium-186 and -188 also have gamma emission which allows it to be imaged. Preferred compositions contain the radioactive atom, Tc-99m.

Compositions of the present invention are conveniently prepared by completing a compound of Formula I with radioisotopes which are suitable for detection externally. The gamma emitters, indium-111m and technetium-99m, are preferred as radioactive atoms because they are detectable with a gamma camera and have favorable half-lives in vivo.

The compounds of Formula I can be labeled by any of the many techniques known in the art to provide a composition of the present invention. For example, these compounds can be labeled through a chelating agent such as diethylenetriaminepentaacetic acid (DTPA) or metallothionein, both of which can be covalently attached to the compound of Formula I via a bond to the $R^1$ or $R^2$ group that will be outside the binding pocket of thrombin.

In general, the compositions of the present invention containing technetium-99m are prepared by forming an aqueous mixture of technetium-99m and a reducing agent and a water-soluble ligand, and then contacting the mixture with a compound of the present invention represented by Formula I. For example, the imaging compounds of this invention are made by reacting technetium-99m (in an oxidized state) with the compounds of the present invention having a chelating means in the presence of a reducing agent to form a stable complex between technetium-99m in a reduced state (IV or V valence state).

One embodiment of the composition of the present invention is prepared by labeling a compound of Formula I having a DTPA chelating means with technetium-99m. This may be accomplished by combining a predetermined amount (as 5 μg to 0.5 mg) of compound of the present invention with an aqueous solution containing citrate buffer and stannous reducing agent, then adding freshly eluted sodium pertechnetate containing a predetermined level of radioactivity (as 15 mCi). After allowing an incubation of the mixture at room temperature, the reaction mixture is loaded into a shielded syringe through a sterile filter (0.2–0.22 micron), then is dispensed into 0.9% saline for injection, if desired.

Another embodiment of the compositions of the present invention is prepared by labeling a compound of Formula I having a metallothionein chelating means with technetium-99m. This may be accomplished by combining aqueous sodium pertechnetate-99m with aqueous stannous glucoheptonate to form a soluble complex of technetium-99m (in reduced state) with two glucoheptonate molecules, then combining this solution with a compound of the Formula I having a metallothionein attached thereto. After incubating the mixture for a period of time and under conditions which allow for an exchange of the technetium-99m from the glucoheptonate complex to the metallothionein of the compound of Formula I, the technetium-labeled composition of the present invention is formed.

The source of technetium-99m should preferably be water soluble. Preferred sources are alkali and alkaline earth metal pertechnetate (TcO$_4^-$). Technetium-99m is most preferably obtained in the form of fresh sodium pertechnetate from a sterile technetium-99m generator (as from a conventional Mo-99/Tc-99m generator). However, any other source of physiologically acceptable technetium-99m may be used.

Reducing agents for use in the method are physiologically acceptable for reducing technetium-99m from its oxidized state to the IV or V valence state or for reducing rhenium from its oxidized state. Reducing agents which can be used are stannous chloride, stannous fluoride, stannous glucoheptonate, stannous tartrate, and sodium dithionite. The preferred agents are stannous reducing agents, especially stannous chloride or stannous glucoheptonate. The amount of reducing agent is that amount necessary to reduce the technetium-99m to provide for the binding to the chelating means of a compound of Formula I in this radioisotope's reduced state. For example, stannous chloride ($SnCl_2$) is the reducing agent and can be used in range from 1–1,000 μg/mL. Especially preferred concentrations are about 30–500 ρg/mL.

Citric acid complexes with technetium-99m quickly to form a stable technetium-99m-citrate complex. Upon contact with a compound of Formula I, substantially quantitative transfer of technetium-99m from its citrate complex to the chelating means of the compound of Formula I is achieved rapidly and under mild conditions. The amount of citric acid (as sodium citrate) can range from about 0.5 mg/ml up to the amount maximally soluble in the medium. Preferred amounts of citric acid range from 15 to 30 μg/ml.

The amount of compound of Formula I having a chelating means can range from 0.001 to about 3 mg/mL, preferably about 0.017 to about 0.15 mg/mL. Finally, technetium-99m in the form of pertechnetate can be used in amounts of preferably about 1–50 mCi. The amount of mCi per mg of compound of the present invention is preferably about 30–150.

The reaction between the compound of Formula I and the metal ion-transfer ligand complex is preferably carried out in a aqueous solution at a pH at which the compound of Formula I is stable. By "stable", it is meant that the compound remains soluble and retains its inhibitory activity against α-thrombin. Normally, the pH for the reaction will be from about 5 to 9, the preferred pH being above 6–8. The technetium-99m-citrate complex and a compound of Formula I are incubated, preferably at a temperature from about 20° C. to about 60° C., most preferably from about 20° C. to about 37° C., for a sufficient amount oftime to allow transfer of the metal ion from the citrate complex to the chelating means of the compound of Formula I. Generally, less than one hour is sufficient to complete the transfer reaction under these conditions.

The present invention also includes compositions of the compounds of the present invention which are useful for in vivo imaging of thrombi in a mammal, comprised of a compound represented by Formula I complexed to a paramagnetic atom.

Preferred paramagnetic atoms are divalent or trivalent ions of elements with an atomic number of 21 to 29, 42, 44 and 58 to 70. Suitable ions include chromium(III), manganese(II), iron(III), iron(II), cobalt(II), nickel(II), copper(II), praseodymium(III), neodymium(III), samarium (III) and ytterbium(III). Because of their very strong magnetic moments, gadolinium(III), terbium(III), dysoprosium (III), holmium(III), and erbium(III) are preferred. Especially preferred for the paramagnetic atom is gadolinium(III).

The compositions of the present invention may be prepared by combining a compound of Formula I with a paramagnetic atom. For example, the metal oxide or a metal salt (for example, nitrate, chloride or sulfate) of a suitable paramagnetic atom is dissolved or suspended in a medium comprised of water and an alcohol, such as methyl, ethyl or isopropyl alcohol. This mixture is added to a solution of an equimolar amount of the compound of Formula I in a similar aqueous medium and stirred. The reaction mixture may be heated moderately until the reaction is completed. Insoluble compositions formed may be isolated by filtering, while soluble compositions may be isolated by evaporation of the solvent. If acid groups on the chelating means are still present in the composition of the present invention, inorganic or organic bases, and even amino acids, may be added to convert the acidic complex into a neutral complex to facilitate isolation or purification of homogenous composition. Organic bases or basic amino acids may be used as neutralizing agents, as well as inorganic bases such as hydroxides, carbonates or bicarbonates of sodium, potassium or lithium.

The present invention also include diagnostic compositions which are useful for in vivo imaging of thrombi in a mammal, comprising a pharmaceutically acceptable carrier and a diagnostically effective amount of compositions derived from the compounds of Formula L. Compositions such as those described in paragraphs B and C herein above may be conveniently used in these diagnostic compositions.

The "diagnostically effective amount" of the composition required as a dose will depend on the route of administration, the type of mammal being treated, and the physical characteristics of the specific mammal under consideration. These factors and their relationship to determining this dose are well known to skilled practitioners in the medial diagnostic arts. Also, the diagnostically effective amount and method of administration can be tailored to achieve optimal efficacy but will depend on such factors as weight, diet, concurrent medication and other factors which those skilled in the medical arts will recognize. In any regard, the dose for imaging should be sufficient for detecting the presence of the imaging agent at the site of a thrombus in question. Typically, radiologic imaging will require that the dose provided by the pharmaceutical composition trsition of the present invention be about 5 to 20 μCi, preferably about 10 μCi. Magnetic resonance imaging will require that the dose provided be about 0.001 to 5 mmole/kg, preferably about 0.005 to 0.5 mmole/kg of a compound of Formula VII complexed with paramagnetic atom. In either case, it is known in the art that the actual dose will depend on the location of the thrombus.

"Pharmaceutically acceptable carriers" for in vivo use are well known in the pharmaceutical art, and are described, for example, in *Remington's Pharmaceutical Sciences*, Mack Publishing Co. (A. RP Gennaro edit. 1985). The pharmaceutical compositions of the present invention may be formulated with a pharmaceutically acceptable carrier to provide sterile solutions or suspensions for injectable administration. In particular, injectables can be prepared in conventional forms, either as liquid solutions or suspensions, solid forms suitable for solution or suspensions in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

The present invention also encompasses diagnostic compositions prepared for storage or administration. These would additionally contain preservatives, stabilizers and dyes. For example, sodium benzoate, sorbic acid and esters of p-hydroxybenzoic acid may be added as preservatives. Id.

At 1449. In addition, antioxidants and suspending agents may be used. Id.

The in vivo imaging methods of the present invention also offer several advantages over previous imaging techniques for the detection or monitoring of the presence, size, regression or increase of a thrombus. In particular, the present invention provides compounds, compositions and diagnostic compositions have been designed to bind extremely tightly to the thrombin associated with a thrombus and thereby reduce "background" due to circulating radioactivity or paramagnetism arising from unbound imaging agent. Furthermore, in vivo imaging by intracoronary injection of the compounds, compositions or diagnostic compositions of the present invention, is expected to be almost instantaneous since these imaging agents would saturate the thrombin bound to the thrombus immediately.

Accordingly, the present invention also includes methods for in vivo imaging of a thrombus in a mammal, comprising the steps of: (1) administering to a mammal a diagnostically acceptable amount of a compound, composition, or diagnostic composition of the present invention and (2) detecting a thrombus in a blood vessel.

The term "in vivo imaging" as used herein relates to methods of the detection of a thrombus in a meal, as well as the monitoring of the size, location and number of thrombi in a mammal, as well as dissolution or growth of the thrombus.

In employing the compounds, compositions or diagnostic compositions in vivo by this method, "administering" is accomplished parenterally, in either a systemic or local targeted manner. Systemic administration is accomplished by injecting the compounds, compositions by diagnostic compositions of the present invention into a convenient and accessible vein or artery. This includes but is not limited to administration by the ankecubutal vein. Local targeted administration is accomplished by injecting the compounds, compositions or diagnostic compositions of the present invention proximal in flow to a vein or artery suspected to contain thrombi distal to the injection site. This includes but is not limited to direct injection into the coronary arterial vasculature to image coronary thrombi, into the carotid artery to image thrombi in the cerebral vasculature, or into a pedal vein to image deep vein thrombosis of the leg.

Also, the manner of delivery of a composition of the present invention to the site of a thrombus is considered within the scope of the term "administering". For example, a compound represented by Formula I having a chelating means attached thereto may be injected into the mammal, followed at a later time by the radioactive atom thereby forming in vivo at the site of the thrombus the composition comprising the compound of formula complexed to radioactive atom. Alternatively, a composition comprising the compound of formula complexed to radioactive atom may be injected into the mammal.

The "diagnostically effective amount" of the compounds, compositions or diagnostic compositions used in the methods of the present invention will, as previously mentioned, depend on the route of administration, the type of mammal being treated, and the physical characteristics of the specific mammal under treatment. These factors and their relationship to determining this dose are well known to skilled practitioners in the medical diagnostic arts. In any regard, the dose for in vivo imaging should be sufficient for detecting the presence of the imaging agent at the site of a thrombus in question. Typically, radiologic imaging will require that the dose provided by the diagnostic composition of the present invention be about 5 to 20 $\mu$Ci, preferably about 10 $\mu$Ci. Magnetic resonance imaging will require that the dose provided by the diagnostic composition be about 0.001 to 5 mmole/kg, preferably about 0.005 to 0.5 mmole/kg of a compound of Formula I complexed with paramagnetic atom. In either case, it is known in the art that the actual dose will depend on the location of the thrombus.

The detecting of a thrombus by imaging is made possible by the presence of radioactive or paramagnetic atoms localized at such thrombus.

The radioactive atoms associated with the compositions and diagnostic compositions of the present invention are preferably imaged using a radiation detection means capable of detecting gamma radiation, such as a gamma camera or the like. Typically, radiation imaging cameras employ a conversion medium (wherein the high energy gamma ray is absorbed, displacing an electron which emits a photon upon its return to the orbital state), photoelectric detectors arranged in a spatial detection chamber (to determine the position of the emitted photons), and circuitry to analyze the photons detected in the chamber and produce an image.

The paramagnetic atoms associated with the compositions and diagnostic compositions of the present invention detected in magnetic resonance imaging (MRI) systems. In such systems, a strong magnetic field is used to align the nuclear spin vectors of the atoms in a patient's body. The field is disturbed by the presence of paramagnetic atoms localized at a thrombus and an image of the patient is read as the nuclei return to their equilibrium alignments.

The following examples are illustrative, but not limiting, of the method and compositions of the present invention. Other suitable modifications and adaptations of the variety of conditions and parameters normally encountered and obvious to those skilled in the art are within the spirit and scope of the invention.

Scheme 3

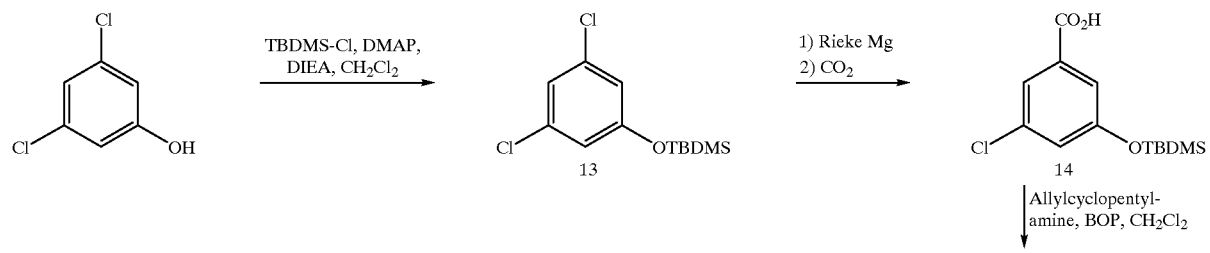

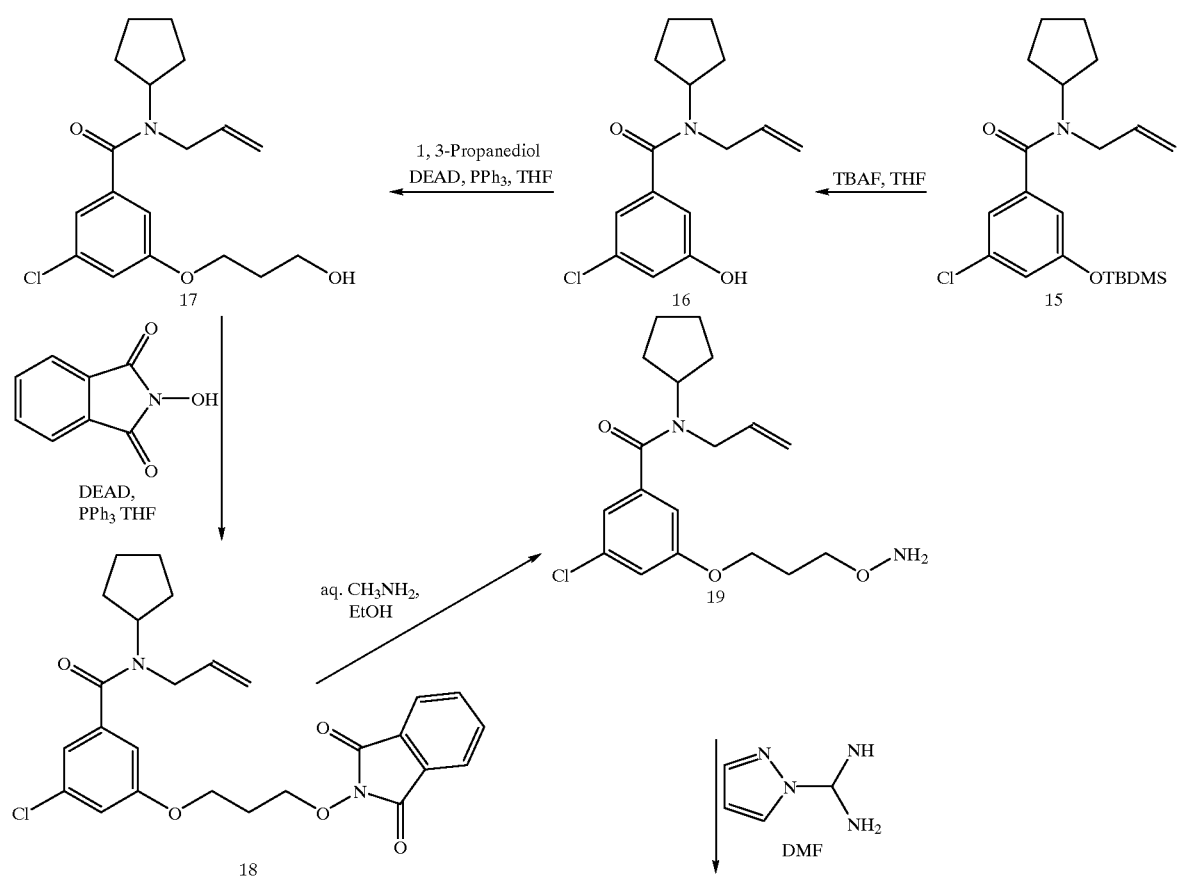
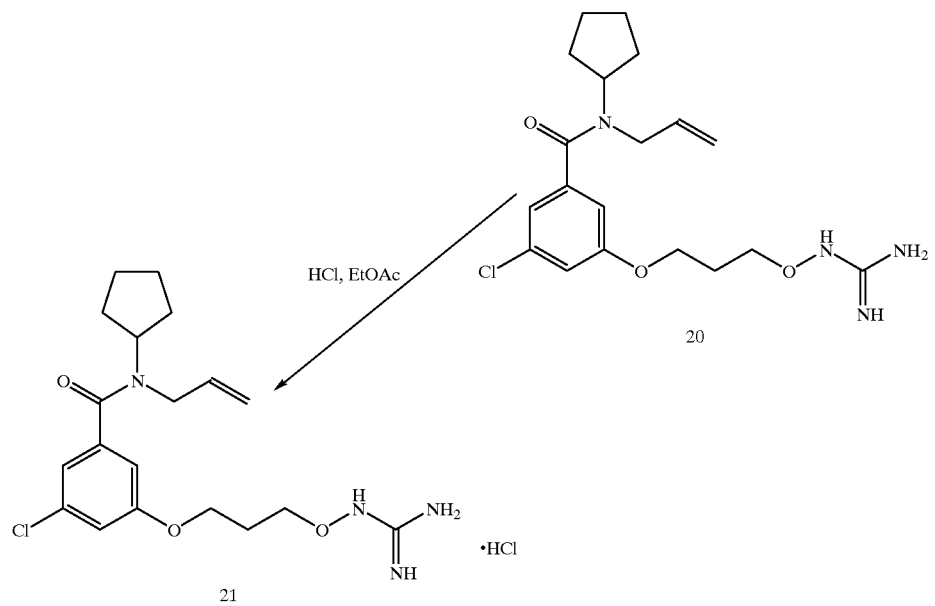

Scheme 4

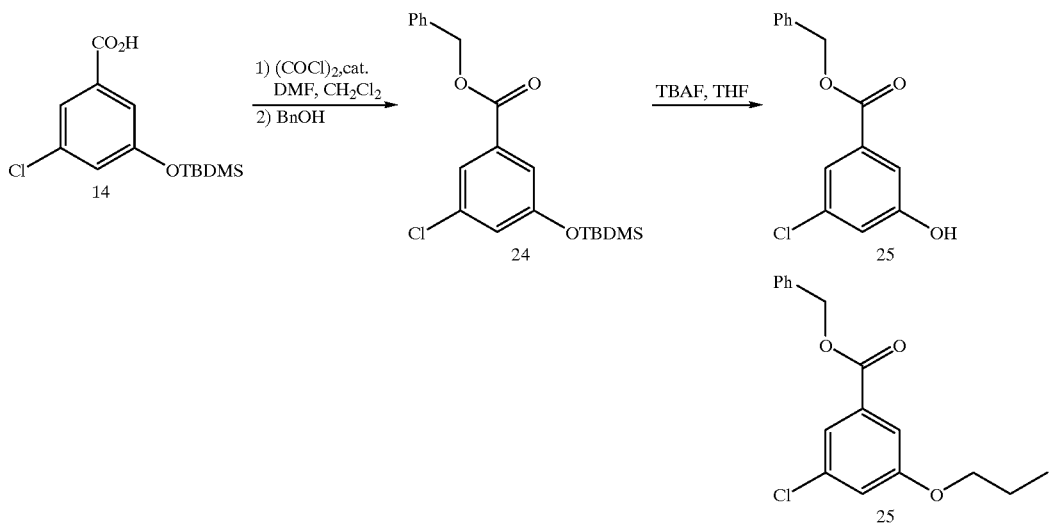

EXAMPLE 1

[3-{5-Chloro-3-(N-cyclopentyl-N-[prop-2-enyl]aminocarbonyl)phenoxy}propoxyamino]carboxamidine hydrochloride (21)

Compound numbers appearing in Examples 1–21 refer to compounds having the structures shown in Schemes 3 and 4.

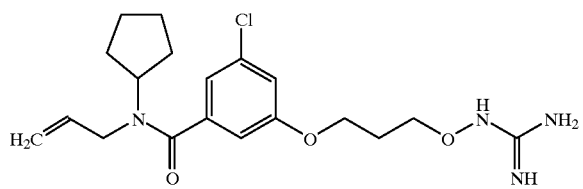

a.) 1,3-Dichloro-5-(tert-butyldimethylsilyloxy)benzene (13)

To a solution of $CH_2Cl_6$ (60 mL) and 3,5-dichlorophenol (5.0 g 30 mmol) was added tert-butyldimethylsilyl chloride (5.54 g, 36 mmol), N,N-diisoprpylethylamine (8.0 mL, 46 mmol) and a catalytic amount of 4-dimethylaminopyridine. The initially exothermic solution was stirred at ambient temperature for 6 h then diluted with $CH_2Cl_2$ (40 mL). The mixture was washed consecutively with 10% aqueous HCl (50 mL), saturated aqueous $NaHCO_3$ (50 mL), and brine (50 mL). the organic phase was dried over anhydrous $MgSO_4$, filtered and concentrated in vacuo to provide 13 as a pale yellow liquied (8.8 g, 100%). $^1$H NMR (300 MHz, $CDCl_3$) d 6.98 s, 1H), 6.72 (s, 2H), 0.98 (s, 9H), 0.22 (s, 6H).

b.) 3—Chloro-5-(tert-butyldimethylsilyloxy)benzoic acid (14)

To "Rieke Mg" (0.21 mol; Rieke, R. D.; Bales, S. E.; Hudnall, P. M.; Bums, T. P.; Poindexter, G. S. *Org. Synth. Collective Volume* VI, 1988, 845.) in tetrahydrofuran (1000 mL) was added ether 13 (27.7 g, 0.10 mol). After the reaction mixture was stirred for 20 min at ambient temperature there was an exotherm observed. The exotherm. subsided within 5 min, and the reaction mixture was cooled to 20° C. with an ice bath. After 15 min, the reaction mixture was cooled to −78° C. To the cool reaction mixture was added $CO_2$ gas for 30 min. The reaction mixture was warmed to ambient temperature, then diluted with cold (0° C.) 10% aqueous HCl (150 mL) and ethyl acetate (400 mL). The aqueous phase was extracted with ethyl acetate (400 mL). The combined organic phases were washed with brine, dried over anhydrous $MgSO_4$, filtered and concentrated in vacuo. The resulting solid was recrystallized from acetonitrile to provide 14 as fluffy white needles (19.3 g, 64%). $^1$H NMR (300 MHz, $CDCl_3$) δ 7.70 (s, 1H), 7.43 (s, 1H), 7.08 (s, 1H), 0.99 (s, 9H), 0.23 (s, 6H). IR (KBr) 2957, 1697, 1578, 1434, 1297, 1266, 1115, 990,871 $cm^{-1}$.

c.) [3chloro-5-(tert-butyldimethylsilylox)phenyl]-N-cyclopentyl-N-prop-2-enylcarboxamide (15)

To a solution of $CH_2Cl_2$ (250 mL) and acid 14 (17.5 g, 60 mmol) was added triethylamine (33.8 mL, 0.24 mol) and bis(2-oxo-3-oxazolidinyl)phosphinic chloride (17.0 g, 66 mmol). The resulting mixture was stirred for 5 min, then N-allylcyclopentylamine (9.8 mL, 66 mmol) was added. The mixture was stirred for 1h then filtered. The filtrate was washed with 10% aqueous HCl (100 mL), saturated aqueous $NaHCO_3$ (100 mL) and brine (100 mL). The organic layer was dried over anhydrous $MgSO_4$ and concentrated in vacuo. The crude product was purified by chromatography on silica gel to provide compound 15 as a colorless oil (23.5 g, 97%). $^1$H NMR (300 MHz. $CDCl_3$) δ 6.95 (s, 1H), 6.84 (s, 1H), 6.71 (s, 1H), 5.93 (bs, 1H, 5.16 (d, 2H), 3.95 (bs, 3H), 1.4–1.9 (m, 8H), 0.97 (s, 9H), 0.20 (s, 6H). Mass spectrum (CI) calcd. for $C_{21}H_{32}NO_2SiCl$: 394 (M+H). Found: 394.

d.) (5-chloro-3-hydroxyphenyl)-N-cyclopentyl-N-prop-2-enylcarboxamide (16)

To a solution of compound 15 (23.4 g, 59 mmol) and tetrahydrofuran (200 mL) was added tetrabutyl-ammonium fluoride (1M in tetrahydrofuran, 66 mL, 66 mmol). The solution was stirred for 30 min, then poured into a separatory funnel containing 10% aqueous HCl (100 mL) and ethyl acetate (200 mL). The layers were separated and the aqueous layer was extracted with ethyl acetate (200 mL). The organic layers were combined, washed with brine (100 mL), dried over anhydrous MgSO$_4$ and concentrated in vacuo. The crude product was purified by chromatography on silica gel to yield phenol 16 (12 g, 72%). $^1$H NMR (300 MHz, CDCl$_3$) δ 8.73 (bs, 1H), 6.82 (s, 2H), 6.76 (s, 1H), 5.95 (bs, 1H), 5.16–5.23 (m, 2H), 3.7–4.15 (m, 3H), 1.45–2.0 (m, 8H). IR(NaCl) 3177, 2956, 1590, 1433, 1373, 1289, 935 cm$^{-1}$.

e.) [3-chloro-5-(3-hydroxypropoxy)phenyl]-N-cyclopentyl-N-prop-2-enylcarboxamide (17)

To a solution of tetrahydrofuran (100 mL), 1,3-propanediol (1.6 mL, 30 mmol) and phenol 16 (4.3 g, 15 mmol) at 0° C. was added diethyl azodicarboxylate (DEAD, 3.6 mL, 23 mmol) dropwise over 10 min. The solution was warmed to ambient temperature and stirred for 16 h, prior to concentration in vacuo. The oil was partially purified by chromatography on silica gel to provide alcohol 17 (3.9 g) contaminated with Mitsunobu by-products. This material was used directly in subsequent experiments. $^1$H NMR (300 MHz, CDCl$_3$) δ 6.93 (s, 2H), 6.8 (s, 1H), 5.9 (bs, 1H), 5.18 (d, 2H), 4.4–3.8 (m, 7H), 2.05 (m, 2H), 1.4–1.9 (m, 10H). Mass spectrum (CI) calcd. for C$_{18}$H$_{24}$NO$_3$Cl: 338 (M+H). Found: 338.

f.) {5-[3-(1,3-dioxoisoindolin-2-yloxy)propoxy]-3-chlorophenyl}-N-cyclopentyl-N-prop-2-enylcarboxamide (18)

A mixture of alcohol 17 (8.8 g, 26 mmol), tetrahydrofuran (100 mL), N-hydroxyphthalimide (3.8 g, 23 mmol) and triphenylphosphine (5.2 g, 20 mmol) was stirred at 0° C. for 5 min. To the mixture was added DEAD (3.4 mL. 20 mmol) dropwise. The reaction mixture was then allowed to warm to ambient temperature and stirred for 12 h prior to concentration in vacuo. The residue was purified by chromatography to provide phthalimide 18 (3.7 g) contaminated with Mitsunobu by-products. This material was used directly in subsequent experiments. $^1$H NMR (300 MHz, CDCl$_3$) δ 7.78–7.85 (m, 2H), 7.73–7.77 (m, 2H), 6.94 (t, 2H), 6.38 (d, 1H), 5.95 (bs, 1H), 5.18 (d, 2H), 4.40 (t, 2H), 3.8–4.4 (m, 4H), 2.20–2.28 (m, 2H), 1.4–1.9 (m, 1H). Mass spectrum (CI) calcd. for C$_{26}$H$_{27}$N$_2$O$_5$Cl: 483 (M+H). Found: 483.

g.) {5-[3-(aminooxy)propoxy]-3-chlorophenyl}-N-cyclopentyl-N-prop-2-enyl carboxamide (19)

To a solution of ethanol (50 mL) and phthalimide 18 (1.8 g, 3.7 mmol) was added 40% aqueous methylamine (25 mL). The reaction mixture was stirred at ambient temperature for 16 h. The reaction mixture was concentrated in vaczio and then chromatographed on silica gel to provide hydroxylamine 19 (0.5 g; 15% from 16). $^1$H NMR (300 MHz, CDCl$_3$) δ 6.92 (s, 2H), 6.79 (s, 1H), 5.92 (bs, 1H), 5.40 (s, 2H), 5.17 (m, 2H), 4.04 (t, 2H), 3.88–4.03 (m, 3H), 3.82 (t, 2H), 3.88–4.03 (m, 3H), 3.82 (t, 2H), 2.01–2.12 (m, 2H), 1.4–1.9 (m, 8H).

h.) [3-{5-Chloro-3-(N-cyclopentyl-N-[prop-2-enyl] aninocarbonyl)phenoxy}propoxyamino] carboxamidine (20)

To a solution of amine 19 (1.4 g, 4 mmol) in N,N-dimethylformamide (20 mL) was added 1H-pyrazole-1-carboxamidine hydrochloride (0.61 g, 4 mmol). The reaction mixture was stirred for 18 h, concentrated in vacuo, and purified by chromatography on silica gel to provide 20 (0.94 g, 61%) as a viscous oil.

i.) [3-{5-Chloro-3-(N-cyclopentyl-N-[prop-2-enyl] aminocarbonyl)phenoy}propoxyamino] carboxamidine hydrochtioride (21)

To a solution of 20 (0.6 g, 1.5 mmol) and ethyl acetate (10 mL) was added 4N HCl in ethyl acetate (4 mL). The resulting mixture was concentrated to dryness in vacuo, and triturated with ether to provide title compound 21 (0.57 g, 88%) as a white amorphous solid. $^1$H NMR (300 MHz, CDCl$_3$) δ 7.07 (s, 1H), 6.95 (s, 1H), 6.85 (s, 1H), 5.93 (bs, 1H), 5.18 (d, 2H), 4.14 (t, 2H), 4.07 (t, 2H), 3.95–4.1 (m, 2H), $^{13}$C NMR(CD$_3$OD) δ 161.0, 136.0, 119.6, 116.9, 112.3, 75.2, 66.3, 30.7, 28.7, 25.0. IR(KBr)3355, 3137, 2951, 1670, 1618, 1437, 1052, 651 cm$^{-1}$. Mass spectrum(CI) calcd. for C$_{19}$H$_{27}$N$_4$O$_3$Cl: 395(M+H). Found: 395.

EXAMPLE 2

[3-{5-Chloro-3-(4-benzylpiperidinylcarbonyl) phenoxy}propoxyamino]carboxamidine trifluoroacetate (32)

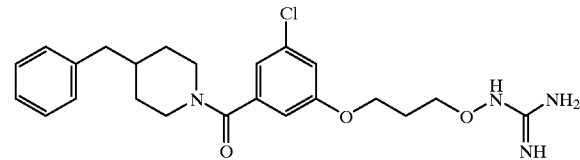

a.) Benzyl 3-chloro-5-(tert-butyldimethylsilyloxy) benzoate (24)

To a mixture of the acid 14 (3.80 g, 13.3 mmol) and oxalyl chloride (5.8 mL, 66 mmol) in methylene chloride (60 mL) was added ca. 0.05 mL of N,N-dimethylformamide as a catalyst. After stirring 1 hr at ambient temperature, the reaction was evaporated in vacuo, diluted with methylene chloride, and reacted with benzyl alcohol (1.38 mL, 13.3 mmol) and 4-(N,N-dimethylamino)pyridine (1.60 g, 13.3 mmol). After stirring 16 hrs at ambient temperature, the solution was washed with dilute aqueous HCl, dilute aqueous NaHCO$_3$, and brine, dried over Na$_2$SO$_4$, and filtered. The filtrate was then evaporated in vacuo giving a quantitative yield of gold oil. $^1$H NMR (300 MHz, CDCl$_3$) δ 7.64 (t, 1H, J=1.5 Hz), 7.45–7.28 (m, 6H), 7.02 (m, 1H), 5.35 (s, 2H), 0.98 (s, 9H), 0.22 (s, 6H).

b.) Benzyl 3-chloro-5-hydroxybenzoate (25)

A 1.0 M solution of tetrabutylammonium fluoride in tetrahydrofuiran (26.6 mL, 26.6 mmol) was added to neat benzyl ester 24 (5.00 g, 13.3 mmol), the reaction stirred 10 minutes at ambient temperature, and evaporated in vacuo. The crude product was dissolved in methylene chloride, the solution washed with dilute aqueous NaHCO$_3$, dried overNa$_2$SO$_4$, and filtered. The evaporated filtrate was then washed repeatedly with hexanes and dried in vacuo giving product 25 as a gold oil (3.40 g, 98%). $^1$H NMR (300 MHz, CDCl$_3$) δ 7.35 (m, 7H), 7.1 (t, 1H, J=2.1 Hz), 5.28 (s, 2H).

c.) Benzyl 3-chloro-5-(3-hydroxypropoxy)benzoate (26)

To a solution of phenol 25 (8.80 g, 33.0 mmol) and 3-bromno-1-propanol (2.9 mL, 33 mmol) in acetonitrile (300 nL) was added solid cesium carbonate (12 g, 37 mmol). After stirring 16hrs at 50° C., more 3-bromo-1-propanol (3.3 mmol) and cesium carbonate (3.3 mmol) were added and the reaction stirred another 2 hrs. After adding more 3-bromo-1-propanol and cesium carbonate (3.3 mmol each) and sodium iodide (3.3 mmol), the reaction was stirred 30 minutes at 65° C., then cooled and filtered. The filtrate was evaporated in vacuo, the residue dissolved in ethyl acetate, washed with water, and the organic layer dried over $Na_2SO_4$ and filtered. The evaporated filtrate then gave product 26 (5.96 g 56%). $^1$H NMR (300 MHz, $CDCl_3$) δ 7.63 (t, 1H, J=1.5 Hz), 7.48 (dd, 1H, J=2.4 Hz, 1.4 Hz), 7.46–7.31 (m, 5H), 7.09 (t, 1H, J=2.4 Hz), 5.35 (s, 2H), 4.14 (t, 2H, J =6.0 Hz), 3.85 (t, 2H, J=6.0 Hz), 2.05 (pentet, 2H, J=6.0 Hz).

d.) Benzyl 5-[3-(1,3-dioxoisoindolin-2-yloxy)propoxy]-3-chlorobenzoate (27)

A solution of alcohol 26 (5.96 g, 18.6 mmol), triphenylphosphine (5.40 g, 20.5 mmol), and N-hydroxyphthalirnide (2.10 g, 20.5 mmol) in tetrahydrofuran (186 mL) was cooled to 0° C. and reacted slowly with diethyl azodicarboxylate (3.50 mL, 22.3 mmol). After warming to ambient temperature and stirring 16 hrs, the reaction was concentrated in vacuo and purified by chromatography on silica gel (10% ethyl acetate in hexanes) giving product 27 (5.18 g, 60%). $^1$H NMR (300 MHz, $CDCl_3$) δ 7.83 (dd, 2H, J=5.6 Hz, 3.1 Hz), 7.75 (dd, 2H, J=5.6 Hz, 3.1 Hz), 7.63 (t, 1H, J=1.5 Hz), 7.51 (dd, 1H, J=2.4 Hz, 1.4 Hz), 7.40 (m, 5H), 7.12 (t, 1H, J=2.3 Hz), 5.35 (s, 2H), 4.41 (t, 2H, J=6.1 Hz), 4.28 (t, 2H, J=6.1 Hz), 2.25 (pentet, 2H, J=6.1 Hz).

e.) Benzyl 5-[3-(aminooxy)propoxy]-3-chlorobenzoate (28)

To a solution of phthalimide 27 (1.00 g, 2.15 mmol) in tetrahydrofuran (20 mL) was added a 40% aqueous solution of methylamine (0.148 mL, 1.72 mmol). After stirring 25 minutes at 0° C., the reaction was evaporated in vacuo, the residue partitioned between methylene chloride and water, and the organic layer dried over $Na_2SO_4$ and filtered. The evaporated filtrate was then purified by chromatography on silica gel (40% ethyl acetate in hexanes) giving product 28 (0.576 g, 80%). $^1$H NMR (300 MHz, $CDCl_3$) δ 7.62 (t, 1H, J=1.6 Hz), 7.48 (dd, 1H, J=2.4 Hz, 1.4 Hz), 7.45–7.32 (m, 5H), 7.08 (t, 1H, J=2.1 Hz), 5.35 (s, 2H), 4.07 (t, 2H, J=6.3 Hz), 3.82 (t, 2H, J=6.3 Hz), 2.07 (pentet, 2H, J=6.3 Hz).

f.) Benzyl 5-[3-{N,N'di-(tert-butoxycarbonyl)amidinoaminooxy}propoxy]-3-chlorobenzoate (29)

A solution of amine 28 (0.710 g, 2.10 mmol) and N,N'-bis(tert-butoxycarbonyl)amidinopyrazole (0.724 g, 2.30 mmol) in N,N-dimethylformamide (10 mL) was stirred for 3 days at ambient temperature and evaporated in vacuo. The crude product was purified by chromatography on silica gel (20% diethyl ether in petroleum ether) giving compound 29 (0.83 g, 69%). $^1$H NMR (300 MHz, $CDCl_3$) δ 9.08 (s, 1H), 7.70 (s, 1H), 7.62 (t, 1H, J=1.6 Hz), 7.47 (dd, 1H, J=2.5 Hz, 1.4 Hz), 7.45–7.32 (m, 5H), 7.09 (t, 1H, J=2.1 Hz), 5.35 (s, 2H), 4.23 (t, 2H, J=6.0 Hz), 4.10 (t, 2H, J=6.0 Hz), 2.18 (pentet, 2H, J=6.2 Hz), 1.49 (s, 18H).

g.) 5-[3-{N,N'-Di-(tert-butoxycarbonyl)amindinoaminooxy}propoxy]-3-chlorobenzoic acid (30)

To a solution of product 29 (2.80 g, 4.85 mmol) in ethanol (48 mL) was added a 2N aqueous solution of NaOH (22 mL, 44 mmol). The solution was stirred 30 minutes at ambient temperature and the ethanol removed in vacuo. The remaining solution was acidified to pH 3 with 10% aqueous citric acid and extracted with methylene chloride. The organic layer was dried over $Na_2SO_4$, filtered, the filtrate evaporated, and the crude product purified by chromatography on silica gel (30% ethyl acetate in hexanes) giving compound 30 (1.50 g, 64%). $^1$H NMR (300 MHz, $CDCl_3$) δ 9.10 (s, 1H), 8.73 (bs, 1H), 7.69 (bs, 1H, 7.66 (t, 1H, J=1.5 Hz), 7.50 (dd, 1H, J=2.3 Hz, 1.3 Hz), 7.12 (t, 1H, J=2.3 Hz), 4.24 (t, 2H, J=6.0 Hz), 4.12 (t, 2H, J=6.2 Hz), 2.20 (pentet, 2H, J=6.1 Hz), 1.50 (s, 18H). Mass spectrum (LCMS, ESI pos.) calcd. for $C_{21}H_{30}N_3O_8Cl$: 288.0 (M−2 Boc+H). Found: 288.2.

h.) [3-{5-Chloro-3-(4-benzylpiperidinylcarbonyl)phenoxy}propoxyamino]-N,N'-di-(tert-butoxycarbonyl)carboxamidine (31)

A solution of product 30 (0.032 g, 0.066 mmol), benzotriazole-1-yl-oxy-tris-(dimethylamino)-phosphonum hexafluorophosphate(0.032 g,0.072 mmol), and triethylamine (0.01 mL, 0.07 mmol) in methylene chloride (1.0 mL) was added to a vial containing diethylaminomethyl-polystyrene resin (0.06 g) and 4-benzylpiperidine (0.014 g, 0.077 mmol). The reaction was shaken for 3 days, poured onto a Waters 2 g silica Sep-Pak, and the product eluted with 5 to 15% methanol in methylene chloride. The product-containing fractions were combined, washed with 10% aqueous citric acid and saturated aqueous $NaHCO_3$, and dried over $Na_2SO_4$. The decanted solution was evaporated in vacuo giving a clear oil that was used directly in the proceeding step without analysis.

i.) [3-{5-chloro-3-(4-benzylpiperidinylcarbonyl)phenoxy} propoxyamino]carboxamidine trifluoroacetate (32)

Product 31 was dissolved in methylene chloride (2.0 mL), treated with trifluoroacetic acid (0.5 mL), tightly capped, and shaken for 18 hrs at ambient temperature. The solution was evaporated in vacuo and the crude product purified on a Waters 2 g silica Sep-Pak (5 to 20% methanol in methylene chloride) giving title compound 32 (0.032 g, 87% from 30). $^1$H NMR (300 MHz, $CDCl_3$) δ 7.33–7.19 (m, 3H), 7.15 (m, 2H), 6.96 (m, 1H), 6.92 (t, 1H, J=1.5 Hz), 6.79 (dd, 1H, 2.3 Hz, 1.3 Hz), 4.60 (bd, 1H, 13 Hz), 4.10 (t, 2H, J=5.9 Hz), 4.07 (t, 2H, J=6.1 Hz), 2.98 (bt, 1H J=12 Hz), 2.73 (bt, 1H J=13 Hz), 2.58 (d. 2H, J=7.0 Hz), 2.15 (pentet, 2H, J=6.0 Hz), 1.83 (m, 2H), 1.65 (bd, 1H J=13 Hz), 1.21 (m, 2H). Mass spectrum (MALDI-TOF, gentisic acid matrix) calcd. for $C_{23}H_{29}N_4O_3Cl$: 445.2 (M+H). Found: 445.1.

EXAMPLE 3

[3-{5-Chloro-3-(N,N-bis[2-methoxyethyl]aminocarbonyl)phenoxy)}propoxyaimino]carboxamidine trifluoroacetate

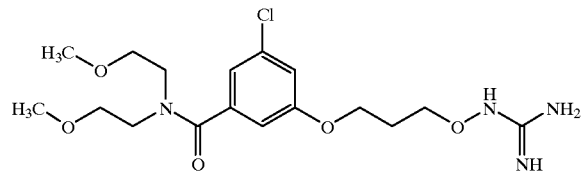

The title compound was prepared from compound 30 and bis(2-methoxyethyl)amine in a manner analogous to steps h and i of Example 2. ¹H NMR (300 MHz, CDCl₃CD₃/OD) δ 7.00 (t, 1H, J=1.6 Hz), 6.95 (t, 1H, J 2.1 Hz), 6.86 (dd, 1H, J=2.3 Hz, 1.3 Hz), 4.10 (t, 2H, J=5.8 Hz), 4.07 (t, 2H, J=6.1 Hz), 3.72 (bm, 2H), 3.66 (bm, 2H), 3.52 (bm, 2H), 3.46 (bm, 2H), 3.39 (bs, 3H), 3.30 (bs, 3H), 2.15 (pentet, 2H, J=6.2 Hz). Mass spectrum (MALDI-TOF, gentisic acid matrix) calcd. for $C_{17}H_{27}N_4O_5Cl$: 402.2 (M). Found: 402.0.

EXAMPLE 4

[3-{5-Chloro-3-N-metyl-N-[2-{2-pyridyl}ethyl] aminocarbonyl)phenoxy}propoxyamino] carboxamidine trifluoroacetate

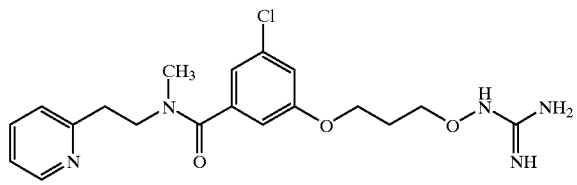

The title compound was prepared from compound 30 and methyl(2-pyridyl-2-ethyl)amine in a manner analogous to steps h and i of Example 2. ¹H NMR (300 MHz, CDCl₃/CD₃OD) δ 8.70 (m, 1H), 8.18 (t, 1H, J=7.6 Hz), 7.75 (d, 1H J=7.9 Hz), 7.64 (bt, 1H, J=6.5 Hz), 6.95 (bs, 1H), 6.86 (bs, 1H), 6.74 (bs, 1H), 4.08 (m, 6H), 3.90 (t, 2H, J=6.8 Hz), 3.37 (m, 2H), 3.02 (s, 3H), 2.14 (pentet, 2H, J=5.9 Hz). Mass spectrum (MALDI-TOF, gentisic acid matrix) calcd. for $C_{19}H_{24}N_5O_3Cl$: 406.2 (M+H). Found: 406.3.

EXAMPLE 5

[3-{5-Chloro-3-(N-methyl-N-[3-pyridylmethyl] aminocarbonyl)phenoxy}propoxyamino] carboxamidine trifluoroacetate

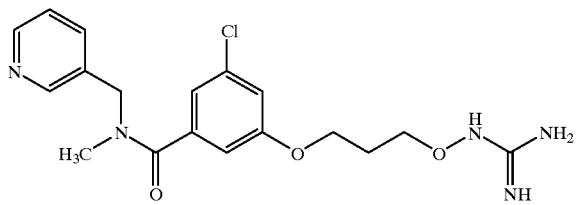

The title compound was prepared from compound 30 and methyl(3-pyridylmethyl)amine in a manner analogous to steps h and i of Example 2. ¹H NMR (300 MHz, CDCl₃/CD₃OD) δ 8.74–8.65 (bm, 1H), 8.11 (bm, 1H, 7.67 (bm, 1H), 7.53 (bm, 1H), 6.99 (m, 2H), 6.88 (bs, 1H), 4.80 (s, 2H), 4.08 (m, 4H), 3.00 (bs, 3H), 2.16 (m, 2H). Mass spectrum (MALDI-TOF, α-cyano-4-hydroxycinnamic acid matrix) calcd. for $C_{18}H_{22}N_5O_3Cl$: 391.1 (M). Found: 391.5.

EXAMPLE 6

[3-{5-Chloro-3-(N-ethyl-N-[4-pyridylmetyl] aminocarbonyl)phenoxy}propoxyamino] carboxamidine trifluoroacetate

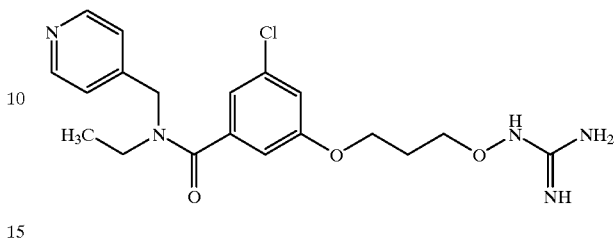

The title compound was prepared from compound 30 and ethyl(4-pyridylmethyl)amine in a manner analogous to steps h and i of Example 2. Mass spectrum (MALDI-TOF, gentisic acid matrix) calcd. for $C_{19}H_{24}N5O_3Cl$: 405.2 (M). Found: 405.5.

EXAMPLE 7

Ethyl 2-[5-{3-(amidinoaminooxy)propoxy}-3-chlorophenyl]-N-{2-pyridylmethyl}aminocarbonyl] acetate trifluoroacetate

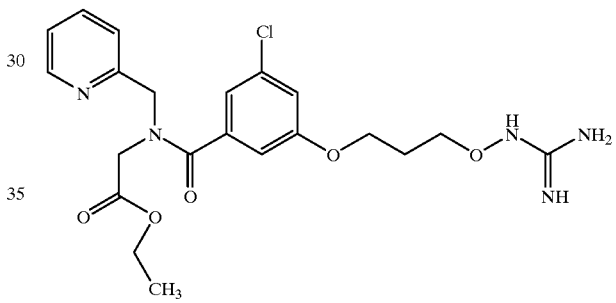

The title compound was prepared from compound 30 and 2-pyridylmethylglycine ethyl ester in a manner analogous to steps h and i of Example 2. Mass spectrum (MALDI-TOF, gentisic acid matrix) calcd. for $C_{21}H_{26}N_5OCl$: 463.2 (M). Found: 463.5.

EXAMPLE 8

[3-{5-Chloro-3-([2-{3,4-dihydroxyphenyl}-2-oxoethyl]-N-methyl aminocarbonyl) phenoxy}propoxyamino]carboxamidine trifluoroacetate

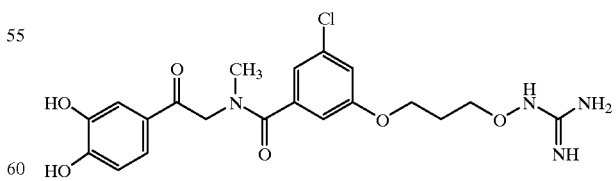

The title compound was prepared from compound 30 and methyl-2-(3,4-dihydroxyphenylacetyl)amine in a manner analogous to steps h and i of Example 2. Mass spectrum (MALDI-TOF, gentisic acid matrix) calcd. for $C_{20}H_{23}N_{4l}o_6Cl$: 450.1 (M). Found: 450.2.

EXAMPLE 9

[3-{5-Chloro-3-(N-[2-{dimethylamino}ethyl]-N-ethylaminocarbonyl)phenoxy}propoxyamino]carboxamidine trifluoroacetate

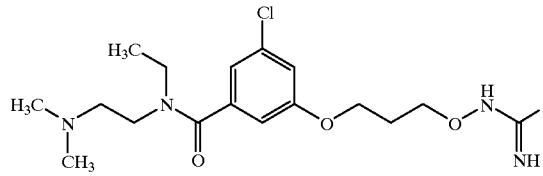

The title compound was prepared from compound 30 and ethyl(2-dimethylaminoethyl)amine in a manner analogous to steps h and i of Example 2. $^1$H NMR (300 MHz, CDCl$_3$/CD$_3$OD) δ 6.99 (t, 1H, J=2.1 Hz), 6.96 (m, 1H), 6.88 (bs, 1H), 4.10 (m, 4H), 3.83 (t, 2H, J=6.6 Hz), 3.38 (m, 4H), 2.96 (bs, 6H), 2.16 (pentet, 2H, J=6.0 Hz), 1.14 (t, 3H, J=7.0 Hz). Mass spectrum (MALDI-TOF, α-cyano-4-hydroxycinnamic acid matrix) calcd. for C$_{17}$H$_{28}$N$_5$O$_3$Cl: 385.2 (M). Found: 385.6.

EXAMPLE 10

[3-{5-Chloro-3-(4-formylpiperazinylcarbonyl)phenoxy}propoxyamino]carboxamidine trifluoroacetate

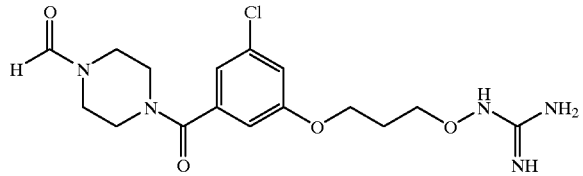

The title compound was prepared from compound 30 and 4-piperazinecarboxaldehyde in a manner analogous to steps h and i of Example 2. $^1$H NMR (300 MHz, CDCl$_3$/CD$_3$OD) δ 8.08 (bs, 1H), 7.01 (t, 1H, J=2.1 Hz), 6.97 (m, 1H), 6.84 (dd, 1H J=2.3 Hz, 1.4 Hz), 4.14–4.06 (m, 4H), 2.16 (pentet, 2H, 6.0 Hz). Mass spectrum (MALDI-TOF, gentisic acid matrix) calcd. for C$_{16}$H$_{22}$N$_5$O$_4$Cl: 383.1 (M). Found: 383.2.

EXAMPLE 11

3-{5-Chloro-3-(4-phenylpiperazinylcarbonyl)phenoxy}propoxyamino]carboxamidine trifluoroacetate

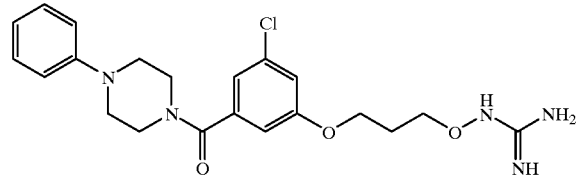

The title compound was prepared from compound 30 and 4-phenylpiperazine in a manner analogous to stepsh and i of Example 2. $^1$H NMR (300 MHz, CD$_3$OD) δ 7.27–6.85 (m, 8H), 4.16 (t, 2H, J=6.1 Hz), 4.08 (t, 2H, J =6.3 Hz), 3.31 (m, 8H), 2.18 (pentet, 2H, J=6.2 Hz). Mass spectrum (LCMS, ESI pos.) calcd. for C$_{21}$H$_{26}$N$_5$O$_3$Cl: 432.2 (M+H). Found: 432.3.

EXAMPLE 12

[3-{5-Chloro-3-(4-benzylpiperazinylcarbonyl)phenoxy}propoxyamino]carboxamidine trifluoroacetate

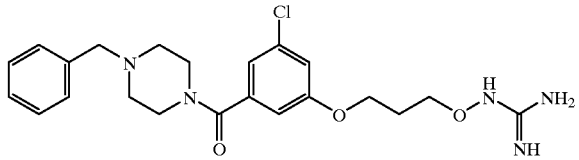

The title compound was prepared from compound 30 and 4-benzylpiperazine in a manner analogous to steps h and i of Example 2. Mass spectrum (LCMS, ESI pos.) calcd. for C$_{22}$H$_{28}$N$_5$O$_3$Cl: 446.2 (M+H). Found: 446.6.

EXAMPLE 13

[3-{5-Chloro-3-(N,N-dimethylaminocarbonyl)phenoxy}propoxyamino]carboxamidine trifluoroacetate

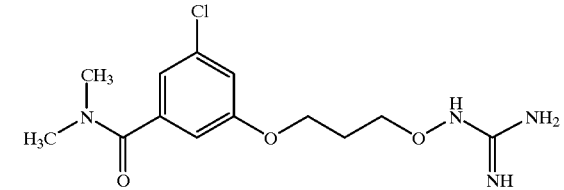

The title compound was prepared from compound 30 and N,N-dimethylamine in a manner analogous to steps h and i of Example 2. $^1$H NMR (300 MHz, DMSO-d$_6$) δ 10.99 (s, 1H), 7.64 (bs, 4H), 7.10 (t, 1H, J=2.0 Hz), 7.02 (m, 1H), 6.91 (m, 1H), 4.14 (t, 2H, J=6.3 Hz), 3.94 (t, 2H, J=6.3 Hz), 2.96 (s, 3H), 2.88 (s, 3H), 2.06 (m, 2H). Mass spectrum (LCMS, ESI pos.) calcd. for C$_{13}$H$_{19}$N$_4$O$_3$Cl: 315.1 (M+H). Found: 315.4.

EXAMPLE 14

[3-{5-Chloro-3-(piperidinylcarbonyl)phenoxy}propoxyamino]carboxamidine trifluoroacetate

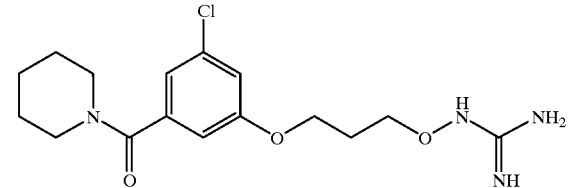

The title compound was prepared from compound 30 and piperidine in a manner analogous to steps h and i of Example 2. $^1$H NMR(300 MHz, DMSO-d$_6$) δ 7.67 (bs, 4H), 7.10 (t, 1H, J=2.0 Hz), 6.98 (t, 1H, J=2.0 Hz), 6.87 (dd, 1H, J=2.4 Hz, 1.3 Hz), 4.14 (t, 2H, J=6.2 Hz), 3.94 (t, 2H, J=6.4 Hz), 2.06 (pentet, 2H, J=6.3 Hz), 1.60–1.24 (m, 6H). Mass spectrum (LCMS, ESI pos.) calcd. for C$_{16}$H$_{23}$N$_4$O$_3$Cl: 355.1 (M+H). Found: 355.3.

EXAMPLE 15

[3-{5-Chloro-3-(4-[2-pyridyl]piperazinylcarbonyl)phenoxy}propoxyamino]carboxamidine trifluoroacetate

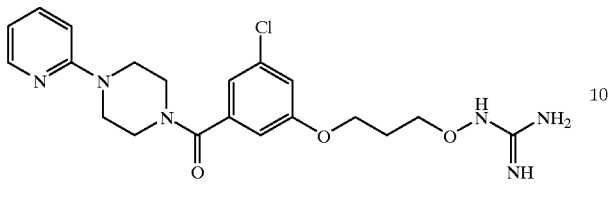

The title compound was prepared from compound 30 and 4-(2-pyridyl)piperazine in a manner analogous to steps h and i of Example 2. $^1$H NMR (300 MHz, DMSO-d$_6$) 11.19 (s, 1H), 8.11 (m, 1H), 7.77 (bs, 3H), 7.62 (m, 1H), 7.14 (t, 1H, J=2.1 Hz), 7.08 (t, 1H, J=1.5 Hz), 6.97 (dd, 1H, J=2.3 Hz, 1.3 Hz), 6.90 (d, 1H, J=8.7 Hz), 6.71 (dd, 1H, J=6.8 Hz, 5.2 Hz), 4.15 (t, 2H, J=6.4 Hz), 3.95 (t, 2H, J=6.4 Hz), 3.70–3.42 (bm, 8H), 2.07 (pentet, 2H, J=6.3 Hz). Mass spectrum (LCMS, ESI pos.) calcd. for C$_{20}$H$_{25}$N$_6$O$_3$Cl: 433.2 (M+H). Found: 431.6.

EXAMPLE 16

[3-{5-Chloro-3-(2-[1,2,3,4-tetrahydro]isoquinolinylcarbonyl)phenoxy}propoxyamino]carboxamidine trifluoroacetate

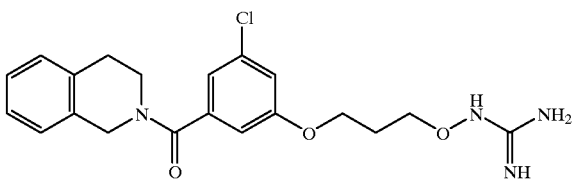

The title compound was prepared from compound 30 and 1,2,3,4-tetrahydroisoquinoline in a manner analogous to steps h and i of Example 2. Mass spectrum (LCMS, ESI pos.) calcd. for C$_{20}$H$_{23}$N$_4$O$_3$Cl: 403.1 (M+H). Found: 403.3.

EXAMPLE 17

[3-{5-Chloro-3-(azaperhydroepinylcarbonyl)phenoxy}propoxyamino]carboxamidine trifluoroacetate

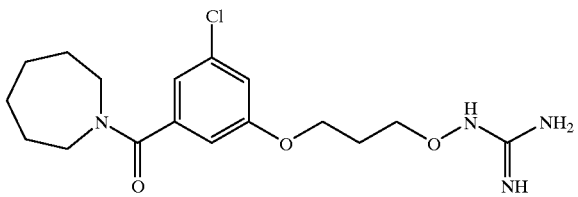

The title compound was prepared from compound 30 and N,N-cyclohexylimine in a manner analogous to steps h and i of Example 2. $^1$H NMR (300 MHz, DMSO-d$_6$) δ 11.23 (s, 1H), 7.79 (bs, 4H), 7.08 (t, 1H J=2.1 Hz), 6.97 (m, 1H), 6.86 (dd, 1H, J=2.3 Hz, 1.3 Hz), 4.13 (t, 2H, J=6.3 Hz), 3.94 (t, 2H, J=6.4Hz), 3.53 (t, 2H, J35.8 Hz), 3.27 (m, 2H), 2.08 (m, 2H), 1.71 (bm, 2H), 1.53 (bm, 6H). Mass spectum (LCMS, ESI pos.) calcd. for C$_{17}$H$_{25}$N$_4$O$_3$Cl: 369.2 (M+H). Found: 369.3.

EXAMPLE 18

Ethtyl 3-({5-[3-(amidinoaminooxy)propoxy]-3-chlorophenyl}-N-benzylcarbonylamino)propanoate trifluoroacetate

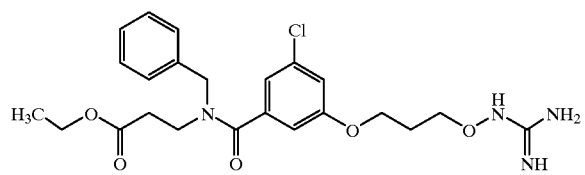

The title compound was prepared from compound 30 and benzyl (3-ethyl propionato)amine in a manner analogous to steps h and i of Example 2. Mass spectrum (LCMS, ESI pos.) calcd. for C$_{23}$H$_{29}$N$_4$O$_5$Cl: 477.2 (M+H). Found: 477.4.

EXAMPLE 19

Ethyl 1-({5-[3-(amidinoaminooxy)propoxy]-3-chlorophenyl}carbonyl)piperidine-4-carboxylate trifluoroacetate

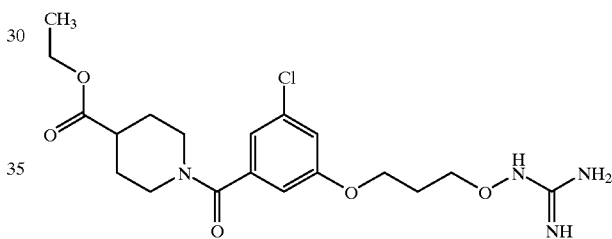

The title compound was prepared from compound 30 and 4-(carboxyethyl)piperidine in a manner analogous to steps h and i of Example 2. $^1$H NMR (300 MHz, DMSO-d$_6$) δ 11.26 (s, 1H), 7.81 (bs, 4H), 7.11 (t, 1H, J=2.1 Hz), 7.00 (t, 1H, J=1.6 Hz), 6.90 (dd, 1H J=2.3 Hz, 1.2 Hz), 4.13 (t, 2H, J=6.3 Hz), 4.08 (q, 2H, J=7.1 Hz), 3.94 (t, 2H, J=6.4 Hz), 3.09–2.89 (bm, 2H), 2.63 (tt, 1H, J=10.9 Hz, 3.8 Hz), 2.07 (pentet, 2H, J=6.3 Hz), 1.89 (bm, 2H,) 1.52 (bm, 2H), 1.18 (t, 3H, J=7.1 Hz). Mass spectrum (LCMS, ESI pos.) calcd. for C$_{19}$H$_{27}$N$_4$O$_5$Cl: 427.2(M+H). Found: 427.3.

EXAMPLE 20

[3-{5-Chloro-3-(morpholin-4-ylcarbonyl)phenoxy}propoxyamino]carboxamidine trifluoroacetate

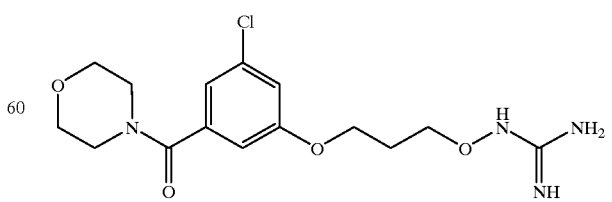

The title compound was prepared from compound 30 and morpholine in a manner analogous to steps h and i of Example 2. $^1$H NMR (300 MHz DMSO-d$_6$) δ 11.25 (s, 1H), 7.80 (bs, 4H), 7.12 (t, 1H, J=2.1 Hz), 7.03 (t, 1H, J=1.6 Hz), 6.93 (dd, 1H, J=2.3 Hz, 1.2 Hz), 4.14 (t, 2H, J=6.3 Hz), 3.94 (t, 2H, J=6.4 Hz), 3.59 (bm, 6H), 3.31 (bm, 2H), 2.07 (pentet, 2H, J=6.3 Hz). Mass spectrum (LCMS, ESI pos.) calcd. for $C_{15}H_{21}N_4O_4Cl$: 357.2 (M+H). Found: 357.6.

EXAMPLE 21

Methyl 2-({5-[3-(amidinoaminooxy)propoxy]-3-chlorophenyl}-N-metitylcarbonylamino)acetate trifluoroacetate

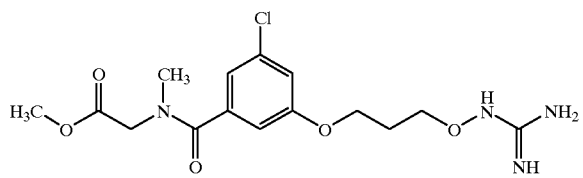

The title compound was prepared from compound 30 and methyl(2-methyl acetonato)amine in a manner analogous to steps h and i of Example 2. Mass spectrum (LCMS, ESI pos.) calcd. for $C_{15}H_{21}N_4O_5Cl$: 373.2 (M+H). Found: 373.5.

EXAMPLE 22

Tablet Preparation

Tablets containing 25.0, 50.0, and 100.0 mg, respectively, of the active compound (compound 21 of Example 1) are prepared as illustrated below:

| TABLET FOR DOSES CONTAINING FROM 25–100 MG OF THE ACTIVE COMPOUND | | | |
|---|---|---|---|
| | Amount-mg | | |
| Active Compound | 25.0 | 50.0 | 100.00 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 23

Intravenous Solution Preparation

An intravenous dosage form of the above-indicated active compounds is prepared as follows:

| Active Compound | 0.5–10.0 mg |
|---|---|
| Sodium Citrate | 5–50 mg |
| Citric Acid | 1–15 mg |
| Sodium Chloride | 1–8 mg |
| Water for Injection (USP) | q.s. to 1 ml |

Utilizing the above quantities, the active compound (21) is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md. (1994).

EXAMPLE 24

In vitro Inhibition of Purified Enzymes

Reagents: All buffer salts were obtained from Sigma Chemical Company (St. Louis, Mo.), and were of the highest purity available. The enzyme substrates, N-benzoyl-Phe-Val-Arg-p-nitroanilide (Sigma B7632), N-benzoyl-Ile-Glu-Gly-Arg-p-nitroanilide hydrochloride (Sigma B2291), N-p-Tosyl-Gly-Pro-Lys-p-nitroanilide (Sigma T6140), N-succinyl-Ala-Ala-Pro-Phe-p-nitroanilide (Sigma S7388) andN-CBZ-Val-Gly-Arg-p-nitroanilide (Sigma C7271) were obtained from Sigma. N-succinyl-Ala-Ala-Pro-Arg-p-nitroanilide (BACHEM L-1720) and N-succinyl-Ala-Ala-Pro-Val-p-nitroanilide (BACHEM L-1770) were obtained from BACHEM .(King. of Prussia, Pa.).

Human α-thrombin, human factor Xa and human plasmin were obtained from Enzyme Research Laboratories (South Bend, Ind.). Bovine α-chymotrypsin (Sigma C4129), bovine trypsin (Sigma T8642) and human kidney cell urokinase (Sigma U5004) were obtained from Sigma. Human leukocyte elastase was obtained from Elastin Products (Pacific, Mo.).

$K_i$ Determinations: All assays are based on the ability of the test compound to inhibit the enzyme catalyzed hydrolysis of a peptidep-nitroanilide substrate. In a typical $K_i$ determination, substrate is prepared in DMSO, and diluted into an assay buffer consisting of 50 mM HEPES, 200 mM NaCl, pH 7.5. The final concentrations for each of the substrates is listed below. In general, substrate concentrations are lower than the experimentally determined value for $K_m$. Test compounds are prepared as a 1.0 mg/ml solution in DMSO. Dilutions are prepared in DMSO yielding 8 final concentrations encompassing a 200 fold concentration range. Enzyme solutions are prepared at the concentrations listed below in assay buffer.

In a typical $K_i$ determination, into each well of a 96 well plate is pipetted 280 mL of substrate solution, 10 mL of test compound solution, and the plate allowed to thermally equilibrate at 37° C. in a Molecular Devices plate reader for >15 minutes. Reactions were initiated by the addition of a 10 mL aliquot of enzyme and the absorbance increase at 405 nm is recorded for 15 minutes. Data corresponding to less than 10% of the total substrate hydrolysis were used in the calculations. The ratio of the velocity (rate of change in absorbance as a function of time) for a sample containing no test compound is divided by the velocity of a sample containing test compound, and is plotted as a function of test compound concentration. The data are fit to a linear regression, and the value of the slope of the line calculated. The inverse of the slope is the experimentally determined $K_i$ value.

Thrombin: Thrombin activity was assessed as the ability to hydrolyze the substrate N-succinyl-Ala-Ala-Pro-Arg-p-nitroanilide. Substrate solutions were prepared at a concentration of 32 mM (32 mM<<Km=180 mM) in assay buffer. Final DMSO concentration was 4.3%. Purified human a-thrombin was diluted into assay buffer to a concentration of 15 nM. Final reagent concentrations were: [thrombin]= 0.5 nM, [substrate N-succinyl-Ala-Ala-Pro-Arg-p-nitroanilide]=32 mM.

Factor X [FXa]: FXa activity was assessed as the ability to hydrolyze the substrate N-benzoyl-Ile-Glu-Gly-Arg-p-nitroanilide hydrochloride. Substrate solutions were prepared at a concentration of 51 mM ($51<<K_m=1.3$ mM) in assay buffer. Final DMSO concentration was 4.3%. Purified activated human Factor X was diluted into assay buffer to a concentration of 300 nM. Final reagent concentrations were: [FXa]=10 nM, [N-benzoyl-Ile-Glu-Gly-Arg-p-nitroanilide hydrochloride]=51 mM.

Plasmin: Plasmin activity was assessed as the ability to hydrolyze the N-p-Tosyl-Gly-Pro-Lys-p-nitroanilide. Substrate solutions were prepared at a concentration of 37 mM ($37$ mM$<<K_m=243$ mM) in assay buffer. Final DMSO concentration was 4.3%. Purified human plasmin was diluted into assay buffer to a concentration of 240 nM. Final reagent concentrations were: [Plasmin]=8 nM, [N-p-Tosyl-Gly-Pro-Lys-p-nitroanilide]=37 mM.

Chymotrypsin: Chymotrypsin activity was assessed as the ability to hydrolyze N-succinyl-Ala-Ala-Pro-Phe-p-nitroanilide. Substrate solutions were prepared at a concentration of 14 mM ($14$ mM$<<K_m=62$ mM) in assay buffer. Final DMSO concentration was 4.3%. Purified bovine chymotrypsin was diluted into assay buffer to a concentration of 81 mM. Final reagent concentrations were: [Chymotrypsin]=2.7 nM, [N-succinyl-Ala-Ala-Pro-Phe-p-nitroanilide]=14 mM.

Trypsin: Trypsin activity was assessed as the ability to hydrolyze N-benzoyl-Phe-Val-Aig-p-nitroanilide. Substrate solutions were prepared at a concentration of 13 mM ($13$ M$<<K_m=291$ mM) in assay buffer. Final DMSO concentration was 4.3%. Purified bovine trypsin was diluted into assay buffer to a concentration of 120 nM. Final reagent-concentrations were: [Trypsin]=4 nM, [N-benzoyl-Phe-Val-Arg-p-nitroanilidel=13 mM.

Elastase: Elastase activity was assessed as the ability to hydrolyze N-succinyl-Ala-Ala-Pro-Val-p-nitroanilide. Substrate solutions were prepared at a concentration of 19 mM ($19$ mM$<<K_m=89$ mM) in assay buffer. Final DMSO concentration was 4.3%. Purified human leukocyte elastase was diluted into assay buffer to a concentration of 750 nM. Final reagent concentrations were: [Elastase]=25 nM, [N-succinyl-Ala-Ala-Pro-Val-p-nitroanilide]=19 mM.

Urokinase: Urokinase activity was assessed as the ability to hydrolyze N-CBZ-Val-Gly-Arg-p-nitroanilide. Substrate solutions were prepared at a concentration of 100 mM (100 mM $<K_m=1.2$mM) in assay buffer. Final DMSO concentration was 4.3%. Purified human kidney urokinase was diluted into assay buffer to a concentration of 1.2 mM. Final reagent concentrations were: [Urokinase]=40 nM, and N-CBZ-Val-Gly-Arg-p-nitroanilide]=100 mM.

The exemplified compounds of the present invention had $K_i$'s for thrombin between 20 nM and 12 $\mu$M.

The results indicate that the compounds of the present invention are inhibitors of proteases, including thrombin.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:
1. A compound having the Formula I:

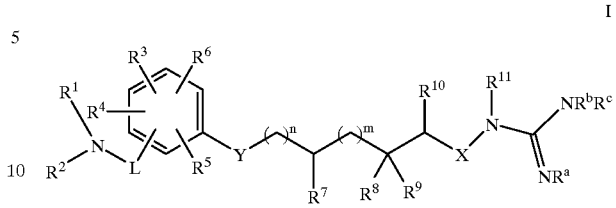

I or a solvate, hydrate or pharmaceutically acceptable salt thereof; wherein:
  L represents —C(O)— or —SO$_2$—;
  R$^1$ represents a group:

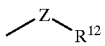

R$^2$ represents a group:

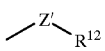

or R$^1$ and R$^2$ can be taken together with the nitrogen atom to which they are attached to form a three to seven membered ring, which optionally contains an additional nitrogen or oxygen atom, and which is optionally benzo- or pyrido-fused, said ring being saturated or partially unsaturated, and said ring having one or two optional substituents on either a ring carbon or nitrogen selected from the group consisting of halogen, hydroxy, acyloxy, alkoxy, aryloxy, alky, cycloalkyl, alkenyl, alkynyl, aryl, aralkyl, heteroaryl, heteroar(C$_{1-4}$))alkyl, carboxyalkyl, alkoxycarbonylalkyl, hydroxyalkoxyalkyl, cyano(C$_{2-10}$)alkyl, hydroxy(C$_{2-10}$)alkyl, alkoxy(C$_{2-10}$)alkyl, alkoxyalkyl, monoalkylamino(C$_{2-10}$)alkyl and dialkylamino(C$_{2-10}$) alkyl, carboxy, alkoxycarbonyl, carboxamido, formyl, alkanoyl, aroyl, aralkanoyl, sulfonyl, alkylsulfonyl, alkoxysulfonyl, and when said optional substituent is present on a ring carbon, NR$^{13}$R$^{14}$;
R$^{12}$ represents hydrogen, C$_{3-7}$ cycloalkyl, C$_{3-7}$ cycloalkenyl, C$_{3-7}$heterocycloalkyl, C$_{3-7}$ heterocycloalkenyl, aryl, or heteroaryl, which groups are optionally substituted with C$_{1-6}$ alkyl or hydroxy, or R$^{12}$ represents diarylmethyl, diheteroarylmethyl, dicycloalkylmethyl or (aryl)(heteroaryl)CH—;
Z and Z' independently represent a bond, a C$_{1-6}$ alkyl chain, a C$_{3-4}$ alkenyl chain, or a C$_{3-6}$ alkynyl chain, where one or two nitrogen, oxygen, or sulfur atoms may be optionally contained within each chain, and the chains are optionally substituted by one or more groups selected fiom halogen, hydroxy, CN, C$_{1-6}$ alkyl, C$_{1-6}$ alkoxy, C$_{1-6}$ alkoxy(C$_{1-6}$)alkyl, C$_{1-6}$ acyloxy, NR$^{13}$R$^{14}$, NHCOR$^{15}$, NHSO$_2$R$^{16}$, COR$^{15}$, CO$_2$R$^{15}$, CONR$^{13}$R$^{14}$, and SO$_2$NR$^{17}$R$^{18}$;
provided that when one of R$^1$ or R$^2$ is C$_{3-8}$ alkyl, cycloalkyl, C$_{3-8}$ alkenyl, C$_{3-8}$ alkyny aralkyl, or heteroaryl, any of which is optionally substituted, then the other of R$^1$ or R$^2$ is other than hydrogen, alkyl, aralkyl, aryl, hydroxy(C$_{2-10}$)alkyl, amino(C$_{2-10}$)alkyl, monoalkylamino(C$_{2-10}$)alkyl, dialkylamino(C$_{2-10}$) alkyl or carboxyalkyl;
R$^{13}$–R$^{16}$ represent hydrogen, C$_{1-6}$ alkyl, C$_{3-7}$ cycloalkyl, C$_{2-6}$ alkenyl, C$_{2-6}$ alknyl, C$_{6-10}$ aryl, mono- or di-hydroxy($C_{6-10}$)aryl, $C_{6-10}$ ar($C_{1-4}$)alkyl, pyridyl, pyridyl($C_{1-4}$)alkyl, carboxy($C_{1-6}$)-alkyl, $C_{1-4}$ alkoxycarbonyl($C_{1-4}$)alkyl, cyano($C_{2-6}$)alkyl, hydroxy ($C_{2-6}$)alkyl, $C_{1-4}$ alkoxy($C_{2-6}$)alkyl, momo- and di-($C_{1-4}$)alkylamino($C_{2-6}$)alkyl;

or $R^{13}$ and $R^{14}$ together with the nitrogen to which they are attached form a $C_{3-7}$ heterocycloalkyl ring, or $R^{16}$ additionally may represent trifluoromethyl;

$R^{17}$ and $R^{18}$ are independently selected from the group consisting of hydrogen, $C_{1-6}$ alkyl, $C_{3-7}$ cycloalkyl, $C_{2-6}$ alkenyl, $C_{2-6}$ alkynyl, $C_{6-10}$ aryl, $C_{6-10}$ ar($C_{1-4}$) alkyl, pyridyl, pyridyl($C_{1-4}$)alkyl, carboxy($C_{1-6}$)alkyl, $C_{1-4}$ alkoxycarbonyl-($C_{1-4}$)alkyl, cyano($C_{2-6}$)alkyl, hydroxy($C_{2-6}$)alky alkoxy($C_{2-6}$)alkyl, and mono- and di-($C_{1-4}$)alkylamino($C_{2-6}$)alkyl, or $R^{17}$ and $R^{18}$ can be taken together with the nitrogen atom to which they are attached to form a heterocyclic ring selected from the group consisting of N-morpholino; N-piperazinyl, optionally substituted in the 4-position with $C_{1-6}$ alkyl, $C_{1-6}$ hydroxyalkyl, $C_{6-10}$ aryl, $C_{6-10}$ aryl($C_{1-6}$)alkyl, $C_{1-6}$ alkylsulfonyl, $C_{6-10}$ arylsulfonyl, $C_{1-6}$ alkylcarbonyl, morpholino or $C_{6-10}$ arylcarbonyl; N-pyrrolyl; N-piperidinyl; N-prrolidinyl N-dihydropyridyl; and N-indolyl; wherein any of said heterocyclic rings can be optionally C-substituted;

$R^3$, $R^4$, $R^5$ and $R^6$ are each independently hydrogen, alkyl, cycloalkyl, alkenyl, alkyniyl, optionally substituted aryl, optionally substituted aralkyl, optionally substituted heteroaryl, trifluoromethyl, halogen, hydroxyalkyl, cyano, nitro, carboxamido, —$CO_2R^x$, —$CH_2OR^x$ or —$OR^x$, or when present on adjacent carbon atoms, $R^3$ and $R^4$ may also be taken together to form —CH=CH—CH=CH— or —$(CH_2)_q$—, where q is from 2 to 6, and $R^5$ and $R^6$ are defined as above;

$R^x$ is hydrogen, alkyl or cycloalkyl wherein said alkyl or cycloalkyl may optionally have one or more unsaturations;

Y is —O—, —$NR^{19}$—, —S—, —$CHR^{19}$— or a covalent bond;

$R^{19}$, is hydrogen, $C_{1-6}$ alkyl, benzyl, phenyl, $C_{2-10}$ hydroxyalkyl, $C_{2-10}$ arninoalkyl, $C_{1-4}$ monoalkylamino ($C_{2-8}$)alkyl, $C_{1-4}$ dialkylamino($C_{2-8}$)alkyl or $C_{2-10}$ carboxyalkyl;

$R^7$ is hydrogen, alkyl, aralkyl, aryl, hydroxyalkyl, aminoalkyl, monoalkylaminoalkyl, dialkylaminoalkyl, carboxyalkyl, hydroxy, alkoxy, aralkoxy, aryloxy, heteroaryloxy, or mono- or di- alkylamino, provided that n is other than zero when $R^7$ is hydroxy, alkoxy, aralkoxy, aryloxy, heteroaryloxy, or mono- or di- alkylamino;

$R^8$, $R^9$ and $R^{10}$ are each independently hydrogen, alkyl, aralkyl, aryl, hydroxyalkyl, aminoalkyl, monoalkylaminoalkyl, dialkylaminoalkyl or carboxyalkyl;

or $R^7$ and $R^8$ are taken together to form —$(CH_2)_y$—, where y is zero, 1 or 2, while $R^9$ and $R^{10}$ are defined as above; or $R^7$ and $R^{10}$ are taken together to form —$(CH_2)_t$—, where t is zero, or 1 to 8, while $R^8$ and $R^9$ are defined as above; or $R^8$ and $R^9$ are taken togeth to form —$(CH_2)_r$—, where r is 2–8, while $R^7$ and $R^{10}$ are defined as above;

X is oxygen or NH;

$R^{11}$ is hydrogen, alkyl, aralkyl, aryl, hydroxyalkyl, aminoalkyl, monoalkylaminco($C_{2-10}$)alkyl, dialkylamino($C_{2-10}$)alkyl or carboxyalkyl;

$R^a$, $R^b$ and $R^c$ are independently hydrogen, alkyl, hydroxy, alkoxy, aryloxy, aralkoxy, alkoxycarbonyloxy, cyano or —$CO_2R^w$;

$R^w$ is alkyl, trichloroethyl, cycloalkyl, phenyl, benzyl,

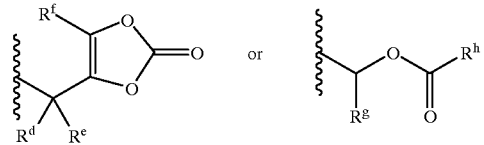

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl;

n is from zero to 8; and m is from zero to 4.

2. A compound of claim 1, wherein the moiety —L—$NR^1R^2$ is attached to the benzene ring in the meta-position.

3. A compound having the structure of Formula Ia:

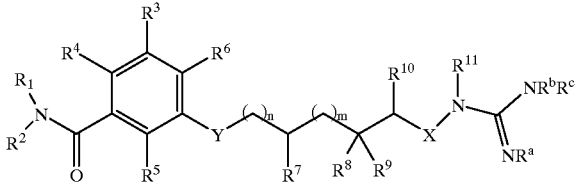

Ia or a solvate, hydrate or pharmaceutically acceptable salt thereof, wherein:

$R^1$ and $R^2$ are taken together with the nitrogen atom to which they are attached to form a three to seven membered ring, which optionally contains an additional nitrogen or oxygen atom, and which is optionally benzo- or pyrido-fused, said ring being saturated or partially unsaturated, and said ring having one or two optional substituents on either a ring carbon or nitrogen selected from the group consisting of halogen, hydroxy, acyloxy, alkoxy, aryloxy, alkyl, cycloallkyl, alkenyl, alkynyl, aryl, aralkyl, heteroaryl, heteroar($C_{1-4}$)alkyl, carboxyalkyl, alkoxycarbonylalkyl, hydroxyalkoxyalkyl, cyano($C_{2-10}$)alkyl, hydroxy($C_{2-10}$)alkyl, alkoxy($C_{2-10}$)alkyl, alkoxyalkyl, monoalkylamino($C_{2-10}$)alkyl and dialkylamino($C_{2-10}$) alkyl, carboxy, alkoxycarbonyl, carboxamido, formyl, alkanoyl, aroyl, aralkanoyl, sulfonyl, alkylsulfonyl, alkoxysulfonyl, and when said optional substituent is present on a ring carbon, $NR^{13}R^{14}$;

$R^{13}$ and $R^{14}$ independently represent hydrogen, $C_{1-6}$ alkyl, $C_{3-7}$ cycloalkyl, $C_{2-6}$ alkenyl ($_{2-6}$ alkynyl, $C_{6-10}$ aryl, mono- or di-hydroxy($C_{6-10}$)aryl, $C_{6-10}$ ar($C_{1-4}$) alkyl, pyridyl, pyridyl($C_{1-4}$)alkyl, carboxy($C_{1-6}$)-alkyl, $C_{1-4}$ alkoxycarbonyl($C_{1-4}$)alkyl, cyano($C_{2-6}$)alkyl, hydroxy($C_{2-6}$)alkyl, $C_{1-4}$ alkoxy($C_{2-6}$)alkyl, mono ($C_{1-4}$)alkylamino($C_{2-6}$)alkyl and di($C_{1-4}$)alkylamino ($C_{2-6}$)alkyl;

or $R^{13}$ and $R^{14}$ together with the nitrogen to which they are attached form a $C_{3-7}$ heterocycloalkyl ring;

$R^3$, $R^4$, $R^5$ and $R^6$ are each independently one of hydrogen, alkyl, cycloalkyl, alkenyl, alkynyl, optionally substituted aryl, optionally substituted aralkyl, optionally substituted heteroaryl, trifluoromethyl, halogen, hydroxyalkyl, cyano, nitro, carboxamido, —$CO_2R^x$, —$CH_2OR^x$ or —$R^x$, or when present on adjacent carbon atoms, $R^3$ and $R^4$ may also be taken together to form one of —CH=CH—CH=CH— or —$(CH_2)_q$—, where q is from 2 to 6, and $R^5$ and $R^6$ are defined as above;

$R^x$ is hydrogen, alkyl or cycloalkyl wherein said alkyl or cycloalkyl groups may optionally have one or more unsaturations;

Y is —O—, —$NR^{19}$—, —S—, —$CHR^{19}$— or a covalent bond;

$R^{19}$ is hydrogen, $C_{1-6}$ alkyl, benzyl, phenyl, $C_{2-10}$ hydroxyalkyl, $C_{2-10}$ aminoalkyl, $C_{1-4}$ monoalkylamino($C_{2-8}$)alkyl, $C_{1-4}$ dialkylamino($C_{2-8}$)alkyl or $C_{2-10}$ carboxyalkyl;

$R^7$ is hydrogen, alkyl, aralkyl, aryl, hydroxyalkyl, aminoalkyl, monoalkylaminoallyl, dialkylarninoalkyl, carboxyalkyl, hydroxy, alkoxy, aralkoxy, aryloxy, heteroaryloxy, or mono- or di-alkylamino, provided that n is other than zero when $R^7$ is hydroxy, alkoxy, aralkoxy, aryloxy, heteroaryloxy, or mono- or di-alkylamino;

$R^8$, $R^9$ and $R^{10}$ are independently hydrogen, alkyl, aralkyl, aryl, hydroxyalkyl, aminoally, monoalkylaminoalkyl, dialkylaminoalkyl or carboxyalkyl;

or $R^7$ and $R^8$ are taken together to form —$(CH_2)_y$—, where y is zero, 1 or 2, while $R^9$ and $R^{10}$ are defined as above; or $R^7$ and $R^{10}$ are taken together to form —$(CH_2)_t$—, where t is zero, or 1 to 8, while $R^8$ and $R^9$ are defined as above; or $R^8$ and $R^9$ are taken together to form —$(CH_2)_r$—, where r is 2–8, while $R^7$ and $R^{10}$ are defined as above;

X is oxygen or NH;

$R^{11}$ is hydrogen, alkyl, aralkyl, aryl, hydroxyalkyl, aminoalkyl, monoalkylamino($C_{2-10}$)alkyl, dialkylamino($C_{2-10}$)alkyl or carboxyalkyl;

$R^a$, $R^b$ and $R^c$ are independently hydrogen, alkyl, hydroxy, alkoxy, aryloxy, aralkoxy, alkoxycarbonyloxy, cyano or —$CO_2R^w$;

$R^w$ is alkyl, trichloroethyl, cycloalkyl, phenyl, benzyl,

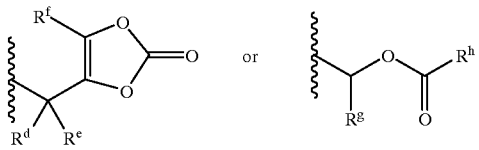

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl;

n is from zero to 8; and m is from zero to 4.

4. A compound of claim 3, wherein $R^3$ is hydrogen, $C_{1-3}$ alkyl, halogen, or $C_{1-2}$ alkoxy.

5. A compound of claim 3, wherein $R^4$, $R^5$ and $R^6$ independently represent hydrogen or halogen.

6. A compound of claim 3, wherein Y is divalent oxygen (—O—), —$NR^{19}$— or a covalent bond.

7. A compound of claim 3, wherein $R^{19}$ is hydrogen, $C_{1-6}$ alkyl or $C_{3-6}$ cycloalikyl.

8. A compound of claim 3, wherein $R^{11}$ is hydrogen or $C_{1-6}$ alkyl.

9. A compound of claim 3, wherein $R^7$, $R^8$, $R^9$ and $R^{10}$ are independently one of hydrogen, $C_{1-6}$ alkyl, $C_{6-10}$ ar($C_{1-6}$)alkyl, $C_{6-10}$ aryl, $C_{2-10}$ hydroxyalkyl or $C_{2-7}$ carboxyalkyl.

10. A compound of claim 9, wherein $R^7$, $R^8$, $R^9$ and $R^{10}$ are independently hydrogen, methyl, ethyl, propyl, n-butyl, benzyl, phenylethyl, 2-hydroxyethyl, 3-hydroxypropyl, 4-hydroxybutyl, 2-carboxymethyl, 3-carboxyethyl and 4-carboxypropyl.

11. A compound of claim 3, wherein $R^7$ and $R^8$ are taken together to form —$(CH_2)_y$— and y is 2.

12. A compound of claim 3, wherein $R^8$ and $R^9$ are taken together to form —$CH_2)_r$— and r is2.

13. A compound of claim 3, wherein X is O.

14. A compound of claim 3, wherein $R^a$, $R^b$ and $R^c$ are independently hydrogen, hydroxy, $C_{1-6}$ alkyl, $C_{1-6}$ alkoxy, cyano or —$CO_2R^w$, where $R^w$, in each instance, is selected from the group consisting of $C_{1-4}$alkyl, trichloroethyl, $C_{4-7}$ cycloalkyl and benzyloxycarbonyl.

15. A compound of claim 14, wherein $R^a$, $R^b$ and $R^c$ are independently selected fiom the group consisting of hydrogen, methyl, ethyl, propyl, n-butyl, hydroxy, methoxy, ethoxy, cyano, —$CO_2CH_3$, —$CO_2CH_2CH_3$ and —$CO_2CH_2CH_2CH_3$.

16. A compound of claim 15, wherein $R^a$, $R^b$ and $R^c$ are each hydrogen.

17. A compound of claim 3, wherein $R^a$, $R^b$ and $R^c$ are independently —$CO_2R^w$, where $R^w$ is one of

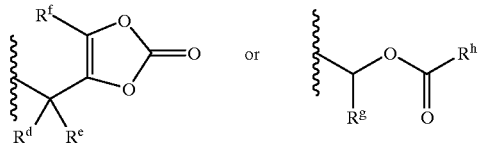

where $R^d$, $R^e$, $R^f$, $R^g$ and $R^h$ are as defined in claim 3.

18. A compound of claim 3, wherein $R^d$, $R^e$ and $R^g$ are each hydrogen, $R^f$ is medlyl, and $R^h$ is berizyl or tert-butyl.

19. A compound of claim 3, wherein n is zero, 1or 2.

20. A compound of claim 3, wherein m is zero, 1, 2 or 3.

21. A compound of claim 3, wherein $R^1$ and $R^2$ are taken together with the nitrogen to which they are attached to form a $C_{3-7}$ heterocycloalkyl or $C_{3-7}$ heterocycloalkenyl group, optionally benzo fused and optionally including an oxygen atom or an additional nitrogen atom, and which may be optionally substituted by $C_{1-6}$ alkyl hydroxy, $C_{1-4}$ alkoxy, $C_{2-6}$ alkoxycarbonyl, formyl, ($C_{6-10}$)ar($C_{1-4}$)alkyl, $C_{6-10}$ aryl, pyridyl, hydroxyalkoxyalkyl, halogen, or $NR^{13}R^{14}$;

$R^{13}$ and $R^{14}$ independently represent hydrogen, $C_{1-6}$ alkyl, $C_{3-7}$cycloalkyl, $C_{2-6}$ alkenyl, $C_{2-6}$ alkynyl, $C_{6-10}$ aryl, $C_{6-10}$ ar($C_{1-4}$)alkyl, pyridyl, pyridyl($C_{1-4}$)alkyl, carboxy($C_{1-6}$)-alky, $C_{1-4}$ alkoxycarbonyl($C_{1-4}$)alkyl, cyano($C_{2-6}$)alkyl, hydroxy($C_{2-6}$)alkyl, $C_{1-4}$ alkoxy($C_{2-6}$)alkyl, di-($C_{1-4}$)alkylamino($C_{2-6}$)alkyl;

or $R^{13}$ and $R^{14}$ together with the nitrogen to which they are attached form a $C_{3-7}$ heterocycloalkyl ring;

$R^3$ is hydrogen, $C_{1-3}$ alkyl, halogen or $C_{1-2}$ alkoxy;

$R^4$, $R^5$ and $R^6$ are hydrogen or halogen;

Y is —O—;

$R^a$, $R^b$ and $R^c$ are each one of hydrogen, $C_{1-4}$ alkyl, hydroxy, $C_{1-4}$ alkoxy, phenoxy, $C_{1-4}$ alkyloxycarbonyl, benzyloxycarbonyl, cyano,

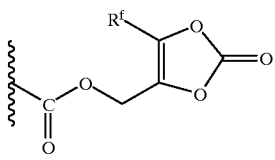

or

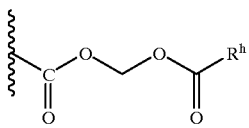

where $R^h$ is benzyl, methyl, ethyl, isopropyl, sec-butyl or t-butyl, and where $R^f$ is hydrogen or $C_{1-6}$ alkyl;

- $R^{11}$ is one of hydrogen, $C_{1-6}$ alkyl, $C_{6-10}$ ar($C_{1-6}$)alkyl, $C_{6-10}$ axyl, $C_{2-10}$ hydroxyalkyl, $C_{2-10}$ aminoalkyl, mono($C_{1-4}$)alkylamino($C_{2-8}$)alkyl, di($C_{1-4}$)alkylamino ($C_{2-8}$)alkyl or $C_{2-10}$ carboxyalkyl;
- $R^7$, $R^8$, $R^9$ and $R^{10}$ are independently one of hydrogen, $C_{1-6}$ alkyl $C_{2-10}$ carboxyalkyl or $C_{2-10}$ hydroxyalkyl, or $R^7$ and $R^8$ are taken together to form $-(CH_2)_y-$ where y is zero, 1or 2, while $R^9$ and $R^{10}$ are defined as above; or $R^7$ and $R^{10}$ are taken together to form $-(CH_2)_t-$, where t is zero (a bond), or 1, 2 or 3, while $R^1$ and $R^9$ are defined as above; or $R^8$ and $R^9$ are taken together to form $-(CH_2)_r-$, where r is 2, 3, or 4, while $R^7$ and $R^{10}$ are defined as above;

n is from zero to 4; and m is from zero to 4.

22. A compound of claim 3 having the Formula IIa:

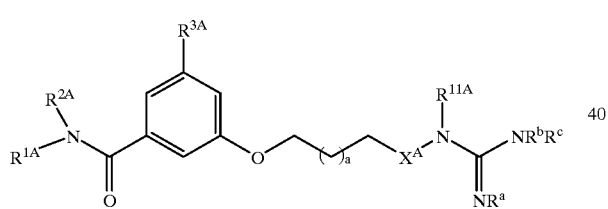

IIa or a solvate, hydrate, pharmaceutically acceptable salt or prodrug thereof, wherein:

$R^{1A}$ and $R^{2A}$ are taken together with the nitrogen atom to which they are attached to form a three to seven membered ring, which optionally contains an additional nitrogen or oxygen atom, and which is optionally benzo- or pyrido-fused, said ring being saturated or partially unsaturated, and said ring having one or two optional substituents on either a ring carbon or nitrogen selected from the group consisting of halogen, hydroxy, acyloxy, alkoxy, aryloxy, alkyl, cycloalkyl, alkenyl, alkynyl, aryl, aralkyl, heteroaryl, heteroar($C_{1-4}$)alkyl, carboxyalkyl, alkoxycarbonylalkyl, hydroxyalkoxyalkyl, cyano($C_{2-10}$)alkyl, hydroxy($C_{2-10}$)alkyl, alkoxy($C_{2-10}$)alkyl, alkoxyalkyl, monoalkylamino($C_{2-10}$)alkyl and dialkylamino($C_{2-10}$) alkyl, carboxy, alkoxycarbonyl, carboxaniido, formyl, alkanoyl, aroyl, aralkanoyl, sulfonyl, alkylsulfonyl, alkoxysulfonyl, and when said optional substituent is present on a ring carbon, $NR^{13}R^{14}$;

$R^{13}$ and $R^{14}$ independently represent hydrogen, $C_{1-6}$ alkyl, $C_{3-7}$ cycloalkyl, $C_{2-6}$ alkenyl, $C_{2-6}$ alkynyl, $C_{6-10}$ aryl, hydroxy($C_{6-10}$)aryl, $C_{6-10}$ ar($C_{1-4}$)alkyl, pyridyl, pyridyl($C_{1-4}$)alkyl, carboxy($C_{1-6}$)-alkyl, $C_{1-4}$ alkoxycarbonyl($C_{1-4}$)alkyl, cyano($C_{2-6}$)alkyl, hydroxy ($C_{2-6}$)alkyl, $C_{1-4}$ alkoxy($C_{2-6}$)alkyl, mono-($C_{1-4}$) alkylamino($C_{2-6}$)alkyl, or di-($C_{1-4}$)alkylamino($C_{2-6}$) alkyl, or $R^{13}$ and $R^{14}$ together with the nitrogen to which they are attached form a $C_{3-7}$ heterocycloalkyl ring;

$R^{3A}$ represents $C_{1-3}$ alkyl or halogen;

$R^{11A}$ represents hydrogen, $C_{6-10}$ ar($C_{1-4}$) alkyl or $C_{1-4}$ alkyl;

$X^A$ is oxygen or NH;

$R^a$, $R^b$ and $R^c$ are hydrogen; and a is from zero to 8.

23. A compound of claim 22, wherein $X^A$ is oxygen.

24. A compound of claim 22, wherein:

$R^{1A}$ and $R^{2A}$ are taken together with the nitrogen to which they are attached to form a $C_{3-7}$ heterocycloalkyl or $C_{3-7}$ heterocycloalkenyl group, optionally benzo fuised and optionally including an oxygen atom or an additional nitrogen atom, and which may be optionally substituted by $C_{1-6}$ alkyl, hydroxy, $C_{1-4}$ alkoxy, $C_{2-6}$ alkoxycarbonyl, formyl, ($C_{6-10}$)ar($C_{1-4}$)alkyl $C_{6-10}$ aryl, pyridyl, hydroxy($C_{1-4}$)alkoxy($C_{1-4}$)alkyl, halogen, or $NR^{13}R^{14}$;

$R^{13}$ and $R^{14}$ independently represent hydrogen, $C_{1-6}$ alkyl, $C_{3-7}$ cycloalkyl, $C_{2-6}$ alkenyl, $C_{2-6}$ alkynyl, $C_{6-10}$ aryl, hydroxy($C_{6-10}$)aryl, $C_{6-10}$ ar($C_{1-4}$)alkyl, pyridyl, pyridyl($C_{1-4}$)alkyl, carboxy($C_{1-6}$)-alkyl, $C_{1-4}$ alkoxycarbonyl($C_{1-4}$)alkyl, cyano($C_{2-6}$)alkyl, hydroxy ($C_{2-6}$)alkyl, $C_{1-4}$ alkoxy($_{2-6}$)alkyl, mono-($C_{1-4}$) alkylamino($C_{2-6}$)alkyl, or di-($C_{1-4}$)alkylamino($C_{2-6}$) alkyl;

or $R^{13}$ and $R^{14}$ together with the nitrogen to which they are attached form a $C_{3-7}$ heterocycloalkyl ring;

$R^{3A}$ represents halogen;

$X^A$ is $-O-$;

$R^{11A}$ is hydrogen, $C_{6-10}$ ar($C_{1-4}$) alkyl or $C_{1-4}$ alkyl;

$R^a$, $R^b$ and $R^c$ are hydrogen; and a is 1.

25. A compound of claim 24, wherein $R^{3A}$ is methyl.

26. A compound of claim 24, wherein $R^{3A}$ is chloro.

27. A compound of claim 22, which is one of

[3-{5-chloro-3-(4-benzylpiperidinylcarbonyl) phenoxy}propoxyamino]carboxamidine trifluoroacetate;

[3-{5-chloro-3-(4-formylpiperazinylcarbonyl) phenoxy}propoxyamino]carboxamidine trifluoroacetate;

[3-{5-chloro-3-(4-phenylpiperazinylcarbonyl) phenoxy}propoxyamino]carboxamidine trifluoroacetate;

[3-{5-chloro-3-(4-benzylpiperazinylcarbonyl) phenoxy}propoxyamino]carboxamidine trifluoroacetate;

[3-5-chloro-3-(piperidinylcarbonyl) phenoxy}propoxyarnino]carboxamidine trifluoroacetate;

[3-{5-chloro-3-(4-[2-pyridyl]piperazinylcarbonyl) phenoxy}propoxyamino]carboxamidine trifluoroacetate;

[3-{5-chloro-3-(4-[4-pyridyl]piperazinylcarbonyl) phenoxy}propoxyamino]carboxamidine trifluoroacetate;

[3-{5-chloro-3-(2-[1,2,3,4-tetrahydro]isoquinolinylcarbonyl)phenoxy}propoxyamino]carboxamidine trifluoroacetate;

[3-{5-chloro-3-(azaperhydroepinylcarbonyl)phenoxy}propoxyamino]carboxamidine trifluoroacetate;

ethyl 1-({5-[3-(amidinoaminooxy)propoxy]-3-chlorophenylcarbonyl)piperidine-4-carboxylate trifluoroacetate; and

[3-{5-chloro-3-(morpholin-4-ylcarbonyl)phenoxy}propoxyamino]carboxamidine trifluoroacetate.

28. The process reparing a hydroxyguanidine compound of claim 1, or claim 3 comprising reacting an alkoxyamine compound of the Formula IX:

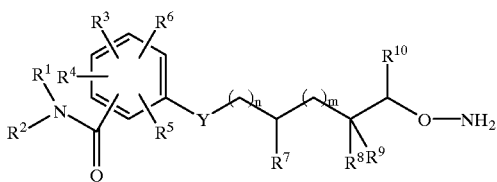

IX wherein $R^1$–$R^6$, Y, n, m, $R^7$, $R^8$, $R^9$ and $R^{10}$ are defined as in claim 1, with a guanidinylating reagent.

29. The process of claim 28 wherein the guanidinylating reagent is selected from the group consisting of aminoiminosulfonic acid, substituted 1H-pyrazole-1-carboxamidines, and N,N'-bis(tert-butoxycarbonyl) S-methyl isothiourea.

30. A process for preparing an aminoguanidine compound of claim 1, or claim 3 comprising reacting an aminoguanidine of the Formula VII:

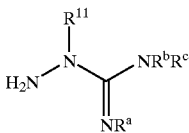

VII wherein $R^{11}$, $R^a$, $R^b$ and $R^c$ are as defined in claim 1, or claim 3 with a carbonyl-containing compound of the Formula VIII:

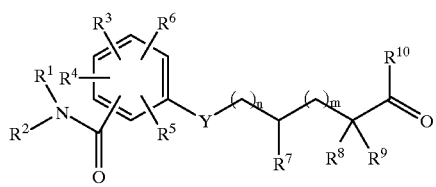

VIII wherein $R^1$–$R^6$, Y, n, m, $R^7$, $R^8$, $R^9$ and $R^{10}$ are as defined in claim 1, to form an amidinohydrazone; and thereafter selectively reducing the hydrazone carbon to nitrogen double bond of the amidinohydrazone.

31. The process of claim 30, wherein the aminoguanidine is provided as a salt.

32. The process of claim 30, wherein the aminoguanidine is provided as a nitrate salt.

33. The process of claim 30, wherein
(a) the first step proceeds at ambient temperature using alcohol as a solvent; and
(b) 4N HCl in dioxane is added to the reaction mixture.

34. A pharmaceutical composition for inhibiting proteolysis in a mammal, comprising an amount of a compound of claim 1 or claim 3 effective to inhibit proteolysis, and a pharmaceutically acceptable carrier or diluent.

35. The pharmaceutical composition of claim 34, comprising an amount of said compound effective to inhibit a trypsin-like protease.

36. A method of inhibiting proteolysis in a mammal, comprising administering to the mammal a composition of claim 34.

37. The method of claim 36, wherein a trypsin-like protease is inhibited.

38. A method of treating pancreatitis, thrombosis, ischemia, stroke, restenosis, emphysema or inflammation in a mammal, comprising administering to the mammal a composition of claim 34.

39. A method of inhibiting thrombin-induced platelet aggregation and clotting of fibrinogen in plasma, comprising administering to the mammal a composition of claim 34.

40. A method for inhibiting thrombin in blood comprising adding to the blood a compound of claim 1 or claim 3.

41. A method for inhibiting formation of blood platelet aggregates in blood comprising adding to the blood a compound of claim 1 or claim 3.

42. A method for inhibiting thrombus formation in blood comprising adding to the blood a compound of claim 1 or claim 3.

* * * * *

UNITED STATES PATENT AND TRADEMARK OFFICE
CERTIFICATE OF CORRECTION

PATENT NO. : 6,344,466 B2  
DATED : February 5, 2002  
INVENTOR(S) : Soll et al.

It is certified that error appears in the above-identified patent and that said Letters Patent is hereby corrected as shown below:

Title page,
Item [75], change the city of residence of applicant Tianbao Lu by deleting "Collegevile" and inserting therein -- Kennett Square --.
Change city of residence of applicant Bruce E. Tomczuk by deleting "Collegevile" and inserting therein -- Collegeville --.

Column 54,
Line 60, delete "$C_{3-8}$ alkyny aralkyl" and insert therein -- $C_{3-8}$ alkynyl, aryl, aralkyl --.
Line 67, delete "$C_{2-6}$ alknyl" and insert therein -- $C_{2-6}$ alkynyl --.

Column 55,
Line 4, delete "momo-" and insert therein -- mono- --.
Line 14, delete "hydroxy($C_{2-6}$)alky alkoxy($C_{2-6}$)alkyl" and insert therein -- hydroxy($C_{2-6}$)alkyl, $C_{1-4}$ alkoxy($C_{2-6}$)alkyl --.
Line 23, delete "N-prrolidinyl" and insert therein -- N-pyrrolidinyl --.
Line 27, delete "alkyniyl" and insert therein -- alkynyl --.
Line 41, delete "arninoalkyl" and insert therein -- aminoalkyl --.
Line 61, delete "togeth" and insert therein -- together --.
Line 64, delete "monoalkylaminco($C_{2-10}$)alkyl" and insert therein -- monoalkylamino($C_{2-10}$)alkyl --.

Column 57,
Line 2, delete "–$R^{x}$" and insert therein -- –$OR^{x}$ --.
Line 24, delete "aminoally" and insert therein -- aminoalkyl --.
Line 62, delete "$C_{3-6}$ cycloalikyl" and insert therein -- $C_{3-6}$ cycloalkyl --.

Column 58,
Line 37, delete "medlyl" and insert therein -- methyl --.
Line 37, delete "berizyl" and insert therein -- benzyl --.
Line 58, delete "di-($C_{1-4}$)alkylamino($C_{2-6}$)alkyl" and insert therein -- mono– and di-($C_{1-4}$)alkylamino($C_{2-6}$)alkyl --.

Column 59,
Line 19, delete "axyl" and insert therein -- aryl --.
Line 27, delete "$R^{1}$" and insert therein -- $R^{8}$ --.
Line 62, delete "carboxaniido" and insert therein -- carboxamido --.

UNITED STATES PATENT AND TRADEMARK OFFICE
CERTIFICATE OF CORRECTION

PATENT NO.   : 6,344,466 B2
DATED        : February 5, 2002
INVENTOR(S)  : Soll et al.

It is certified that error appears in the above-identified patent and that said Letters Patent is hereby corrected as shown below:

Column 60,
Line 19, delete "fuised" and insert therein -- fused --.
Line 58, delete "[3-5-chloro-3-(piperidinylcarbonyl)phenoxy}propoxyarnino]carboxamidine trifluoroacetate" and insert therein -- [3-{5-chloro-3-(piperidinylcarbonyl)phenoxy} propoxyamino] carboxamidine trifluoroacetate --.

Column 61,
Lines 6-8, delete "ethyl 1-({5-[3-(amidinoaminooxy}propoxy]-3-chlorophenylcarbonyl)piperidine-4-carboxylate trifluoroacetate" and insert therein -- ethyl 1-({5-[3-(amidinoaminooxy)propoxy]-3-chlorophenyl}carbonyl)piperidine-4-carboxylate trifluoroacetate --.
Line 13, delete "reparing" and insert therein -- for preparing --.

Signed and Sealed this

Twenty-ninth Day of October, 2002

*Attest:*

*Attesting Officer*

JAMES E. ROGAN
*Director of the United States Patent and Trademark Office*